(12) United States Patent
Ganesan et al.

(10) Patent No.: US 12,264,197 B2
(45) Date of Patent: Apr. 1, 2025

(54) ANTI-Vβ17/ANTI-CD123 BISPECIFIC ANTIBODIES

(71) Applicant: JANSSEN BIOTECH, INC., Horsham, PA (US)

(72) Inventors: Rajkumar Ganesan, Blue Bell, PA (US); Iqbal S. Grewal, Newtown, PA (US); Manuel Alejandro Sepulveda, West Windsor, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 827 days.

(21) Appl. No.: 17/437,771

(22) PCT Filed: Mar. 11, 2020

(86) PCT No.: PCT/IB2020/000342
§ 371 (c)(1),
(2) Date: Sep. 9, 2021

(87) PCT Pub. No.: WO2020/183245
PCT Pub. Date: Sep. 17, 2020

(65) Prior Publication Data
US 2022/0127359 A1 Apr. 28, 2022

Related U.S. Application Data
(60) Provisional application No. 62/816,464, filed on Mar. 11, 2019.

(51) Int. Cl.
*C07K 16/28* (2006.01)
*A61K 39/00* (2006.01)
*A61P 35/02* (2006.01)

(52) U.S. Cl.
CPC .......... *C07K 16/2809* (2013.01); *A61P 35/02* (2018.01); *C07K 16/2866* (2013.01); *A61K 2039/505* (2013.01); *C07K 2317/31* (2013.01); *C07K 2317/52* (2013.01); *C07K 2317/73* (2013.01); *C07K 2317/92* (2013.01)

(58) Field of Classification Search
CPC ............ C07K 16/2809; C07K 16/2866; C07K 2317/31; C07K 2317/52; C07K 2317/73; C07K 2317/92; A61P 35/02; A61K 2039/505
See application file for complete search history.

(56) References Cited

U.S. PATENT DOCUMENTS

| | | | |
|---|---|---|---|
| 6,084,087 A | 7/2000 | Friedman | |
| 6,221,352 B1 | 4/2001 | Howell | |
| 6,413,516 B1 | 7/2002 | Chang | |
| 6,521,427 B1 | 2/2003 | Evans | |
| 6,670,127 B2 | 12/2003 | Evans | |
| 6,737,056 B1 | 5/2004 | Presta | |
| 9,168,314 B2 | 10/2015 | Satijn | |
| 9,850,310 B2 * | 12/2017 | Gaudet | ............. C07K 16/2809 |
| 11,230,598 B2 * | 1/2022 | Tedder | ................ A61K 38/164 |
| 2006/0286104 A1 | 12/2006 | Hanke | |
| 2007/0071675 A1 | 3/2007 | Wu | |
| 2009/0182127 A1 | 7/2009 | Kjaergaard | |
| 2010/0015133 A1 | 1/2010 | Tomoyuki | |
| 2010/0028637 A1 | 2/2010 | Tavsanli | |
| 2011/0123532 A1 | 5/2011 | Gurney | |
| 2012/0149876 A1 | 6/2012 | Von Kreudenstein | |
| 2013/0195849 A1 | 8/2013 | Spreter Von Kreudenstein | |
| 2013/0230540 A1 | 9/2013 | Holmes | |
| 2016/0053020 A1 | 2/2016 | Verploegen | |
| 2016/0347858 A1 | 12/2016 | Sakamoto | |
| 2017/0015738 A1 | 1/2017 | Pedersen | |
| 2017/0088620 A1 | 3/2017 | Nioi | |
| 2017/0267756 A1 | 9/2017 | Riddell | |
| 2022/0089731 A1 | 3/2022 | Ganesan | |
| 2022/0089737 A1 | 3/2022 | Ganesan | |

FOREIGN PATENT DOCUMENTS

| | | |
|---|---|---|
| EP | 0534878 | 3/1993 |
| RU | 2016129045 A | 1/2018 |
| WO | 2006028936 | 3/2006 |
| WO | 2006116269 A2 | 11/2006 |
| WO | 2009139822 A1 | 11/2009 |
| WO | 2011014469 A1 | 2/2011 |
| WO | 2011131746 A2 | 10/2011 |
| WO | 2014159531 A1 | 10/2014 |
| WO | 2016014535 A1 | 1/2016 |
| WO | 2016073845 | 5/2016 |
| WO | 2017019957 A2 | 2/2017 |
| WO | 2018015340 | 1/2018 |
| WO | 2018187799 A1 | 10/2018 |
| WO | 2018223002 | 12/2018 |

(Continued)

OTHER PUBLICATIONS

Winkler et al. Journal of Immunology (2000) 165(8): 4505-4514 (Year: 2000).*
Schroeder and Cavacini. Journal of Allergy and Clinical Immunology (2010) 125(2, Suppl.2): S41-S52 (Year: 2010).*
Sela-Culang et al. Frontiers in Immunology (2013) 4: 302 (Year: 2013).*
Lim. Pharmacology and Therapeutics (2020) 212: 107582 (Year: 2020).*
Badri H. et al., Optimization of radiation dosing schedules for proneural glioblastoma, J Math Bio, 2016, vol. 72, N. 5, pp. 1301-1336.
Baylot V. et al., TCTP Has a Crucial Role in the Different Stages of Prostate Cancer Malignant Progression, Results Probl Cell Differ, 2017, vol. 64, pp. 255-261.

(Continued)

*Primary Examiner* — Brad Duffy
*Assistant Examiner* — Elizabeth A Shupe
(74) *Attorney, Agent, or Firm* — Ice Miller LLP

(57) ABSTRACT

Anti-Vβ17/anti-CD123 bispecific antibodies or antigen-binding fragments thereof are described. Also described are nucleic acids encoding the antibodies, compositions comprising the antibodies, methods of producing the antibodies, and methods of using the antibodies.

25 Claims, 12 Drawing Sheets
Specification includes a Sequence Listing.

(56) References Cited

FOREIGN PATENT DOCUMENTS

| WO | 2019091384 |  | 5/2019 |
| WO | 2019246286 | A1 | 12/2019 |
| WO | 2020010250 |  | 1/2020 |
| WO | 2020142672 |  | 7/2020 |
| WO | 2020183245 | A2 | 9/2020 |
| WO | 2020257760 | A1 | 12/2020 |
| WO | 2021064671 | A1 | 4/2021 |
| WO | 2021173896 | A1 | 9/2021 |
| WO | 2022056197 |  | 3/2022 |

OTHER PUBLICATIONS

Qi Pan, et al. "Blocking Neuropilin-1 Function Has an Additive Effect with Anti-VEGF to Inhibit Tumor Growth", Cancer Cell Jan. 11, 2007, pp. 53-67.

Lin et al. (African Journal of Biotechnology, 10(79): 18294-18302, 2011) (Year: 2011).

McCarthy et al. (J. Immunol. Methods, 251(1-2): 137-149, 2001) (Year: 2001).

Garfall & June, Three is a charm for an antibody to fight cancer, 2019, Nature, vol. 575, pp. 450-451 (Year: 2019).

Al-Lazikani et al., "Standard conformations for the canonical structures of immunoglobulins", J. Mol. Biol. 273:927-948 (1997).

Atwell et al. "Stable Heterodimers from Remodeling the Domain Interface of a Homodimer using a Phage Display Library," Journal of Molecular Biology, vol. 270, 1997, 26-35.

Brown et al., "A Study of the Interactions Between an IgG-Binding Domain Based on the B Domain of staphylococcal Protein A and Rabbit IgG", Mol. Biotech. 10:9-16, 1998.

Ferrara et al., "Modulation of Therapeutic Antibody Effector Functions by Glycosylation Engineering: Influence of Golgi Enzyme Localization Domain and Co-Expression of Heterolgous B1, 4-N-acetylglucosaminyltransferase III and Golgi m-mannodsidase II", Biotechnol Bioeng 93:851-861, 2006.

Ferrara et al., "The carbohydrate at FCYRIIIa Asn-162; An element required for high affinity binding to non-fucosylated IgG glycoforms", J Biol Chem 281:5032-5036, 2006.

Fransson J, et al. "Human framework adaptation of a mouse anti-human IL-13 antibody", J. Mol. Biol. 2010; 398:214-231.

Kabat et al., "Unusual distributions of amino acids in complementarity-determining (hypervariable) segments of heavy and light chains of immunoglobulins and their possible roles in specificity of antibody-combining sites", J. Biol. Chem. 252:6609-6616 (1977).

Kabat, Elivin A. "The Structural Basis of Antibody Complementarity," Adv. Prot. Chem. 32:1-75 (1978).

Kawasaki et al., "Presence of four major haplotypes in human BCMA gene: lack of association with systemic lupus erythematosus and rheumatoid arthritis", Genes Immun. 2:276-9, 2001.

Konno et al., "Fucose content of monoclonal antibodies can be controlled by culture medium osmolality for high antibody-dependent cellular cytotoxicity", Cytotechnology 64:249-65, 2012.

Lefranc et al., "IMGT unique numbering for immunoglobulin and T cell receptor variable domains and Ig superfamily V-like domains", Dev. Comp. Immunol. 27(1):55-77 (2003).

Morea et al., "Antibody Modeling: Implications for Engineering and Design," Methods, vol. 20, 2000; pp. 267-279.

Mori et al., "Engineering Chinese hamster ovary cells to maximize effector function of produced antibodies using FUT8 siRNA", Biotechnol Bioeng 88:901-908, 2004.

Olivier et al., "EB66 cell line, a duck embryonic stem cell-derived substrate for the industrial production of therapeutic monoclonal antibodies with enhanced ADCC activity", MAbs; 2(4), 2010.

Osborn, et al., "High-Affinity IgG antibodies develop naturally in Ig-knockout rats carrying germline human lgH/lgk/lgy loci bearing the rat CH region", J Immunol, 2013, 190(4): 1481-90.

Shields et al., "Lack of fucose on human IgG1 N-Linked oligosaccharide improves binding to human FCYRIII and antibody-dependent cellular toxicity", J Biol Chem 277:26733-26740, 2002.

Shinkawa et al., "The absence of fucose but not the presence of galactose or bisection N-Acetylglucosamine of human IgG1 complex-type oligosaccharides shows the critical role of enhancing antibody-dependent cellular cytotoxicity", J Biol Chem 278:3466-3473, 2003.

Zhou et al., "Development of a simple and rapid method for producing non-fucosylated oligomannose containing antibodies with increased effector function", Biotechnol Bioeng 99:652-65, 2008.

Anonymous: Conjugated Antibody Anti-TCR V[beta]17-PE (2019).

* cited by examiner

| Donor | HLA status | % of Vβ17+ in CD8 T cells (Day 0) | % of Vβ17+ in CD8 T cells (Day 14) |
|---|---|---|---|
| HPU-03033 | A2 | 5.45 | 14.4 |
| HPU-07540 | A2 | 3.70 | 34.4 |
| HPU-08694 | A2 | 3.88 | 75 |
| 17043595 | A*0201 | 2 | 15 |
| 14035473 | A*0201 | 2.8 | 40.7 |
| 15036948 | A*0201 | 3.64 | 43.0 |

FIG. 2B

ANTI-Vβ17/ANTI-CD123 BISPECIFIC ANTIBODIES

CROSS REFERENCE TO RELATED APPLICATIONS

This application is a U.S. National Stage Application under 35 U.S.C. § 371 of International Patent Application No. PCT/IB2020/000342, filed March 11, 202, which claims the benefit of U.S. Provisional Application No. 62/816,464, filed on Mar. 11, 2019, the disclosure of each of which is incorporated by reference in its entirety.

FIELD OF THE INVENTION

This invention relates to monoclonal anti-Vβ17/anti-CD123 bispecific antibodies, nucleic acids and expression vectors encoding the antibodies, recombinant cells containing the vectors, and compositions comprising the antibodies. Methods of making the antibodies, and methods of using the antibodies to kill cancer cells, are also provided.

REFERENCE TO SEQUENCE LISTING SUBMITTED ELECTRONICALLY

This application incorporates by reference in its entirety the Computer Readable Form ("CRF") of a Sequence Listing in ASCII text format submitted via EFS-Web. The Sequence Listing text file submitted via EFS-Web is entitled "14620-006-999_SL.txt," was created on Sep. 5, 2021, and is 87,587 bytes in size.

BACKGROUND OF THE INVENTION

Cytotoxic T cells (e.g., CD8+ T cells) can be utilized to directly kill cancer cells. Finding a way to direct cytotoxic T cells to a cancer cell could lead to the killing of such cells and an inhibition of cancer cell propagation. It has been demonstrated that cytotoxic T cells can be activated against cancer cells expressing cancer-associated antigens, by bring said cytotoxic T cells into close proximity to the cancer cells for an extended period of time using a bispecific antibody that binds both the cytotoxic T cell and the cancer cell. A variety of potential complications to this approach of killing cancer cells exist, such as selecting T cell and cancer cell antigens that mediate T cell activation, selecting parental antibodies that will have adequate affinity to mediate binding in the context of a bispecific antibody, and choosing a cancer cell antigen that will activate T cells to act specifically against cancer cells, rather than elicit nonspecific T cell activation. These complications are only compounded in the context of attempting to activate T cells to destroy cancer cells in an animal subject.

BRIEF SUMMARY OF THE INVENTION

Provided herein are bispecific antibodies capable of binding Vβ17, an antigen associated with T cells, and CD123, an antigen associated with cancer cells. Cytotoxic T cells express T cell receptors that consist of α- and β-chains, such as Vβ17. It is hypothesized that a bispecific antibody binding to Vβ17 and a cancer-associated antigen, such as CD123, may direct a cytotoxic T cell to an antigen-expressing cancer cell. Utilizing a bispecific antibody of this sort to recruit, or redirect, the cytotoxic T cell to an antigen-expressing cancer cell and could allow the T cell to kill the cancer cell.

In one general aspect, the present disclosure relates to isolated bispecific antibodies or antigen-binding fragments thereof that bind to Vβ17 and CD123.

Provided herein are isolated Vβ17 bispecific antibodies or antigen-binding fragments thereof. The isolated Vβ17 bispecific antibody or antigen-binding fragment thereof comprises:
  a. a first heavy chain (HC1);
  b. a second heavy chain (HC2);
  c. a first light chain (LC1); and
  d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In certain embodiments, the binding site for the first antigen binds to a Vβ17 on the surface of a CD8+ or CD4+ T cell. In certain embodiments, the binding site for the second antigen binds to a tumor antigen present on the surface of a cancer cell.

In certain embodiments, the binding of the bispecific antibody to Vβ17 present on the surface of the CD8+ or CD4+ T cell and the binding of the tumor antigen present on the surface of the cancer cells results in the killing of the cancer cell.

In certain embodiments, HC2 and LC2 bind to CD123.

In certain embodiments, the bispecific antibody or antigen-binding fragment thereof is an IgG isotype, such as IgG4.

In certain embodiments, the bispecific antibody or antigen-binding fragment thereof induces CD8+ or CD4+ T-cell dependent cytotoxicity of a cancer cell in vitro with an $EC_{50}$ of less than about 0.2 pM.

Also provided are isolated anti-Vβ17/anti-CD123 bispecific antibodies or antigen-binding fragments thereof. The anti-Vβ17/anti-CD123 bispecific antibodies or antigen-binding fragments thereof comprise:
  a. a first heavy chain (HC1);
  b. a second heavy chain (HC2)
  c. a first light chain (LC1); and
  d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen that specifically binds Vβ17, and wherein HC2 comprises a heavy chain complementarity determining region 1 (HCDR1), HCDR2, and HCDR3 comprising the amino acid sequences of SEQ ID NO:34, SEQ ID NO:35, and SEQ ID NO:36, respectively, and LC2 comprises a light chain complementarity determining region 1 (LCDR1), LCDR2, and LCDR3 comprising the amino acid sequences of SEQ ID NO:37, SEQ ID NO:38, and SEQ ID NO:39, respectively, to form a biding site for a second antigen that specifically binds CD123. In certain embodiments, the HC1 comprises the amino acid sequence of SEQ ID NO:13 and LC1 comprises the amino acid sequence of SEQ ID NO:14, and the HC2 comprises the amino acid sequence of SEQ ID NO:15 and LC2 comprises the amino acid sequence of SEQ ID NO:16. In certain embodiments, the Vβ17 is on the surface of a CD8+ or CD4+ T cell. In certain embodiments, the CD123 is on the surface of a cancer cell. In certain embodiments, the bispecific antibody or antigen-binding fragment thereof induces CD8+ or CD4+ T-cell dependent cytotoxicity of a cancer cell in vitro with an EC50 of less than about 0.2 pM.

In certain embodiments, the anti-Vβ17/anti-CD123 bispecific antibodies or antigen-binding fragments thereof are chimeric, partially humanized, or fully humanized.

Also provided are isolated humanized Vβ17 monoclonal antibodies or antigen-binding fragments thereof. The isolated humanized Vβ17 monoclonal antibody or antigen-binding fragment thereof can comprise an amino acid sequence with at least 95% identity to the amino acid sequence of SEQ ID NO:28. In certain embodiments, the isolated humanized Vβ17 monoclonal antibody or antigen-binding fragment thereof comprises an amino acid sequence of SEQ ID NO:28.

Also provided are isolated nucleic acids encoding the monoclonal antibodies or antigen-binding fragments thereof and the bispecific antibodies or antigen-binding fragments thereof disclosed herein.

Also provided are vectors comprising the isolated nucleic acids encoding the monoclonal antibodies or antigen-binding fragments thereof and the bispecific antibodies or antigen-binding fragments thereof disclosed herein.

Also provided are host cells comprising the vectors comprising the isolated nucleic acids disclosed herein.

Also provided are methods of directing a Vβ17-expressing CD8+ or CD4+ T cell to a cancer cell. The methods comprise contacting a Vβ17-expressing CD8+ or CD4+ T cell with a anti-Vβ17/anti-CD123 bispecific antibodies or antigen-binding fragments thereof disclosed herein. Contacting the Vβ17-expressing CD8+ or CD4+ T cell with the anti-Vβ17/anti-CD123 bispecific antibodies or antigen-binding fragments thereof can direct the Vβ17-expressing CD8+ or CD4+ T cell to a cancer cell.

Also provided are methods for inhibiting growth or proliferation of cancer cells. The methods comprise contacting the cancer cells with the bispecific antibodies disclosed herein. Contacting the cancer cells with the described antibodies can, for example, inhibit the growth or proliferation of the cancer cells, or promote T cell mediated killing of the cancer cells.

Also provided are methods of producing the bispecific antibodies or antigen-binding fragments thereof disclosed herein. The methods comprise culturing a cell comprising a nucleic acid encoding one heavy and light chain pair of the bispecific antibody under conditions to produce the heavy and light chains or an antigen-binding fragment thereof, and recovering the heavy and light chains of the bispecific antibody or an antigen-binding fragment thereof from the cell or culture. Following collection of heavy and light chains for both arms of the bispecific antibody, the heavy and light chain pairs are mixed in conditions suitable to allow for self-assembly, after which the self-assembled bispecific antibodies are collected.

Also provided are methods of producing compositions comprising the bispecific antibodies or antigen-binding fragments disclosed herein, such as buffered compositions or purified compositions and the like. For example, the methods may comprise combining the bispecific antibody or antigen-binding fragment thereof with a buffer acceptable that is acceptable for storage and use of the bispecific antibody.

Also provided are kits comprising bispecific antibodies or antigen-binding fragments thereof disclosed herein and packaging for the same.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIGS. 2A-2B shows that Vβ17+CD8+ T cells exist in healthy subjects and upon culture with M1 peptide these cells can be expanded in vitro. FIG. 2A shows FACS histograms of gated peripheral blood mononuclear cells (PBMCs) for CD8+ T cells expressing Vβ17 (Vβ17+) on the cells surface from healthy subjects. FIG. 2B shows HLA sub-type of various donors and presence of percent Vβ17+ CD8+ T cells identified as day 0, and after in vitro expansion with M1 peptide for 14 days (Day 14).

FIG. 7A shows FACS histograms of gated PBMCs for CD8+ T cells expressing Vβ17 (Vβ17+) on the cell surface from healthy subjects (left graph, Vβ17 non-depleted) and from PBMCs that were depleted of Vβ17+ T cells using negative selection (right graph, Vβ17 depleted). FIG. 7B shows specific binding of an anti-Vβ17/anti-CD123 bispecific antibody (VB11) and a Vβ17 null bispecific antibody (VB13) to CD8+ T cells from FIG. 7A. A dose response of bispecific antibodies is shown in the figure. The table below the graph shows EC$_{50}$ values for binding calculated from the above graph given in nM.

FIG. 9A shows FACS plots of Vβ17+ and Vβ17− gated CD8+ T cells. When T cells were activated with Vβ17 bispecific antibody there was high level of upregulation of CD69 (62.5%) on Vβ17+ as compared to Vβ17− CD8+ T cells (1.80%). FIG. 9B shows a bar graph for upregulation of CD69 on Vβ17+ and Vβ17− gated CD8+ T cells when activated using Vβ17 bispecific antibody.

DETAILED DESCRIPTION OF THE INVENTION

Figure 1:
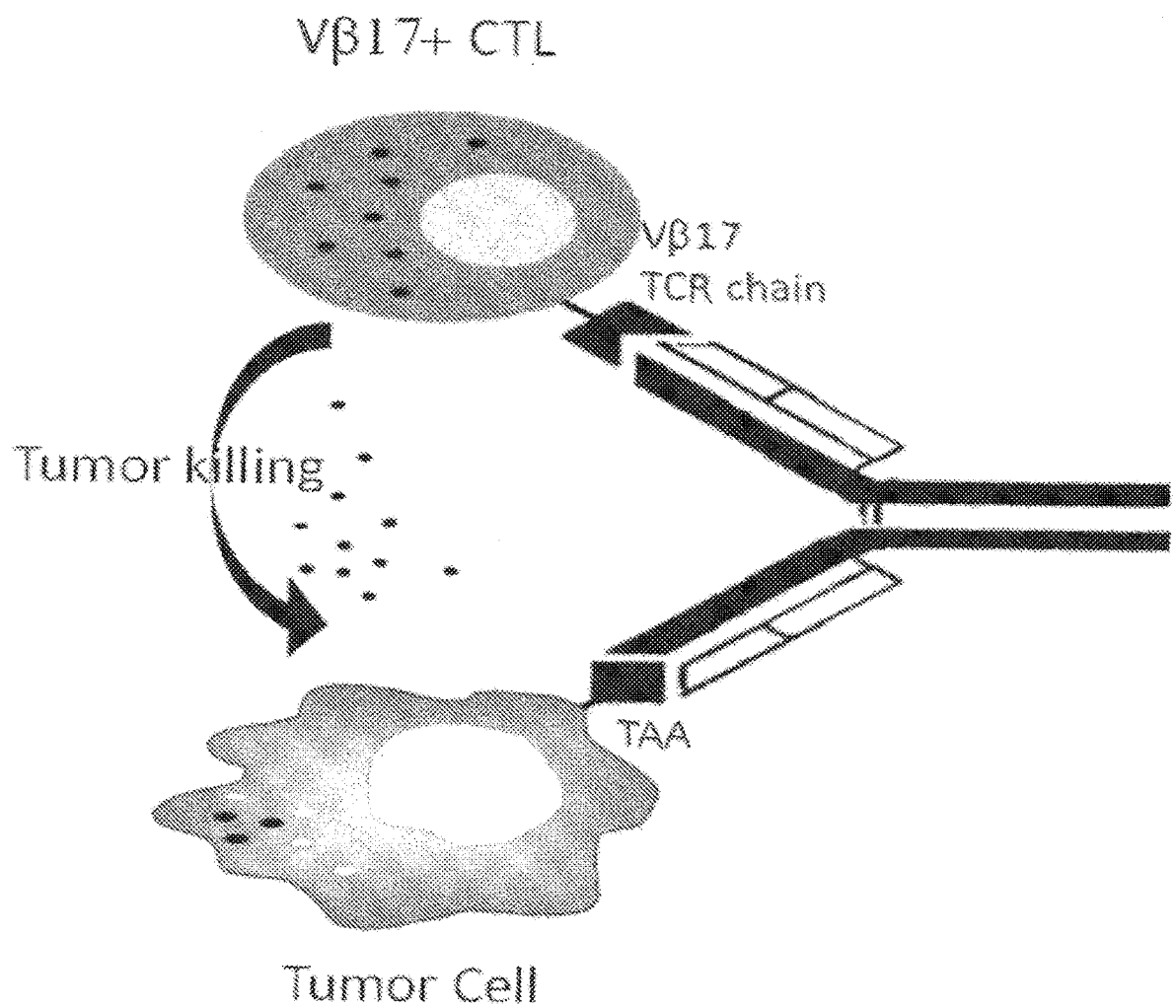
FIG. 1 shows a schematic demonstrating the binding of an anti-Vβ17/anti-tumor antigen bispecific antibody to recruit T-cells to a cancer cell and to induce cancer cell death.
Figure 2A:
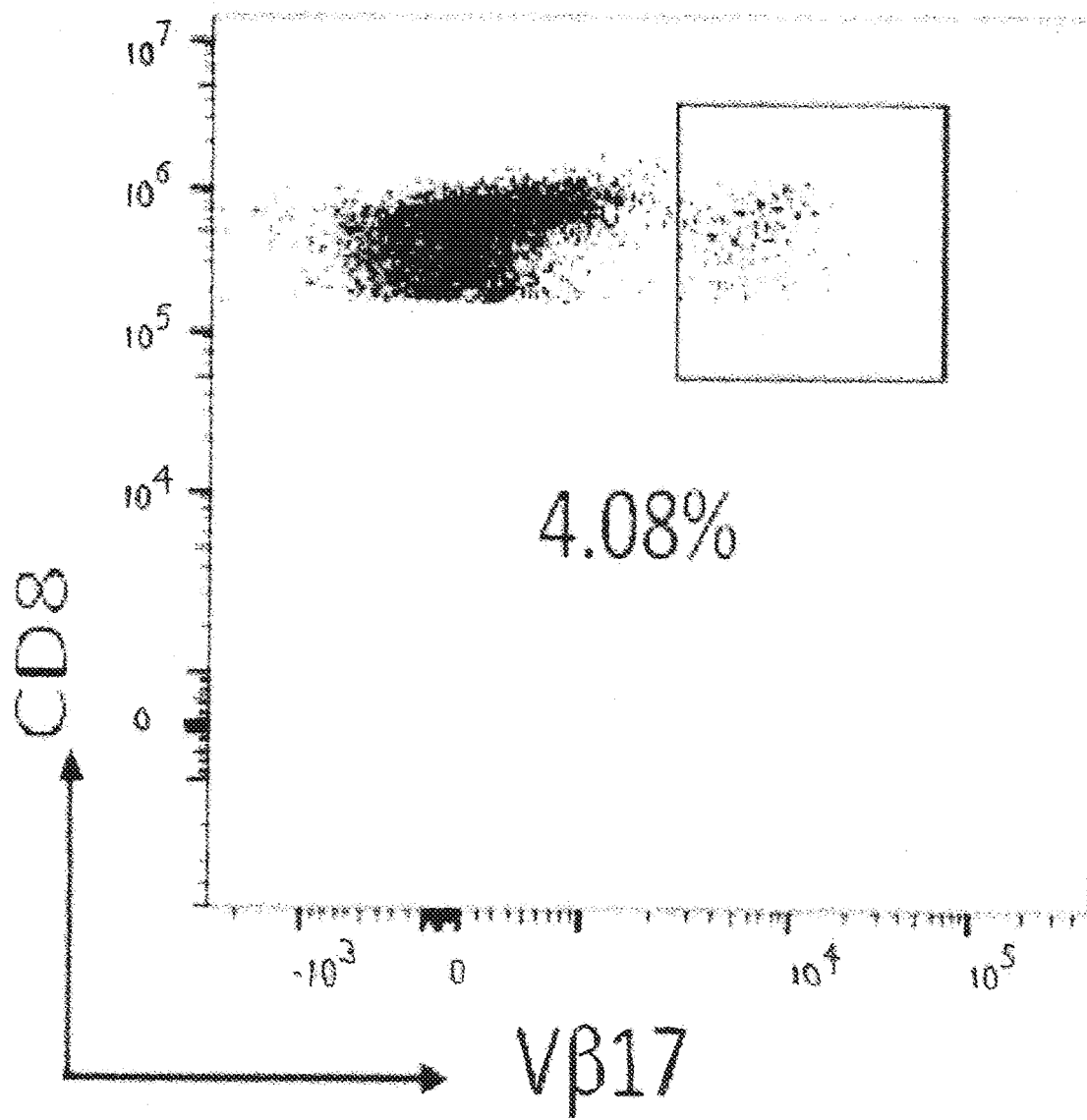

Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

It must be noted that as used herein and in the appended claims, the singular forms "a," "an," and "the" include plural reference unless the context clearly dictates otherwise.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-Vβ17/anti-CD123 bispecific antibodies and polynucleotides that encode them, Vβ17 polypeptides and Vβ17 polynucleotides that encode them, CD123 polypeptides and CD123 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol.*

Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

Described herein are isolated anti-Vβ17 bispecific antibodies or antigen-binding fragments thereof, nucleic acids and expression vectors encoding the antibodies, recombinant cells containing the vectors, and compositions comprising the antibodies. The invention additionally relates to isolated anti-Vβ17/anti-CD123 bispecific antibodies or antigen-binding fragments thereof, nucleic acids and expression vectors encoding the antibodies, recombinant cells containing the vectors, and compositions comprising the bispecific antibodies. Methods of making the antibodies, and methods of using the antibodies to treat diseases, including cancer, are also provided. The antibodies disclosed herein possess one or more desirable functional properties, including but not limited to high-affinity binding to Vβ17 and/or CD123, high specificity to Vβ17 and/or CD123, and the ability to treat or prevent cancer when administered alone or in combination with other anti-cancer therapies.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies disclosed herein include heavy and/or light chain constant regions from mouse or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to Vβ17 is substantially free of antibodies that do not bind to Vβ17; an isolated antibody that specifically binds to CD123 is substantially free of antibodies that do not bind to CD123). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies disclosed herein can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin heavy and light chain pair which has binding specificity for a first epitope (e.g., an epitope on a Vβ17 antigen) and a second immunoglobulin heavy and light chain pair that has binding specificity for a second epitope (e.g., an epitope on a CD123 antigen). In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on Vβ17 and the second epitope is located on CD123. In an embodiment, the first epitope is located on Vβ17 and the second epitope is located on PD-1, PD-L1, CTLA-4, EGFR, HER-2, CD19, CD20, CD3 and/or other tumor associated immune suppressors or surface antigens.

The term "half antibody" as used herein refers to one immunoglobulin heavy chain associated with one immunoglobulin light chain. An exemplary half-antibody is depicted in SEQ ID NO: 28. One skilled in the art will readily appreciate that a half-antibody can encompass a fragment thereof and can also have an antigen binding domain consisting of a single variable domain, e.g., originating from a camelidae.

As used herein, the term "Vβ17" refers to a T cell receptor, which is expressed in response to an immune response on a cytotoxic T cell. Vβ17-expressing CD8+ T cells are commonly produced in response to influenza A virus exposure in a subject. Vβ17-expressing CD8+ T cells provide great recall in response to influenza exposure in the subject. The term "Vβ17" includes any Vβ17 variant, isoform, and species homolog, which is naturally expressed by cells (including T cells) or can be expressed on cells transfected with genes or cDNA encoding the polypeptide. Unless noted, preferably the Vβ17 is a human Vβ17. A human Vβ17 amino acid sequence is provided by GenBank Accession Number AAB49730.1.

The term "CD123" refers to a molecule that is found on cells which helps transmit the signal of interleukin-3, a soluble cytokine that is important in the immune system. CD123 can also be referred to as the "interleukin-3 receptor." The receptor belongs to the type I cytokine receptor family and is a heterodimer with a unique alpha chain paired with the common beta subunit (beta c or CD131). The CD123 receptor can be found on pluripotent progenitor cells and can induce tyrosine phosphorylation within the cell and promote proliferation and differentiation within hematopoietic cell lines. CD123 can also be expressed in acute myeloid leukemia (AML) subtypes. The term "CD123" includes any CD123 variant, isoform, and species homolog, which is naturally expressed by cells (including T cells) or can be expressed on cells transfected with genes or cDNA encoding those polypeptides, unless noted, preferably the "CD123" is a human CD123. A human CD123 amino acid sequence is provided by GenBank Accession Number AY789109.1.

As used herein, an antibody that "specifically binds to Vβ17" refers to an antibody that binds to a Vβ17, preferably a human Vβ17, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet® RED96 system.

As used herein, an antibody that "specifically binds to CD123" refers to an antibody that binds to a CD123, preferably a human CD123, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka)

and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet® RED96 system.

The smaller the value of the KD of an antibody, the higher affinity that the antibody binds to a target antigen.

According to a particular aspect, the invention relates to an isolated Vβ17 bispecific antibody or antigen-binding fragment thereof comprising (a) a first heavy chain (HC1); (b) a second heavy chain (HC2); (c) a first light chain (LC1); and (d) a second light chain (LC2). The HC1 can be associated with the LC1 and the HC2 can be associated with LC2. The HC1 can comprise a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 can comprise a light chain complementarity determining region 1 (LCDR1), LCDR2, and LCDR3 comprising the amino acid sequences of SEQ ID NO:4, SEQ ID NO:5, and SEQ ID NO:6, respectively.

The HC1 and LC1 form a binding site for a first antigen, and the HC2 and LC2 form a binding site for a second antigen. By way of an example, the binding site for the first antigen can bind to a Vβ17 on a CD8+ or CD4+ T cell, and the binding site for the second antigen can, for example, bind a tumor antigen present on the surface of a cancer cell. The binding of the Vβ17 bispecific antibody to Vβ17 present on the surface of the CD8+ or CD4+ T cell, and the binding of the tumor antigen present on the surface of the cancer cells can, for example, result in the killing of the cancer cell.

Also provided herein are anti-Vβ17/anti-CD123 bispecific antibodies or antigen-binding fragments thereof comprising an anti-Vβ17 antibody or an antigen-binding fragment thereof and an anti-CD123 antibody or antigen-binding fragment thereof. In certain embodiments the anti-Vβ17/anti-CD123 bispecific antibody or antigen-binding fragment thereof comprises (a) a first heavy chain (HC1); (b) a second heavy chain (HC2); (c) a first light chain (LC1); and a second light chain (LC2). The HC1 is associated with the LC1 and the HC2 is associated with the LC2. In certain embodiments, the HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively. In certain embodiments, the HC2 comprises a heavy chain complementarity determining region 1 (HCDR1), HCDR2, and HCDR3 comprising the amino acid sequences of SEQ ID NO:34, SEQ ID NO:35, and SEQ ID NO:36, respectively, and LC2 comprises a light chain complementarity determining region 1 (LCDR1), LCDR2, and LCDR3 comprising the amino acid sequences of SEQ ID NO:37, SEQ ID NO:38, and SEQ ID NO:39, respectively In certain embodiments, the HC1 can, for example, comprise an amino acid sequence of SEQ ID NO:13 and the LC1 can, for example, comprise an amino acid sequence of SEQ ID NO:14 to form a binding site for a first antigen that specifically binds Vβ17. The HC2 can, for example, comprise an amino acid sequence of SEQ ID NO:15 and the LC2 can, for example, comprise an amino acid sequence of SEQ ID NO: 16 to form a binding site for a second antigen that specifically binds CD123.

In certain embodiments, the Vβ17 is on the surface of a CD8+ or CD4+ T cell. In certain embodiments, the CD123 is on the surface of a cancer cell (e.g., a leukemia cell).

In some embodiments, the bispecific antibodies disclosed herein can take the form of a diabody, a cross-body, or a bispecific antibody obtained via a controlled Fab arm exchange as described herein.

In some embodiments, the bispecific antibodies include IgG-like molecules with complementary CH3 domains that promote heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab®/Quadroma (Trion Pharma/Fresenius Biotech), the Knobs-into-Holes (Genentech), CrossMAbs® (Roche) and the electrostatically-matched (Amgen), the LUZ-Y (Genentech), the Strand Exchange Engineered Domain body (SEEDbody) (EMD Serono), the Biclonic® (Merus) and the DuoBody® (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX®-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules can include ScFv/Fc Fusions (Academic Institution), SCORPION® (Emergent BioSolutions/Trubion, Zymogenetics/BMS), Dual Affinity Retargeting Technology (Fc-DART®) (MacroGenics) and Dual(ScFv)₂-Fab (National Research Center for Antibody Medicine—China).

In some embodiments, Fab fusion bispecific antibodies include F(ab)₂ (Medarex/AMGEN), Dual-Action or Bis-Fab (Genentech), Dock-and-Lock (DNL®) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE®) (Micromet), Tandem Diabody (Tandab®) (Affimed), Dual Affinity Retargeting Technology (DART®) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting Nanobodies® (Ablynx), dual targeting heavy chain only domain antibodies.

Full length bispecific antibodies disclosed herein can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms can be engineered to favor heterodimerization over homodimerization. The resulting product is a bispecific antibody having two Fab arms or half molecules, each binding a distinct epitope, i.e. an epitope on Vβ17 and an epitope on a tumor antigen.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface can be used, as described in US Pat. Publ. No. US2010/0015133; US Pat. Publ. No. US2009/0182127; US Pat. Publ. No. US2010/028637; or US Pat. Publ. No. US2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, bispecific antibodies disclosed herein can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in International Pat. Publ. No. WO2011/131746. In the methods, the first monospecific bivalent antibody (e.g., anti-CD33 antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that may be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In certain embodiments, the anti-Vβ17 antibody or antigen-binding fragment thereof comprises a heavy chain complementarity determining region 1 (HCDR1), HCDR2, HCDR3, a light chain complementarity determining region 1 (LCDR1), LCDR2, and LCDR3, having the polypeptide sequence of:

a. SEQ ID NOs:1, 2, 3, 4, 5, and 6, respectively;
and the anti-CD123 antibody or antigen-binding fragment thereof comprises a heavy chain complementarity determining region 1 (HCDR1), HCDR2, HCDR3, a light chain complementarity determining region 1 (LCDR1), LCDR2, and LCDR3, having the polypeptide sequence of:

1. SEQ ID NOs:34, 35, 36, 37, 38, and 39, respectively.

According to another particular aspect, the invention relates to an isolated anti-Vβ17/anti-CD123 bispecific antibody or antigen-binding fragment thereof that induces antibody-dependent cell-mediated cytotoxicity (ADCC). The bispecific antibody or antigen-binding fragment thereof can, for example, induce ADCC in vitro. The bispecific antibody or antigen-binding fragment thereof can induce ADCC with an $EC_{50}$ of less than about 1 pM. In certain embodiments, the $EC_{50}$ is less than about 1 pM, less than about 0.9 pM, less than about 0.8 pM, less than about 0.7 pM, less than about 0.6 pM, less than about 0.5 pM, less than about 0.4 pM, less than about 0.300 pM, less than about 0.2 pM, less than about 0.19 pM, less than about 0.18 pM, less than about 0.17 pM, less than about 0.16 pM, less than about 0.15 pM, less than about 0.14 pM, less than about 0.13 pM, less than about 0.12 pM, less than about 0.11 pM, less than about 0.1 pM, less than about 0.09 pM, less than about 0.08 pM, less than about 0.07 pM, less than about 0.06 pM, less than about 0.05 pM, less than about 0.04 pM, less than about 0.03 pM, less than about 0.02 pM, or less than about 0.01 pM. In certain embodiments, the anti-Vβ17/anti-CD123 bispecific antibody or antigen-binding fragment thereof comprises an IgG1, IgG2, IgG3, or IgG4 backbone. In one such embodiment, the anti-Vβ17/anti-CD123 bispecific antibody or antigen-binding fragment thereof has an antibody backbone of the IgG4 isotype.

In some embodiments described herein, immune effector properties of the anti-Vβ17/anti-CD123 bispecific antibodies can be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen-binding or CDC activity. Such Abs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α-1,6-fucosyltrasferase (FUT8) gene (Mori et al., Biotechnol Bioeng 88:901-908, 2004), or coexpression of β-1,4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the anti-Vβ17/anti-CD123 bispecific antibodies can also be enhanced by certain substitutions in the antibody Fc. Exemplary substitutions include, for example, substitutions at amino acid positions 256, 290, 298, 312, 356, 330, 333, 334, 360, 378 or 430 (residue numbering according to the EU index) as described in U.S. Pat. No. 6,737,056.

According to another particular aspect, the invention relates to an isolated anti-Vβ17/anti-CD123 bispecific antibody or antigen-binding fragment thereof capable of inducing T-cell dependent cytotoxicity in Vβ17-expressing cells and/or CD123-expressing cells. The bispecific antibody or antigen-binding fragment thereof can, for example, induce T-cell dependent cytotoxicity in Vβ17-expressing cells and/or CD123-expressing cells in vitro with an $EC_{50}$ value of less than about 2 nM. In certain embodiments, the $EC_{50}$ is less than about 2.0 nM, less than about 1.9 nM, less than about 1.8 nM, less than about 1.7 nM, less than about 1.6 nM, less than about 1.5 nM, less than about 1.4 nM, less than about 1.3 nM, less than about 1.2 nM, less than about 1.1 nM, less than about 1.0 nM, less than about 0.9 nM, less than about 0.8 nM, less than about 0.7 nM, less than about 0.6 nM, less than about 0.5 nM, less than about 0.4 nM, less than about 0.3 nM, less than about 0.2 nM, and less than about 0.1 nM.

According to another particular aspect, the invention relates to an isolated anti-Vβ317/anti-CD123 bispecific antibody or antigen-binding fragment thereof, wherein the anti-Vβ317/anti-CD123 bispecific antibody or antigen-binding fragment thereof is chimeric.

According to another particular aspect, the invention relates to an isolated anti-Vβ317/anti-CD123 bispecific antibody or antigen-binding fragment thereof, wherein the anti-Vβ317/anti-CD123 bispecific antibody or antigen-binding fragment thereof is human or humanized.

In another general aspect, the invention relates to an isolated humanized Vβ17 monoclonal antibody or antigen-binding fragment thereof. The isolated humanized Vβ317 monoclonal antibody or antigen-binding fragment thereof comprises an amino acid sequence with at least 85%, preferably 90%, more preferably 95% or more, such as 95%, 96%, 97%, 98%, or 99% identity to the amino acid sequence of SEQ ID NO:28. In certain embodiments, the humanized Vβ17 monoclonal antibody or antigen-binding fragment thereof comprises the amino acid sequence of SEQ ID NO:28.

In another general aspect, the invention relates to isolated nucleic acids encoding the monoclonal antibodies or antigen-binding fragments thereof disclosed herein. In another general aspect, the invention relates to isolated nucleic acids encoding the bispecific antibodies or antigen-binding fragments thereof disclosed herein. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies and/or bispecific antibodies disclosed herein can be altered without changing the amino acid sequences of the proteins.

In another general aspect, the invention relates to vectors comprising the isolated nucleic acids disclosed herein. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments disclosed herein. Such techniques are well known to those skilled in the art in view of the present disclosure.

In another general aspect, the invention relates to host cells comprising the isolated nucleic acids encoding the monoclonal antibodies and/or bispecific antibodies or antigen-binding fragments thereof disclosed herein. Any host cell known to those skilled in the art in view of the present disclosure can be used for recombinant expression of antibodies or antigen-binding fragments thereof disclosed herein. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a bispecific antibody or antigen-binding fragment thereof disclosed herein. The methods comprise culturing a cell comprising a nucleic acid encoding the bispecific antibody or antigen-binding fragment thereof under conditions to produce a bispecific antibody or antigen-binding fragment thereof disclosed herein, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Methods of Use

In another general aspect, the invention relates to a method of targeting CD123 on the surface of a cancer cell, the method comprising exposing the cancer cell to an anti-Vβ17/anti-CD123 bispecific antibody or antigen-binding fragment thereof.

The functional activity of bispecific antibodies and antigen-binding fragments thereof that bind Vβ17 and/or CD123 can be characterized by methods known in the art and as described herein. Methods for characterizing antibodies and antigen-binding fragments thereof that bind Vβ17 and/or CD123 include, but are not limited to, affinity and specificity assays including Biacore®, ELISA, and OctetRed® analysis; binding assays to detect the binding of antibodies to CD123 on cancer cells by FACS; binding assays to detect the binding of antibodies to Vβ17 on CD8+ or CD4+ T cells. According to particular embodiments, the methods for characterizing antibodies and antigen-binding fragments thereof that bind Vβ17 and/or CD123 include those described below.

In another general aspect, the invention relates to a method of directing Vβ17-expressing CD8+ or CD4+ T cells to a cancer cell. The methods comprise contacting the Vβ17-expressing CD8+ or CD4+ T cell with a anti-Vβ17/anti-CD123 bispecific antibody or antigen-binding fragment thereof, wherein the antibody or antibody fragment directs the Vβ17-expressing CD8+ or CD4+ T cell to a cancer cell having CD123 on its surface.

In another general aspect, the invention relates to a method for inhibiting growth or proliferation of cancer cells. The methods comprise contacting the Vβ17-expressing CD8+ T cells with a anti-Vβ17/anti-CD123 bispecific antibody or antigen-binding fragment thereof, wherein contacting the cancer cells with the antibody or antibody fragment inhibits the growth or proliferation of the cancer cells.

According to embodiments of the invention, the described anti-Vβ17/anti-CD123 bispecific antibody or antigen-binding fragment thereof can be provided in a buffered composition for storage or use. Suitable buffers for the storage of the described anti-Vβ17/anti-CD123 bispecific antibody or antigen-binding fragment thereof would serve to maintain the stability of the antibody or antibody fragment by minimizing deterioration while stored, not promoting aggregation of the antibody or antibody fragment, or minimizing adhesion to the storage vessel.

Embodiments

This invention provides the following non-limiting embodiments.

Embodiment 1 is an isolated Vβ17 bispecific antibody or antigen-binding fragment thereof, the isolated Vβ17 bispecific antibody or antigen-binding fragment thereof comprising:
 a. a first heavy chain (HC1);
 b. a second heavy chain (HC2);
 c. a first light chain (LC1); and
 d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen.

Embodiment 2 is the Vβ17 bispecific antibody or antigen-binding fragment thereof of embodiment 1, wherein the binding site for the first antigen binds to Vβ17 on a CD8+ or CD4+ T cell.

Embodiment 3 is the Vβ17 bispecific antibody or antigen-binding fragment thereof of embodiment 1 or 2, wherein the binding site for the second antigen binds to a tumor antigen present on the surface of a cancer cell.

Embodiment 4 is the Vβ17 bispecific antibody or antigen-binding fragment of any one of embodiments 1 to 3, wherein HC1 and LC1 are humanized.

Embodiment 5 is the Vβ17 bispecific antibody or antigen-binding fragment thereof of any one of embodiments 1 to 4, wherein HC2 and LC2 bind to CD123.

Embodiment 6 is the Vβ17 bispecific antibody or antigen-binding fragment thereof of any one of embodiments 1 to 5, wherein the bispecific antibody or antigen-binding fragment thereof is a IgG isotype.

Embodiment 7 is the Vβ17 bispecific antibody or antigen-binding fragment thereof of any one of embodiments 1 to 6, wherein the bispecific antibody or antigen-binding fragment thereof is a IgG4 isotype.

Embodiment 8 is the Vβ17 bispecific antibody or antigen-binding fragment thereof of any one of embodiments 1 to 7, wherein the bispecific antibody or antigen-binding fragment thereof induces CD8+ or CD4+ T-cell dependent cytotoxicity of a cancer cell in vitro with an $EC_{50}$ of less than about 0.2 pM.

Embodiment 9 is an isolated nucleic acid encoding HC1 and LC1 of the Vβ17 bispecific antibody or antigen-binding fragment thereof of any one of embodiments 1 to 8.

Embodiment 10 is an isolated nucleic acid encoding HC2 and LC2 of the Vβ17 bispecific antibody or antigen-binding fragment thereof of any one of embodiments 1 to 8.

Embodiment 11 is a vector comprising the isolated nucleic acid of embodiment 9 or embodiment 10.

Embodiment 12 is a host cell comprising the vector of embodiment 11.

Embodiment 13 is a buffered composition comprising the isolated Vβ17 bispecific antibody or antigen-binding fragment thereof of any one of embodiments 1 to 8 and a buffered solution.

Embodiment 14 is an isolated anti-Vβ17/anti-CD123 bispecific antibody or antigen-binding fragment thereof comprising:
a. a first heavy chain (HC1);
b. a second heavy chain (HC2)
c. a first light chain (LC1); and
d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen that specifically binds Vβ17, and wherein HC2 comprises a heavy chain complementarity determining region 1 (HCDR1), HCDR2, and HCDR3 comprising the amino acid sequences of SEQ ID NO:34, SEQ ID NO:35, and SEQ ID NO:36, respectively, and LC2 comprises a light chain complementarity determining region 1 (LCDR1), LCDR2, and LCDR3 comprising the amino acid sequences of SEQ ID NO:37, SEQ ID NO:38, and SEQ ID NO:39, respectively, to form a binding site for a second antigen that specifically binds CD123.

Embodiment 15 is the isolated anti-Vb17/anti-CD123 bispecific antibody or antigen-binding fragment of embodiment 14, wherein HC1 comprises the amino acid sequence of SEQ ID NO:13 and LC1 comprises the amino acid sequence of SEQ ID NO:14, and wherein HC2 comprises the amino acid sequence of SEQ ID NO:15 and LC2 comprises the amino acid sequence of SEQ ID NO:16.

Embodiment 16 is the isolated anti-Vβ17/anti-CD123 bispecific antibody or antigen-binding fragment thereof of embodiment 14 or embodiment 15, wherein the Vβ17 is on the surface of a CD8+ or CD4+ T cell.

Embodiment 17 is the isolated anti-Vβ17/anti-CD123 bispecific antibody or antigen-binding fragment thereof of any one of embodiments 14 to 16, wherein the CD123 is on the surface of a cancer cell.

Embodiment 18 is the isolated anti-Vβ17/anti-CD123 bispecific antibody or antigen-binding fragment thereof of any one of embodiments 14 to 17, wherein bispecific antibody or antigen-binding fragment thereof induces CD8+ or CD4+ T-cell dependent cytotoxicity of a cancer cell in vitro with an $EC_{50}$ of less than about 0.2 pM.

Embodiment 19 is an isolated nucleic acid encoding the HC1 and LC1 of the anti-Vβ17/anti-CD123 bispecific antibody or antigen-binding fragment thereof of any one of embodiments 14 to 18.

Embodiment 20 is an isolated nucleic acid encoding the HC2 and LC2 of the anti-Vβ17/anti-CD123 bispecific antibody or antigen-binding fragment thereof of any one of embodiments 14 to 18.

Embodiment 21 is a vector comprising the isolated nucleic acid of embodiment 19 or embodiment 20.

Embodiment 22 is a host cell comprising the vector of embodiment 21.

Embodiment 23 is a buffered composition comprising the isolated anti-Vβ17/anti-CD123 bispecific antibody or antigen-binding fragment thereof of any one of embodiments 14 to 18 and a buffered solution.

Embodiment 24 is a method of directing a Vβ17-expressing CD8+ or CD4+ T cell to a cancer cell, the method comprising contacting a Vβ17-expressing CD8+ or CD4+ T cell with the anti-Vβ17/anti-CD123 bispecific antibody or antigen-binding fragment thereof of any one of embodiments 1 to 8 or 14 to 18, wherein contacting the Vβ17-expressing CD8+ or CD4+ T cell with the anti-Vβ17/anti-CD123 bispecific antibody or antigen-binding fragment thereof directs the Vβ17-expressing CD8+ or CD4+ T cell to a cancer cell having CD123 on its surface.

Embodiment 24(a) is the method of embodiment 24, wherein the Vβ17-expressing CD8+ or CD4+ T cell is contacted with an anti-Vβ17/anti-CD123 bispecific antibody of any one of embodiments 1 to 8 or 14 to 18.

Embodiment 24(b) is the method of embodiment 24, wherein the Vβ17-expressing CD8+ or CD4+ T cell is contacted with an anti-Vβ17/anti-CD123 bispecific antibody fragment of any one of embodiments 1 to 8 or 14 to 18.

Embodiment 25 is a method for inhibiting growth or proliferation of cancer cells expressing CD123 on its surface, the method comprising contacting the cancer cells with the anti-Vβ17/anti-CD123 bispecific antibody or fragment thereof with any one of embodiments 1 to 8 or 14 to 18, wherein contacting the cancer cells with said antibody or antibody fragment inhibits the growth or proliferation of the cancer cells.

Embodiment 25(a) is the method of embodiments 25, wherein the CD123-expressing cancer cell is in the presence of a Vβ17-expressing CD8+ T cell while in contact with an anti-Vβ17/anti-CD123 bispecific antibody or fragment thereof.

Embodiment 25(b) is the method of embodiment 25 or 25(a), wherein the CD123-expressing cancer cell is contacted with an anti-Vβ17/anti-CD123 bispecific antibody of any one of embodiments 1 to 8 or 14 to 18.

Embodiment 25(c) is the method of embodiment 25 or 25(a), wherein the CD123-expressing cancer cell is contacted with an anti-Vβ17/anti-CD123 bispecific antibody fragment of any one of embodiments 1 to 8 or 14 to 18.

Embodiment 26 is a kit comprising a Vβ17 bispecific antibody or antigen-binding fragment thereof of any one of embodiments 1 to 8 and packaging for the same.

Embodiment 27 is a kit comprising an anti-Vβ17/anti-CD123 bispecific antibody or antigen-binding fragment thereof of any one of embodiments 14 to 18 and packaging for the same.

Embodiment 28 is a method of producing a Vβ17 bispecific antibody or antigen-binding fragment thereof, comprising culturing the host cell of embodiment 12 under conditions to produce the Vβ17 bispecific antibody or antigen-binding fragment thereof, and recovering the Vβ17 bispecific antibody or antigen-binding fragment thereof from the cell or culture.

Embodiment 29 is a method of producing an anti-Vβ17/anti-CD123 bispecific antibody or antigen-binding fragment thereof of any one of embodiments 14 to 18, comprising culturing the host cell of embodiment 22 under conditions to produce the anti-Vβ17/anti-CD123 bispecific antibody or antigen-binding fragment thereof, and recovering the anti-Vβ17/anti-CD123 bispecific antibody or antigen-binding fragment thereof from the cell or culture.

Embodiment 30 is an isolated humanized Vβ17 monoclonal antibody or antigen-binding fragment thereof, the Vβ17 monoclonal antibody or antigen-binding fragment thereof comprising an amino acid sequence with at least 95% identity to the amino acid sequence of SEQ ID NO:28.

Embodiment 31 is isolated humanized Vβ17 monoclonal antibody or antigen-binding fragment thereof of embodiment 30, wherein the Vβ17 monoclonal antibody or antigen-binding fragment thereof comprises the amino acid sequence of SEQ ID NO:28.

Embodiment 32 is an isolated nucleic acid encoding the humanized Vβ17 monoclonal antibody or antigen-binding fragment thereof of embodiment 30 or embodiment 31.

Embodiment 33 is a vector comprising the isolated nucleic acid of embodiment 32.

Embodiment 34 is a host cell comprising the vector of embodiment 33.

Embodiment 35 is a buffered composition comprising the isolated humanized Vβ17 monoclonal antibody or antigen-binding fragment thereof of embodiment 30 or embodiment 31.

EXAMPLES

The following examples are based on the premise that influenza virus derived peptide M1 is capable of expanding a select set of T cells. These cells express TCR-haplotype-Vβ17 and majority of these cells exhibit efficient cytotoxicity of tumor target cells. This ability is then harnessed using bispecific antibodies constructed such that one arm binds to the Vβ17 structure and the other arm binds to an antigen expressed by the cancer cells. Thus, the bispecific antibody bridges the effector and target cells together—resulting in cancer cell killing. This mechanism of action is described in the schematic outlined in FIG. 1.

The subsequent examples can be divided into the following categories: (1) Generation of bispecific antibodies capable of binding to the Vβ17 arm of T-cell receptors (TCR) on CTL (Examples 1 and 2); and (2) Evidence for bispecific antibody-enabled target cell killing by CTL expanded in vitro (Example 3).

Example 1: Human Framework Adaptation of anti-Vβ17 mAb E17.5F

The mouse IgG1 anti-human T cell receptor Vβ17 clone E17.5F was obtained from BeckmanCoulter, Inc. (Brea, CA). Sample preparation and LC/MSMS analysis were performed at Protea Bioscience Inc. (Morgantown, WV). The sample was reduced and alkylated, divided into seven aliquots, and proteolytically digested with Trypsin/LysC, Chymotrypsin, LysC, Pepsin, and AspN, Elastase, and Proteinase K enzymes. Resulting peptides were desalted using a ZipTip C18 Pipette Tips and separated on-line using reverse phase chromatography. Mass spectrometry was performed on Thermo Q-Exactive spectrometer using HCD fragmentation. MS data sets were analyzed using PEAKS software by matching de novo sequence tags to an IMGT-based antibody sequences database. Gaps in the sequence were assigned using Contig sequence assembly of de novo identified peptides. All CDRs and hyper-mutations were confirmed by inspecting the MS/MS spectra The sequences obtained are shown in Tables 1 and 2.

TABLE 1

CDR Sequences of TCR Vβ17 clone E17.5F.

| Antibody | HCDR1 | SEQ ID NO: | HCDR2 | SEQ ID NO: | HCDR3 | SEQ ID NO: |
|---|---|---|---|---|---|---|
| E17.5F | GYSITSGYFWN | 1 | YISYDGSNN | 2 | PSPGTGYAVDY | 3 |
| Antibody | LCDR1 | SEQ ID NO: | LCDR2 | SEQ ID NO: | LCDR3 | SEQ ID NO: |
| E17.5F | RSSQSLVHSNGNTYLH | 4 | KVSNRFS | 5 | SQSTHVPFT | 6 |

TABLE 2

Heavy chain and light chain sequences of TCR Vb17 clone E17.5F.

| mAb ID | Heavy Chain Amino Acid Sequence | SEQ ID NO: |
|---|---|---|
| B171301 | NVQLQESGPGLVKPSQSLSLTCSVAGYSITSGYFWNWIRQFPGNKLEWMGYIS YDGSNNYNPSLKNRISITRDTSKNQFFLKLNSVTTEDTATYYCASPSPGTGYA VDYWGQGTSVTVSSAKTTPPSVYPLAPGSAAQTNSMVTLGCLVKGYFPEPVTV TWNSGSLSSGVHTFPAVLQSDLYTLSSSVTVPSSTWPSQTVTCNVAHPASSTK VDKKIVPRDCGCKPCICTVPEVSSVFIFPPKPKDVLTITLTPKVTCVVVDISK DDPEVQFSWFVDDVEVHTAQTKPREEQINSTFRSVSELPIMHQDWLNGKEFKC RVNSAAFPAPIEKTISKTYGRPKAPQVYTIPPPKEQMAKDKVSLTCMITNFFP EDITVEWQWNGQPAENYKNTQPIMDTDGSYFVYSKLNVQKSNWEAGNTFTCSV LHEGLHNHHTEKSLSHSPGK | 7 |
| | Light Chain Amino Acid Sequence | SEQ ID NO: |
| B17B01 | NVVMTQTPLSLPVSLGDQASISCRSSQSLVHSNGNTYLHWYLQKPGQSPKFLI YKVSNRFSGVPDRFSGGSGTEFTLKISRVEAEDLGVYFCSQSTHVPFTFGSG TKLEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPIVK SFNRNEC | 8 |

Changes were made in the sequences for the preparation of bispecific antibodies (Table 3). The changes include the following: (1) a framework mutation Asn1 of the heavy chain was not conserved, so the sequence has been modified to have the DVQLW sequence; (2) another mutation identified in the Fc, K337Y, was deemed uncharacteristic, and, thus, a construct without this mutation was synthesized; and (3) a potential secondary glycosylation site on the heavy chain was observed, and, thus, two versions of this mAb with and without the N-linked site (N82a, based on Chothia numbering) were synthesized.

TABLE 3

Heavy and Light Chain sequences for Vβ17 clone E17.5F antibody variants

| mAb ID | Heavy Chain Amino Acid Sequence | SEQ ID NO: |
|---|---|---|
| B17B1 | NVQLQESGPGLVKPSQSLSLTCSVAGYSITSGYFWNWIRQFPGNKLEWMGYIS YDGSNNYNPSLKNRISITRDTSKNQFFLKLNSVTTEDTATYYCASPSPGTGYAV DYWGQGTSVTVSSASTKGPSVFPLAPCSRSTSESTAALGCLVKDYFPEPVTVS WNSGALTSGVHTFPAVLQSSGLYSLSSVVTVPSSSLGTKTYTCNVDHKPSNTK VDKRVESKYGPPCPPCPAPEAAGGPSVFLFPPKPKDTLMISRTPEVTCVVVDVS QEDPEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLVKGF YPSDIAVEWESNGQPENNYKTTPPVLDSDGSFLLYSKLTVDKSRWQEGNVFSC SVMHEALHNHYTQKSLSLSLGK | 9 |
| B17B2 | DVQLKESGPGLVKPSQSLSVTCSVTGYSITSGYYWNWYRQFPGNKLEWMGYI SYDGSNNYNPSLKNRISITRDTSKNQILLKLTYVTTEDTATYYCTRPSPGTYA VDYWGQGTLVTVSSASTKGPSVFPLAPCSRSTSESTAALGCLVKDYFPEPVTVS WNSGALTSGVHTFPAVLQSSGLYSLSSVVTVPSSSLGTKTYTCNVDHKPSNTK VDKRVESKYGPPCPPCPAPEAAGGPSVFLFPPKPKDTLMISRTPEVTCVVVDVS QEDPEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLVKGF YPSDIAVEWESNGQPENNYKTTPPVLDSDGSFLLYSKLTVDKSRWQEGNVFSC SVMHEALHNHYTQKSLSLSLGK | 11 |

| | Light Chain Amino Acid Sequence | SEQ ID NO: |
|---|---|---|
| B17B1 | NVVMTQTPLSLPVSLGDQASISCRSSQSLVHSNGNTYLHWYLQKPGQSPKFLIY KVSNRFSGVPDRFSGGGSGTEFTLKISRVEAEDLGVYFCSQSTHVPFTFGSGTK LEIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSFN RNEC | 10 |
| B17B2 | DIVMTQSPDSLAVSLGERATINCRSSQSLVHSNGNTYLHWYQQKPGQPPKLLI YKVSNRFSGVPDRFSGSGSGTDFTLTISSLQAEDVAVYYCSQSTHVPFTFGQGT KVEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKSF NRNEC | 12 |

The two antibodies (B17B1 and B17B2) were expressed in HEK293Expi cells. The supernatants were tested for Vβ17 binding (B17B1 and B17B2) and only B17B1 demonstrated binding. Thus, B17B1 was expressed having an IgG4 constant region with Fc substitutions.

The anti-human TCR Vβ17 mouse mAb B17B1 was humanized using the Human Framework Adaptation (HFA) method (Fransson J, et al. *J. Mol. Biol.* 2010; 398:214-231). To find the best combination of humanized heavy and light chains, several human V-region sequences were selected for testing (Table 4). Selection of human germlines was based solely on the overall sequence similarity to the mouse antibody in the framework (FR) region. Neither the CDR sequences, nor their length or canonical structures, were considered in this selection.

The CDR definition used in HFA is described in (Fransson J, et al. *J. Mol. Biol.* 2010; 398:214-231) and corresponds to the Martin's definition (Abhinandan K R and Martin A C. *Mol. Immunol.* 2008; 45:3832-3839). The CDRs (Table 1) were defined as described below (using the Chothia numbering scheme [Chothia C, and Lesk A. *J. Mol. Biol.* 1987; 196:901-917]):

| | |
|---|---|
| HCDR1 26-35 | (SEQ ID NO: 1) |
| HCDR2 50-58 | (SEQ ID NO: 2) |
| HCDR3 95-102 | (SEQ ID NO: 3) |
| LCDR1 24-34 | (SEQ ID NO: 4) |
| LCDR2 50-56 | (SEQ ID NO: 5) |
| LCDR3 89-97 | (SEQ ID NO: 6) |

The selected human germlines are provided in Table 4 (in the IMGT notation).

TABLE 4

VH and VL variants

| Ab VH | Sequence | SEQ ID NO: |
|---|---|---|
| B17H1 | NVQLQESGPGLVKPSQSLSLTCVSVAGYSITSYGFWNWIRQFPGNKLEWMG YSIYDGSNNYNPSLKNRISITRDTSKNQFFLKLNSVTTEDTATYYCASPSP GTGYAVDYWGQGTSVTVSS | 25 |
| B17H3 | EVQLLESGGGLVQPGGSLRLSCAASGYSITSGYFWNWVRQAPGKGLEWVSY ISYDGSNNYADSVKGRFTISRDNSKNTLYLQMNSLRAEDTAVYYCAKPSPG TGYAVDYWGQGTLVTVSS | 19 |
| B17H4 | EVQLLESGGGLVQPGGSLRLSCAASGYSITSGYFWNWVRQAPGKGLEWVSY ISYDGSNNYADSVKGRFTISRDNSKNTLYLQMNSLRAEDTAVYYCASPSPG TGYAVDYWGQGTLVTVSS | 20 |
| B17H5 | QVQLVQESGPGLVKPSETLSLTCTVSGYSITSGYFWNWIRQPPGKGLEWIG YISYDGSNNYNPSLKSRVTISRDTSKNQFSLKLSSVTAADTAVYYCASPSP GTGYAVDYWGQGTLVTVSS | 21 |

| Ab VL | Sequence | SEQ ID NO: |
|---|---|---|
| B17L1 | NVVMTQTPLSLPVSLGDQASISVRSSQSLVHSNGNTYLHWYLQKPGQSPKF LIYKVSNRFSGVPDRFSGGGSGTEFTLKISRVEAEDLGVYFCSQSTHVPFT FGSGTKLEIK | 26 |
| B17L3 | DIQMTQSPSSLSASVGDRVTITCRSSQLSVHSNGNTYLHWYQQKPGKAPKL LIYKVSNRFSGVPSRFSGSGSGTDFTLTISSLQPEDFATYYCSQSTHVPFT FGQGTKLEIK | 22 |
| B17L4 | DIQMTQSPSSLSASVGDRVTITCRSSQSLVHSNGNTYLHWYQQKPGKAPKF LIYKVSNRFSGVPSRFSGSGSGTDFTLTISSLQPEDFATYYCSQSTHVPFT FGQGTKLEIK | 23 |
| B17L5 | DVVMTQSPLSLPVTLGQPASISVRSSQSLVHSNGNTYLHWFQQRPGQSPRF LIYKVSNRFSGVPDRFSGSGSGTDFTLKISRVEAEDVGVYYCSQSTHVPFT FGQGTKLEIK | 24 |

CRSs1-3 are underlined

"Back mutations" in several variants were introduced at FR positions that are known to be important for VL/VH pairing and CDR conformation. The selected human germlines are provided in Table 5 (in the IMGT notation), with the back mutations noted.

TABLE 5

The selected J-regions

| J-region | Sequence | SEQ ID NO: |
|---|---|---|
| IGHJ1*01 HC | WGQGTLVTVSS | 42 |
| IGKJ2*01 LC | FGQGTKLEIK | 43 |

Amino acid sequences of all nine pairwise combinations of three heavy chains and three light chains were back-translated to DNA, and cDNA was prepared using gene synthesis techniques (U.S. Pat. Nos. 6,670,127; 6,521,427). Heavy chain (HC) variable regions were subcloned onto human IgG4 constant region using an in-house expression vector with the CMV promoter using standard molecular biology techniques. Light chain (LC) variable regions were subcloned onto a human Lambda (k) constant regions using an in-house expression vector with the CMV promoter using standard molecular biology techniques. Resulting plasmids were transfected into HEK EXPI cells (LifeTechnologies; Carlsbad, CA) and mAbs were expressed. Purification was by standard methods using a Protein A column (hiTrap MAbSelect SuRe column). After elution, the pools were dialyzed into D-PBS, pH 7.2.

TABLE 6

Heavy and Light chains of nine humanized Vβ17 antibodies

| mAb | Hc | SEQ ID NO: | Lc | SEQ ID NO: | Concentration (µg/mL) |
|---|---|---|---|---|---|
| B17B14 | B17H3 | 19 | B17L3 | 22 | 686.3 |
| B17B15 | B17H3 | 19 | B17L4 | 23 | 13.8 |
| B17B16 | B17H3 | 19 | B17L5 | 24 | 14.6 |
| B17B17 | B17H4 | 20 | B17L3 | 22 | 335.1 |
| B17B18 | B17H4 | 20 | B17L4 | 23 | 45.2 |
| B17B19 | B17H4 | 20 | B17L5 | 24 | 27.5 |
| B17B20 | B17H5 | 21 | B17L3 | 22 | 602.1 |
| B17B21 | B17H5 | 21 | B17L4 | 23 | 570.9 |
| B17B22 | B17H5 | 21 | B17L5 | 24 | 320.5 |

The humanized antibodies were screened for binding to a TCRVβ17 (SEQ ID NO:27)/Va10.2-Fc (SEQ ID NO:44) fusion protein by ELISA. Biotinylated TCRVβ17/Va10.2-Fc fusion protein was added to a streptavidin-coated ELISA plate. Unbound protein was washed away and mAb was added at a range of concentrations (0.01-10 µg/mL). Plates were washed and anti-kappa:HRP detection antibody was added. Plates were washed, chemiluminescent detection reagent was added, and the plates were read on a Perkin Elmer EnVision plate reader for luminescence. B17B20 and B17B21 showed positive binding to the TCR-Vβ17 protein. B17B22 showed weak binding to this protein. These antibodies were then purified as described above for further studies. B17B21 demonstrated the best binding to recombinant TCR-Vβ17 protein and to M1-stimulated T-cells and was thus chosen as the molecule for further functional studies, specifically T-cell re-directed cancer cell killing as a bispecific antibody.

Thus, the variable region sequence of B17B21 (anti-Vβ17) and I3RB217 (anti-CD123 antibody) was used to generate a bispecific antibody to be tested for T-cell re-directed killing of acute myeloid leukemia (AML) cells.

Example 2. Preparation of Anti-Vβ17/Anti-CD123 Bispecific Antibodies

VB11 (anti-Vβ17/anti-CD123) and VB13 (Vβ17×Null) bispecific antibodies were produced as full-length antibodies in the knob-into-hole format as human IgG4, as previously described (Atwell et al. J. Mol. Biol. 270: 26-35, 1997). Nucleic acid sequences encoding variable regions were subcloned into a custom mammalian expression vectors containing constant region of IgG4 expression cassettes using standard PCR restriction enzyme based cloning techniques. The bispecific antibodies were expressed by transient transfection in Chinese hamster ovary cell line. The antibodies were initially purified by Mab Select SuRe Protein A column (GE healthcare, Piscataway, New Jersey) (Brown, Bottomley et al. 1998). The column was equilibrated with Phosphate Buffer Saline (PBS), pH 7.2 and loaded with fermentation supernatant at a flow rate of 2 mL/min. After loading, the column was washed with PBS (4 CV) followed by elution in 30 mM sodium acetate, pH 3.5. Fractions containing protein peaks as monitored by Absorbance at 280 nm in Akta Explorer (GE healthcare) were pooled together and were neutralized to pH 5.0 by adding 1% of 3M sodium acetate, pH 9.0. As a polishing step, the antibodies were purified on a preparative size exclusion chromatography (SEC) using a Superdex 200 column (GE healthcare). The integrity of the sample was assessed by endotoxin measurement and SDS polyacrylamide gel electrophoresis under reducing and non-reducing conditions. The final protein concentrations were 0.48 mg/ml for anti-Vβ17/anti-CD123 and 0.24 mg/mL for Vβ17×Null. The final EU levels of anti-Vβ17/anti-CD123 and Vβ17×Null based on these protein concentrations were 2.053 EU/mg and 4.219 EU/mg, respectively.

TABLE 7

Sequences of half antibodies expressed in CHO cells

| mAb ID | | SEQ ID NO: |
|---|---|---|
| | 'Knob' arm and 'hole' arm amino acid sequence | |
| B17B21 (Vβ17 half Ab) | MAWVWTLLFLMAAAQSIQADIQMTQSPSSLSASVGDRVTITCRSSQSLVHS NGNTYLHWYQQKPGKAPKFLIYKVSNRFSGVPSRFSGSGSGTDFTLTISSL QPEDFATYYCSQSTHVPFTFGQGTKLEIKRTVAAPSVFIFPPSDEQLKSGT ASVVCLLNNFYPREAKVQWKVDNALQSGNSQESVTEQDSKDSTYSLSSTLT LSKADYEKHKVYACEVTHQGLSSPVTKSFNRGECGGSEGKSSGSGSESKST EGKSSGSGSESKSTGGSQVQLQESGPGLVKPSETLSLTCTVSGYSITSGYF WNWIRQPPGKGLEWIGYISYDGSNNYNPSLKSRVTISRDTSKNQFSLKLSS VTAADTAVYYCASPSPGTGYAVDYWGQGTLVTVSSASTKGPSVFPLAPCSR STSESTAALGCLVKDYFPEPVTVSWNSGALTSGVHTFPAVLQSSGLYSLSS VVTVPSSSLGTKTYTCNVDHKPSNTKVDKRVESKYGPPCPPCPAPEAAGGP SVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAK GQPREPQVYTLPPSQEEMTKNQVSLSCAVKGFYPSDIAVEWESNGQPENNY KTTPPVLDSDGSFFLVSRLTVDKSRWQEGNVFSCSVMHEALHNRFTQKSLS LSLGK | 28 |
| I3RB217 (CD123 half Ab) | MAWVWTLLFLMAAAQSIQAEIVLTQSPGTLSLSPGERATLSCRASQSVSSS YLAWYQQKPGQAPRLLIYGASSRATGIPDRFSGSGSGTDFTLTISRLEPED FAVYYCQQDYGFPWTFGQGTKVEIKRTVAAPSVFIFPPSDEQLKSGTASVV CLLNNFYPREAKVQWKVDNALQSGNSQESVTEQDSKDSTYSLSSTLTLSKA DYEKHKVYACEVTHQGLSSPVTKSFNRGECGGSEGKSSGSGSESKSTEGKS SGSGSESKSTGGSEVQLVQSGAEVKKPGESLKISCKGSGYSFTSYWISWVR QMPGKGLEWMGIIDPSDSDTRYSPSFQGQVTISADKSISTAYLQWSSLKAS DTAMYYCARGDGSTDLDYWGQGTLVTVSSASTKGPSVFPLAPCSRSTSEST AALGCLVKDYFPEPVTVSWNSGALTSGVHTFPAVLQSSGLYSLSSVVTVPS SSLGTKTYTCNVDHKPSNTKVDKRVESKYGPPCPPCPAPEAAGGPSVFLFP PKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREP QVYTLPPSQEEMTKNQVSLWCLVKGFYPSDIAVEWESNGQPENNYKTTPPV LDSDGSFFLYSRLTVDKSRWQEGNVFSCSVMHEALHNHYTQKSLSLSLGK | 30 |
| B23B49 (Null half Ab) | MAWVWTLLFLMAAAQSIQAEIVLTQSPGTLSLSPGERATLSCRASQSVSSS YLAWYQQKPGQAPRLLIYGASSRATGIPDRFSGSGSGTDFTLTISRLEPED FAVYYCQQDYGFPWTFGQGTKVEIKRTVAAPSVFIFPPSDEQLKSGTASVV CLLNNFYPREAKVQWKVDNALQSGNSQESVTEQDSKDSTYSLSSTLTLSKA DYEKHKVYACEVTHQGLSSPVTKSFNRGECGGSEGKSSGSGSESKSTEGKS SGSGSESKSTGGSEVQLVQSGAEVKKPGESLKISCKGSGYSFTSYWISWVR QMPGKGLEWMGIIDPSDSDTRYSPSFQGQVTISADKSISTAYLQWSSLKAS DTAMYYCARGDGSTDLDYWGQGTLVTVSSASTKGPSVFPLAPCSRSTSEST AALGCLVKDYFPEPVTVSWNSGALTSGVHTFPAVLQSSGLYSLSSVVTVPS SSLGTKTYTCNVDHKPSNTKVDKRVESKYGPPCPPCPAPEAAGGPSVFLFP PKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREP QVYTLPPSQEEMTKNQVSLWCLVKGFYPSDIAVEWESNGQPENNYKTTPPV LDSDGSFFLYSRLTVDKSRWQEGNVFSCSVMHEALHNHYTQKSLSLSLGK | |
| | Half Antibody DNA sequence | |
| B17B21 (Vβ17 half Ab) | ATGGCCTGGGTGTGGACCCTGCTGTTCCTGATGGCCGCCGCCCAGAGCATC CAGGCCGACATCCAGATGACCCAGAGCCCAAGCAGCCTGAGCGCCAGCGTG GGCGACCGCGTGACCATCACCTGCCGCAGCAGCCAGAGCCTGGTGCACAGC AACGGCAACACCTACCTGCACTGGTACCAGCAGAAGCCAGGCAAGGCCCCA AAGTTCCTGATCTACAAGGTGAGCAACCGCTTCAGCGGCGTGCCAAGCCGC TTCAGCGGCAGCGGCAGCGGCACCGACTTCACCCTGACCATCAGCAGCCTG | 29 |

TABLE 7-continued

Sequences of half antibodies expressed in CHO cells

| mAb ID | SEQ ID NO: |
|---|---|
| CAGCCAGAGGACTTCGCCACCTACTACTGCAGCCAGAGCACCCACGTGCCA | |
| TTCACCTTCGGCCAGGGCACCAAGCTGGAGATCAAGCGCACCGTGGCCGCC | |
| CCAAGCGTGTTCATCTTCCCACCAAGCGACGAGCAGCTGAAGAGCGGCACC | |
| GCCAGCGTGGTGTGCCTGCTGAACAACTTCTACCCACGCGAGGCCAAGGTG | |
| CAGTGGAAGGTGGACAACGCCCTGCAGAGCGGCAACAGCCAGGAGAGCGTG | |
| ACCGAGCAGGACAGCAAGGACAGCACCTACAGCCTGAGCAGCACCCTGACC | |
| CTGAGCAAGGCCGACTACGAGAAGCACAAGGTGTACGCCTGCGAGGTGACC | |
| CACCAGGGCCTGAGCAGCCCAGTGACCAAGAGCTTCAACCGCGGCGAGTGC | |
| GGCGGCAGCGAGGGCAAGAGCAGCGGCAGCGGCAGCGAGAGCAAGAGCACC | |
| GAGGGCAAGAGCAGCGGCAGCGGCAGCGAGAGCAAGAGCACCGGCGGCAGC | |
| CAGGTGCAGCTGCAGGAGAGCGGCCCAGGCCTGGTGAAGCCAAGCGAGACC | |
| CTGAGCCTGACCTGCACCGTGAGCGGCTACAGCATCACCAGCGGCTACTTC | |
| TGGAACTGGATCCGCCAGCCACCAGGCAAGGGCCTGGAGTGGATCGGCTAC | |
| ATCAGCTACGACGGCAGCAACAACTACAACCCAAGCCTGAAGAGCCGCGTG | |
| ACCATCAGCCGCGACACCAGCAAGAACCAGTTCAGCCTGAAGCTGAGCAGC | |
| GTGACCGCCGCCGACACCGCCGTGTACTACTGCGCCAGCCCAAGCCCAGGC | |
| ACCGGCTACGCCGTGGACTACTGGGGCCAGGGCACCCTGGTGACCGTGAGC | |
| AGCGCCAGCACCAAGGGCCCAAGCGTGTTCCCACTGGCCCCATGCAGCCGC | |
| AGCACCAGCGAGAGCACCGCCGCCCTGGGCTGCCTGGTGAAGGACTACTTC | |
| CCAGAGCCAGTGACCGTGAGCTGGAACAGCGGCGCCCTGACCAGCGGCGTG | |
| CACACCTTCCCAGCCGTGCTGCAGAGCAGCGGCCTGTACAGCCTGAGCAGC | |
| GTGGTGACCGTGCCAAGCAGCAGCCTGGGCACCAAGACCTACACCTGCAAC | |
| GTGGACCACAAGCCAAGCAACACCAAGGTGGACAAGCGCGTGGAGAGCAAG | |
| TACGGCCCACCATGCCCACCATGCCCAGCCCCAGAGGCCGCCGGCGGCCCA | |
| AGCGTGTTCCTGTTCCCACCAAAGCCAAAGGACACCCTGATGATCAGCCGC | |
| ACCCCAGAGGTGACCTGCGTGGTGGTGGACGTGAGCCAGGAGGACCCAGAG | |
| GTGCAGTTCAACTGGTACGTGGACGGCGTGGAGGTGCACAACGCCAAGACC | |
| AAGCCACGCGAGGAGCAGTTCAACAGCACCTACCGCGTGGTGAGCGTGCTG | |
| ACCGTGCTGCACCAGGACTGGCTGAACGGCAAGGAGTACAAGTGCAAGGTG | |
| AGCAACAAGGGCCTGCCAAGCAGCATCGAGAAGACCATCAGCAAGGCCAAG | |
| GGCCAGCCACGCGAGCCACAGGTGTACACCCTGCCACCAAGCCAGGAGGAG | |
| ATGACCAAGAACCAGGTGAGCCTGAGCTGCGCCGTGAAGGGCTTCTACCCA | |
| AGCGACATCGCCGTGGAGTGGGAGAGCAACGGCCAGCCAGAGAACAACTAC | |
| AAGACCACCCCACCAGTGCTGGACAGCGACGGCAGCTTCTTCCTGGTGAGC | |
| CGCCTGACCGTGGACAAGAGCCGCTGGCAGGAGGGCAACGTGTTCAGCTGC | |
| AGCGTGATGCACGAGGCCCTGCACAACCGCTTCACCCAGAAGAGCCTGAGC | |
| CTGAGCCTGGGCAAGATGGCCTGGGTGTGGACCCTGCTGTTCCTGATGGCC | |
| GCCGCCCAGAGCATCCAGGCCGACATCCAGATGACCCAGAGCCCAAGCAGC | |
| CTGAGCGCCAGCGTGGGCGACCGCGTGACCATCACCTGCCGCAGCAGCCAG | |
| AGCCTGGTGCACAGCAACGGCAACACCTACCTGCACTGGTACCAGCAGAAG | |
| CCAGGCAAGGCCCCAAAGTTCCTGATCTACAAGGTGAGCAACCGCTTCAGC | |
| GGCGTGCCAAGCCGCTTCAGCGGCAGCGGCAGCGGCACCGACTTCACCCTG | |
| ACCATCAGCAGCCTGCAGCCAGAGGACTTCGCCACCTACTACTGCAGCCAG | |
| AGCACCCACGTGCCATTCACCTTCGGCCAGGGCACCAAGCTGGAGATCAAG | |
| CGCACCGTGGCCGCCCCAAGCGTGTTCATCTTCCCACCAAGCGACGAGCAG | |
| CTGAAGAGCGGCACCGCCAGCGTGGTGTGCCTGCTGAACAACTTCTACCCA | |
| CGCGAGGCCAAGGTGCAGTGGAAGGTGGACAACGCCCTGCAGAGCGGCAAC | |
| AGCCAGGAGAGCGTGACCGAGCAGGACAGCAAGGACAGCACCTACAGCCTG | |
| AGCAGCACCCTGACCCTGAGCAAGGCCGACTACGAGAAGCACAAGGTGTAC | |
| GCCTGCGAGGTGACCCACCAGGGCCTGAGCAGCCCAGTGACCAAGAGCTTC | |
| AACCGCGGCGAGTGCGGCGGCAGCGAGGGCAAGAGCAGCGGCAGCGGCAGC | |
| GAGAGCAAGAGCACCGAGGGCAAGAGCAGCGGCAGCGGCAGCGAGAGCAAG | |
| AGCACCGGCGGCAGCCAGGTGCAGCTGCAGGAGAGCGGCCCAGGCCTGGTG | |
| AAGCCAAGCGAGACCCTGAGCCTGACCTGCACCGTGAGCGGCTACAGCATC | |
| ACCAGCGGCTACTTCTGGAACTGGATCCGCCAGCCACCAGGCAAGGGCCTG | |
| GAGTGGATCGGCTACATCAGCTACGACGGCAGCAACAACTACAACCCAAGC | |
| CTGAAGAGCCGCGTGACCATCAGCCGCGACACCAGCAAGAACCAGTTCAGC | |
| CTGAAGCTGAGCAGCGTGACCGCCGCCGACACCGCCGTGTACTACTGCGCC | |
| AGCCCAAGCCCAGGCACCGGCTACGCCGTGGACTACTGGGGCCAGGGCACC | |
| CTGGTGACCGTGAGCAGCGCCAGCACCAAGGGCCCAAGCGTGTTCCCACTG | |
| GCCCCATGCAGCCGCAGCACCAGCGAGAGCACCGCCGCCCTGGGCTGCCTG | |
| GTGAAGGACTACTTCCCAGAGCCAGTGACCGTGAGCTGGAACAGCGGCGCC | |
| CTGACCAGCGGCGTGCACACCTTCCCAGCCGTGCTGCAGAGCAGCGGCCTG | |
| TACAGCCTGAGCAGCGTGGTGACCGTGCCAAGCAGCAGCCTGGGCACCAAG | |
| ACCTACACCTGCAACGTGGACCACAAGCCAAGCAACACCAAGGTGGACAAG | |
| CGCGTGGAGAGCAAGTACGGCCCACCATGCCCACCATGCCCAGCCCCAGAG | |
| GCCGCCGGCGGCCCAAGCGTGTTCCTGTTCCCACCAAAGCCAAAGGACACC | |
| CTGATGATCAGCCGCACCCCAGAGGTGACCTGCGTGGTGGTGGACGTGAGC | |
| CAGGAGGACCCAGAGGTGCAGTTCAACTGGTACGTGGACGGCGTGGAGGTG | |
| CACAACGCCAAGACCAAGCCACGCGAGGAGCAGTTCAACAGCACCTACCGC | |
| GTGGTGAGCGTGCTGACCGTGCTGCACCAGGACTGGCTGAACGGCAAGGAG | |
| TACAAGTGCAAGGTGAGCAACAAGGGCCTGCCAAGCAGCATCGAGAAGACC | |
| ATCAGCAAGGCCAAGGGCCAGCCACGCGAGCCACAGGTGTACACCCTGCCA | |
| CCAAGCCAGGAGGAGATGACCAAGAACCAGGTGAGCCTGAGCTGCGCCGTG | |
| AAGGGCTTCTACCCAAGCGACATCGCCGTGGAGTGGGAGAGCAACGGCCAG | |
| CCAGAGAACAACTACAAGACCACCCCACCAGTGCTGGACAGCGACGGCAGC | |

TABLE 7-continued

Sequences of half antibodies expressed in CHO cells

| mAb ID | | SEQ ID NO: |
|---|---|---|
| | TTCTTCCTGGTGAGCCGCCTGACCGTGGACAAGAGCCGCTGGCAGGAGGGC<br>AACGTGTTCAGCTGCAGCGTGATGCACGAGGCCCTGCACAACCGCTTCACC<br>CAGAAGAGCCTGAGCCTGAGCCTGGGCAAGTGATAG | |
| I3RB217<br>(CD123<br>half Ab) | ATGGCCTGGGTGTGGACCCTGCTGTTCCTGATGGCCGCCGCCCAGAGCATC<br>CAGGCCGAGATCGTGCTGACCCAGAGCCCAGGCACCCTGAGCCTGAGCCCA<br>GGCGAGCGCGCCACCCTGAGCTGCCGCGCCAGCCAGAGCGTGAGCAGCAGC<br>TACCTGGCCTGGTACCAGCAGAAGCCAGGCCAGGCCCCACGCCTGCTGATC<br>TACGGCGCCAGCAGCCGCGCCACCGGCATCCCAGACCGCTTCAGCGGCAGC<br>GGCAGCGGCACCGACTTCACCCTGACCATCAGCCGCCTGGAGCCAGAGGAC<br>TTCGCCGTGTACTACTGCCAGCAGGACTACGGCTTCCCATGGACCTTCGGC<br>CAGGGCACCAAGGTGGAGATCAAGCGCACCGTGGCCGCCCCAAGCGTGTTC<br>ATCTTCCCACCAAGCGACGAGCAGCTGAAGAGCGGCACCGCCAGCGTGGTG<br>TGCCTGCTGAACAACTTCTACCCACGCGAGGCCAAGGTGCAGTGGAAGGTG<br>GACAACGCCCTGCAGAGCGGCAACAGCCAGGAGAGCGTGACCGAGCAGGAC<br>AGCAAGGACAGCACCTACAGCCTGAGCAGCACCCTGACCCTGAGCAAGGCC<br>GACTACGAGAAGCACAAGGTGTACGCCTGCGAGGTGACCCACCAGGGCCTG<br>AGCAGCCCAGTGACCAAGAGCTTCAACCGCGGCGAGTGCggcggcagcgag<br>ggcaagagcagcggcagcggcagcgagagcaagagcaccgagggcaagagc<br>agcggcagcggcagcgagagcaagagcaccggcggcagcGAGGTGCAGCTG<br>GTGCAGAGCGGCGCCGAGGTGAAGAAGCCAGGCGAGAGCCTGAAGATCAGC<br>TGCAAGGGCAGCGGCTACAGCTTCACCAGCTACTGGATCAGCTGGGTGCGC<br>CAGATGCCAGGCAAGGGCCTGGAGTGGATGGGCATCATCGACCCAAGCGAC<br>AGCGACACCCGCTACAGCCCAAGCTTCCAGGGCCAGGTGACCATCAGCGCC<br>GACAAGAGCATCAGCACCGCCTACCTGCAGTGGAGCAGCCTGAAGGCCAGC<br>GACACCGCCATGTACTACTGCGCCCGCGGCGACGGCAGCACCGACCTGGAC<br>TACTGGGGCCAGGGCACCCTGGTGACCGTGAGCAGCGCCAGCACCAAGGGC<br>CCAAGCGTGTTCCCACTGGCCCCATGCAGCCGCAGCACCAGCGAGAGCACC<br>GCCGCCTGGGCTGCCTGGTGAAGGACTACTTCCCAGAGCCAGTGACCGTG<br>AGCTGGAACAGCGGCGCCCTGACCAGCGGCGTGCACACCTTCCCAGCCGTG<br>CTGCAGAGCAGCGGCCTGTACAGCCTGAGCAGCGTGGTGACCGTGCCAAGC<br>AGCAGCCTGGGCACCAAGACCTACACCTGCAACGTGGACCACAAGCCAAGC<br>AACACCAAGGTGGACAAGCGCGTGGAGAGCAAGTACGGCCCACCATGCCCA<br>CCATGCCCAGCCCCAGAGGCCGCCGGCGGCCCCAAGCGTGTTCCTGTTCCCA<br>CCAAAGCCAAAGGACACCCTGATGATCAGCCGCACCCCAGAGGTGACCTGC<br>GTGGTGGTGGACGTGAGCCAGGAGGACCCAGAGGTGCAGTTCAACTGGTAC<br>GTGGACGGCGTGGAGGTGCACAACGCCAAGACCAAGCCACGCGAGGAGCAG<br>TTCAACAGCACCTACCGCGTGGTGAGCGTGCTGACCGTGCTGCACCAGGAC<br>TGGCTGAACGGCAAGGAGTACAAGTGCAAGGTGAGCAACAAGGGCCTGCCA<br>AGCAGCATCGAGAAGACCATCAGCAAGGCCAAGGGCCAGCCACGCGAGCCA<br>CAGGTGTACACCCTGCCACCAAGCCAGGAGGAGATGACCAAGAACCAGGTG<br>AGCCTGTGGTGCCTGGTGAAGGGCTTCTACCCAAGCGACATCGCCGTGGAG<br>TGGGAGAGCAACGGCCAGCCAGAGAACAACTACAAGACCACCCCACCAGTG<br>CTGGACAGCGACGGCAGCTTCTTCCTGTACAGCCGCCTGACCGTGGACAAG<br>AGCCGCTGGCAGGAGGGCAACGTGTTCAGCTGCAGCGTGATGCACGAGGCC<br>CTGCACAACCACTACACCCAGAAGAGCCTGAGCCTGAGCCTGGGCAAG | 31 |
| B23B49<br>(Null<br>half Ab) | ATGGCCTGGGTGTGGACCCTGCTGTTCCTGATGGCCGCCGCCCAGAGCATC<br>CAGGCCGACATCGTGATGACCCAGAGCCCAGACAGCCTGGCCGTGAGCCTG<br>GGCGAGCGCGCCACCATCAACTGCCGCGCCAGCCAGAGCGTGGACTACAAC<br>GGCATCAGCTACATGCACTGGTACCAGCAGAAGCCAGGCCAGCCACCAAAG<br>CTGCTGATCTACGCCGCCAGCAACCCAGAGAGCGGCGTGCCAGACCGCTTC<br>AGCGGCAGCGGCAGCGGCACCGACTTCACCCTGACCATCAGCAGCCTGCAG<br>GCCGAGGACGTGGCCGTGTACTACTGCCAGCAGATCATCGAGGACCCATGG<br>ACCTTCGGCCAGGGCACCAAGGTGGAGATCAAGCGCACCGTGGCCGCCCCA<br>AGCGTGTTCATCTTCCCACCAAGCGACGAGCAGCTGAAGAGCGGCACCGCC<br>AGCGTGGTGTGCCTGCTGAACAACTTCTACCCACGCGAGGCCAAGGTGCAG<br>TGGAAGGTGGACAACGCCCTGCAGAGCGGCAACAGCCAGGAGAGCGTGACC<br>GAGCAGGACAGCAAGGACAGCACCTACAGCCTGAGCAGCACCCTGACCCTG<br>AGCAAGGCCGACTACGAGAAGCACAAGGTGTACGCCTGCGAGGTGACCCAC<br>CAGGGCCTGAGCAGCCCAGTGACCAAGAGCTTCAACCGCGGCGAGTGCGGC<br>GGCAGCGAGGGCAAGAGCAGCGGCAGCGGCAGCGAGAGCAAGAGCACCGAG<br>GGCAAGAGCAGCGGCAGCGGCAGCGAGAGCAAGAGCACCGGCGGCAGCCAG<br>ATCACCCTGAAGGAGAGCGGCCCAACCCTGGTGAAGCCAACCCAGACCCTG<br>ACCCTGACCTGCACCTTCAGCGGCTTCAGCCTGAGCACCAGCGGCATGGGC<br>GTGAGCTGGATCCGCCAGCCACCAGGCAAGGCCCTGGAGTGGCTGGCCCAC<br>ATCTACTGGGACGACGACAAGCGCTACAACCCAAGCCTGAAGAGCCGCCTG<br>ACCATCACCAAGGACACCAGCAAGAACCAGGTGGTGCTGACCATGACCAAC<br>ATGGACCCAGTGGACACCGCCACCTACTACTGCGCCCGCCTGTACGGCTTC<br>ACCTACGGCTTCGCCTACTGGGGCCAGGGCACCCTGGTGACCGTGAGCAGC<br>GCCAGCACCAAGGGCCCAAGCGTGTTCCCACTGGCCCCATGCAGCCGCAGC<br>ACCAGCGAGAGCACCGCCGCCCTGGGCTGCCTGGTGAAGGACTACTTCCCA<br>GAGCCAGTGACCGTGAGCTGGAACAGCGGCGCCCTGACCAGCGGCGTGCAC<br>ACCTTCCCAGCCGTGCTGCAGAGCAGCGGCCTGTACAGCCTGAGCAGCGTG<br>GTGACCGTGCCAAGCAGCAGCCTGGGCACCAAGACCTACACCTGCAACGTG<br>GACCACAAGCCAAGCAACACCAAGGTGGACAAGCGCGTGGAGAGCAAGTAC<br>GGCCCACCATGCCCACCATGCCCAGCCCCAGAGGCCGCCGGCGGCCCAAGC<br>GTGTTCCTGTTCCCACCAAAGCCAAAGGACACCCTGATGATCAGCCGCACC | |

TABLE 7-continued

Sequences of half antibodies expressed in CHO cells

| mAb ID | SEQ ID NO: |
|---|---|
| | CCAGAGGTGACCTGCGTGGTGGTGGACGTGAGCCAGGAGGACCCAGAGGTG<br>CAGTTCAACTGGTACGTGGACGGCGTGGAGGTGCACAACGCCAAGACCAAG<br>CCACGCGAGGAGCAGTTCAACAGCACCTACCGCGTGGTGAGCGTGCTGACC<br>GTGCTGCACCAGGACTGGCTGAACGGCAAGGAGTACAAGTGCAAGGTGAGC<br>AACAAGGGCCTGCCAAGCAGCATCGAGAAGACCATCAGCAAGGCCAAGGGC<br>CAGCCACGCGAGCCACAGGTGTACACCCTGCCACCAAGCCAGGAGGAGATG<br>ACCAAGAACCAGGTGAGCCTGTGGTGCCTGGTGAAGGGCTTCTACCCAAGC<br>GACATCGCCGTGGAGTGGGAGAGCAACGGCCAGCCAGAGAACAACTACAAG<br>ACCACCCCACCAGTGCTGGACAGCGACGGCAGCTTCTTCCTGTACAGCCGC<br>CTGACCGTGGACAAGAGCCGCTGGCAGGAGGGCAACGTGTTCAGCTGCAGC<br>GTGATGCACGAGGCCCTGCACAACCACTACACCCAGAAGAGCCTGAGCCTG<br>AGCCTGGGCAAG |

TABLE 8

Heavy and Light Chain Sequences for Vβ17 bispecific antibodies

| Bispecific Antibody | | Amino Acid Sequence |
|---|---|---|
| Anti-Vβ17/<br>anti-CD123 | Heavy chain 1<br>B17B21<br>(SEQ ID NO: 13) | QVQLQESGPGLVKPSETLSLTCTVSGYSITSGYFWNWIRQPP<br>GKGLEWIGYISYDGSNNYNPSLKSRVTISRDTSKNQFSLKLS<br>SVTAADTAVYYCASPSPGTGYAVDYWGQGTLVTVSSASTKGP<br>SVFPLAPCSRSTSESTAALGCLVKDYFPEPVTVSWNSGALTS<br>GVHTFPAVLQSSGLYSLSSVVTVPSSSLGTKTYTCNVDHKPS<br>NTKVDKRVESKYGPPCPPCPAPEAAGGPSVFLFPPKPKDTLM<br>ISRTPEVTCVVVDVSQEDPEVQFNWYVDGVEVHNAKTKPREE<br>QFNSTYRVVSVLTVLHQDWLNGKEYKCKVSNKGLPSSIEKTI<br>SKAKGQPREPQVYTLPPSQEEMTKNQVSLSCAVKGFYPSDIA<br>VEWESNGQPENNYKTTPPVLDSDGSFFLVSRLTVDKSRWQEG<br>NVFSCSVMHEALHNRFTQKSLSLSLGK |
| | Light Chain 1<br>B17B21<br>(SEQ ID NO: 14) | DIQMTQSPSSLSASVGDRVTITCRSSQSLVHSNGNTYLHWYQ<br>QKPGKAPKFLIYKVSNRFSGVPSRFSGSGSGTDFTLTISSLQ<br>PEDFATYYCSQSTHVPPTFGQGTKLEIKRTVAAPSVFIFPPS<br>DEQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC |
| | Heavy chain 2<br>I3RB217<br>(SEQ ID NO: 15) | EVQLVQSGAEVKKPGESLKISCKGSGYSFTSYWISWVRQMPG<br>KGLEWMGIIDPSDSDTRYSPSFQGQVTISADKSISTAYLQWS<br>SLKASDTAMYYCARGDGSTDLDYWGQGTLVTVSSASTKGPSV<br>FPLAPCSRSTSESTAALGCLVKDYFPEPVTVSWNSGALTSGV<br>HTFPAVLQSSGLYSLSSVVTVPSSSLGTKTYTCNVDHKPSNT<br>KVDKRVESKYGPPCPPCPAPEAAGGPSVFLFPPKPKDTLMIS<br>RTPEVTCVVVDVSQEDPEVQFNWYVDGVEVHNAKTKPREEQF<br>NSTYRVVSVLTVLHQDWLNGKEYKCKVSNKGLPSSIEKTISK<br>AKGQPREPQVYTLPPSQEEMTKNQVSLWCLVKGFYPSDIAVE<br>WESNGQPENNYKTTPPVLDSDGSFFLYSRLTVDKSRWQEGNV<br>FSCSVMHEALHNHYTQKSLSLSLGK |
| | Light Chain 2<br>I3RB217<br>(SEQ ID NO: 16) | EIVLTQSPGTLSLSPGERATLSCRASQSVSSSYLAWYQQKPG<br>QAPRLLIYGASSRATGIPDRFSGSGSGTDFTLTISRLEPEDF<br>AVYYCQQDYGFPWTFGQGTKVEIKRTVAAPSVFIFPPSDEQL<br>KSGTASVVCLLNNFYPREAKVQWKVDNALQSGNSQESVTEQD<br>SKDSTYSLSSTLTLSKADYEKHKVYACEVTHQGLSSPVTKSF<br>NRGEC |
| Vβ17 x Null | Heavy chain 1<br>B17B21<br>(SEQ ID NO: 13) | QVQLQESGPGLVKPSETLSLTCTVSGYSITSGYFWNWIRQPP<br>GKGLEWIGYISYDGSNNYNPSLKSRVTISRDTSKNQFSLKLS<br>SVTAADTAVYYCASPSPGTGYAVDYWGQGTLVTVSSASTKGP<br>SVFPLAPCSRSTSESTAALGCLVKDYFPEPVTVSWNSGALTS<br>GVHTFPAVLQSSGLYSLSSVVTVPSSSLGTKTYTCNVDHKPS<br>NTKVDKRVESKYGPPCPPCPAPEAAGGPSVFLFPPKPKDTLM<br>ISRTPEVTCVVVDVSQEDPEVQFNWYVDGVEVHNAKTKPREE<br>QFNSTYRVVSVLTVLHQDWLNGKEYKCKVSNKGLPSSIEKTI<br>SKAKGQPREPQVYTLPPSQEEMTKNQVSLSCAVKGFYPSDIA<br>VEWESNGQPENNYKTTPPVLDSDGSFFLVSRLTVDKSRWQEG<br>NVFSCSVMHEALHNRFTQKSLSLSLGK |
| | Light Chain 1<br>B17B21<br>(SEQ ID NO: 14) | DIQMTQSPSSLSASVGDRVTITCRSSQSLVHSNGNTYLHWYQ<br>QKPGKAPKFLIYKVSNRFSGVPSRFSGSGSGTDFTLTISSLQ<br>PEDFATYYCSQSTHVPPTFGQGTKLEIKRTVAAPSVFIFPPS<br>DEQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC |

TABLE 8-continued

Heavy and Light Chain Sequences for Vβ17 bispecific antibodies

| Bispecific Antibody | | Amino Acid Sequence |
|---|---|---|
| | Heavy chain 2 Null (SEQ ID NO: 17) | QITLKESGPTLVKPTQTLTLTCTFSGFSLSTSGMGVSWIRQP PGKALEWLAHIYWDDDKRYNPSLKSRLTITKDTSKNQVVLTM TNMDPVDTATYYCARLYGFTYGFAYWGQGTLVTVSSASTKGP SVFPLAPCSRSTSESTAALGCLVKDYFPEPVTVSWNSGALTS GVHTFPAVLQSSGLYSLSSVVTVPSSSLGTKTYTCNVDHKPS NTKVDKRVESKYGPPCPPCPAPEAAGGPSVFLFPPKPKDTLM ISRTPEVTCVVVDVSQEDPEVQFNWYVDGVEVHNAKTKPREE QFNSTYRVVSVLTVLHQDWLNGKEYKCKVSNKGLPSSIEKTI SKAKGQPREPQVYTLPPSQEEMTKNQVSLWCLVKGFYPSDIA VEWESNGQPENNYKTTPPVLDSDGSFFLYSRLTVDKSRWQEG NVFSCSVMHEALHNHYTQKSLSLSLGK |
| | Light Chain 2 Null (SEQ ID NO: 18) | DIVMTQSPDSLAVSLGERATINCRASQSVDYNGISYMHWYQQ KPGQPPKLLIYAASNPESGVPDRFSGSGSGTDFTLTISSLQA EDVAVYYCQQIIEDPWTFGQGTKVEIKRTVAAPSVFIFPPSD EQLKSGTASVVCLLNNFYPREAKVQWKVDNALQSGNSQESVT EQDSKDSTYSLSSTLTLSKADYEKHKVYACEVTHQGLSSPVT KSFNRGEC |

Figure 3:
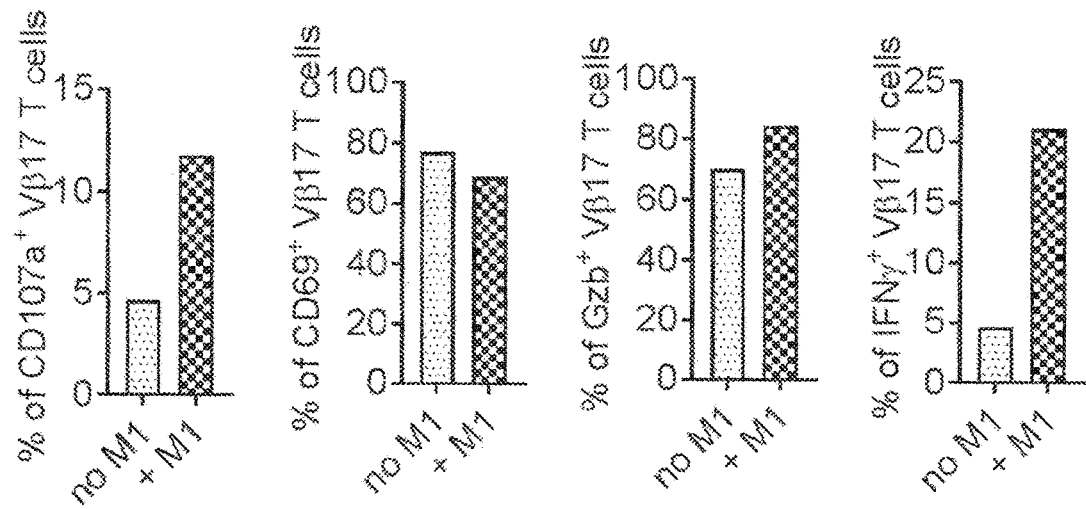
FIG. 3 shows Vβ17+CD8+ T cells have hallmarks of killer cytotoxic cells. Bar graph indicates expression of CD107a, CD69, Granzyme B (Gzb) and Interferon-γ (IFNγ) on gated PBMCs for CD8+ T cells expressing Vβ17 (Vβ17+) on the cell surface at day 0 (no M1) and at day 14 after stimulation with M1 peptide (+M1).
Figure 4:
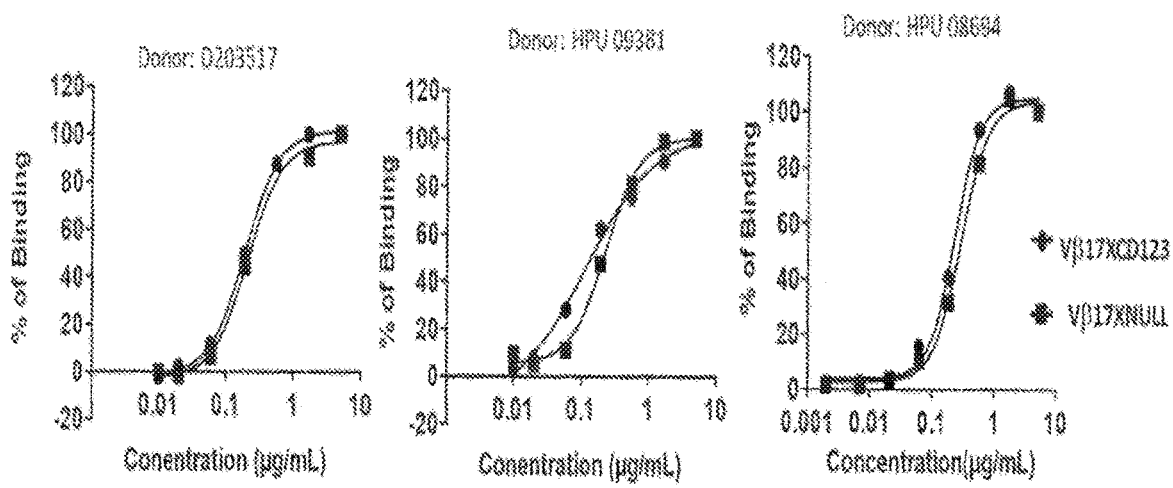
FIG. 4 shows binding of VB11 [anti-Vβ17/anti-CD123] bispecific as well as VB13 [Vβ17 null control bispecific] antibodies to CD8+ T cells. Data presented from CD8+ T cells isolated from PBMCs from 3 different donors (D203517, HPU09381 and HPU08694). The table below each graph presents $EC_{50}$ values for binding in nM.
Figure 5:
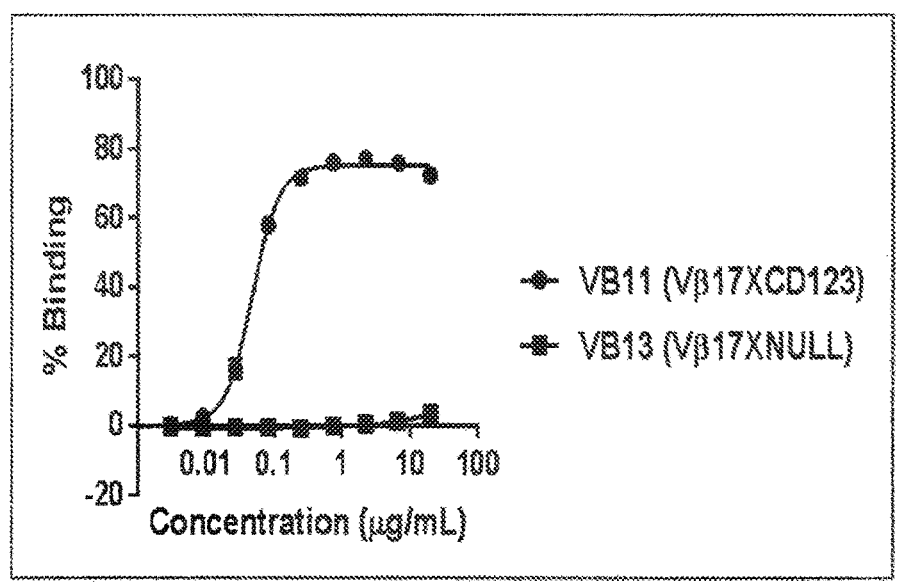
FIG. 5 shows binding of Vβ17 and CD123 bispecific (VB11) as well as Vβ17 null control bispecific (VB13) antibodies to AML cancer cell line. Data presented shows binding of bispecific antibodies to Kasumi3 AML cell line. The table below the graph presents $EC_{50}$ values for binding in nM.
Figure 6:
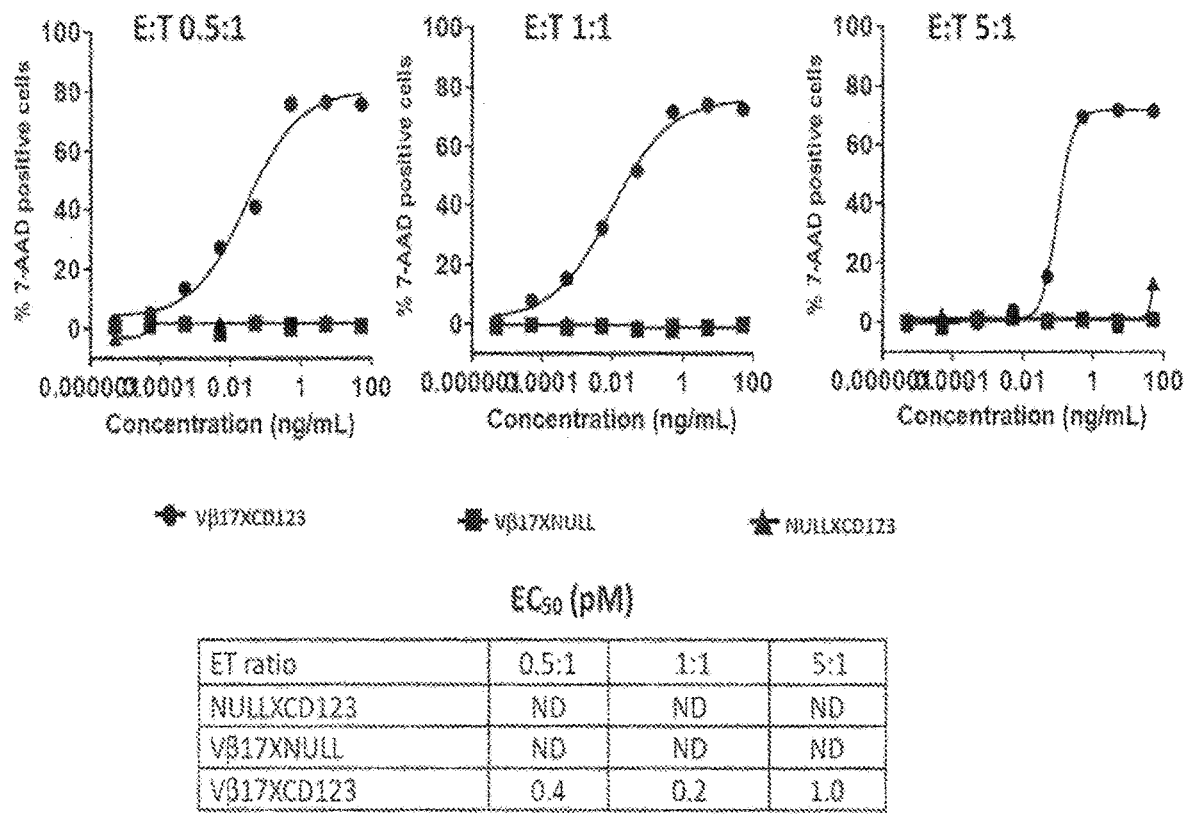
FIG. 6 shows redirection of Vβ17+ T cells by bispecific antibodies that induce efficient killing of AML cancer cells. Data in the left graph shows killing of Kasumi3 cancer cells at an effector to target (E:T) ratio 0.5:1 and dose titration of bispecific antibodies. Data in the middle graph shows killing of Kasumi3 cancer cells at an E:T ratio 1:1 and dose titration of bispecific antibodies. Data in the right graph shows killing of Kasumi3 cancer cells at an E:T ratio 5:1 and dose titration of bispecific antibodies. The table below the graphs shows $EC_{50}$ values calculated from the above graphs given in pM.
Figure 7A:
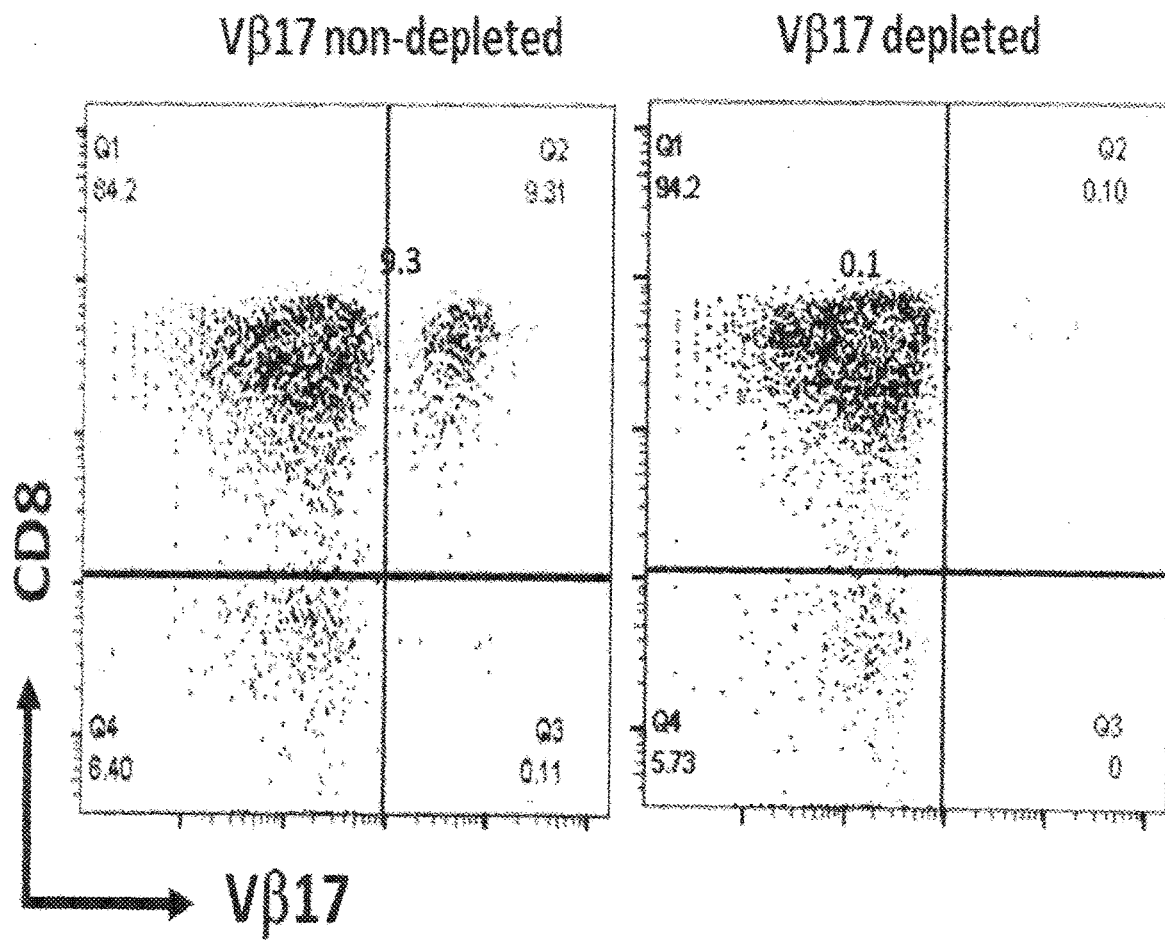
FIGS. 7A-7B show specific binding of an anti-Vβ17/anti-CD123 bispecific antibody (VB11) and a Vβ17 null bispecific antibody (VB13) to CD8+ T cells isolated from PBMCs.
Figure 7B:
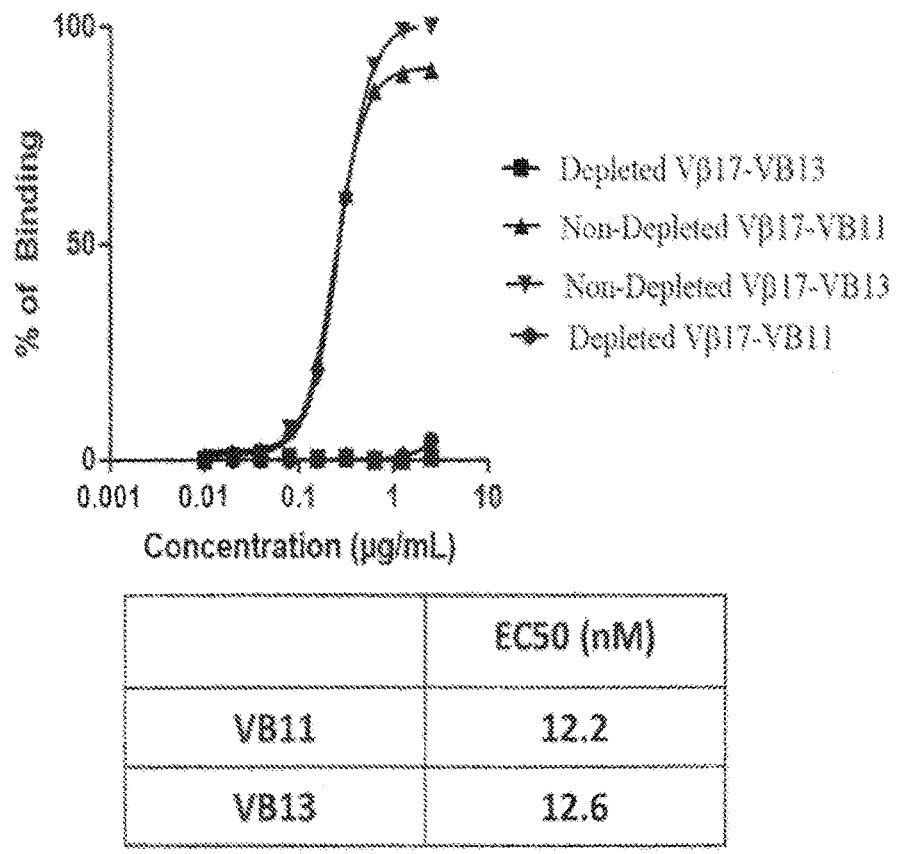
Figure 8:
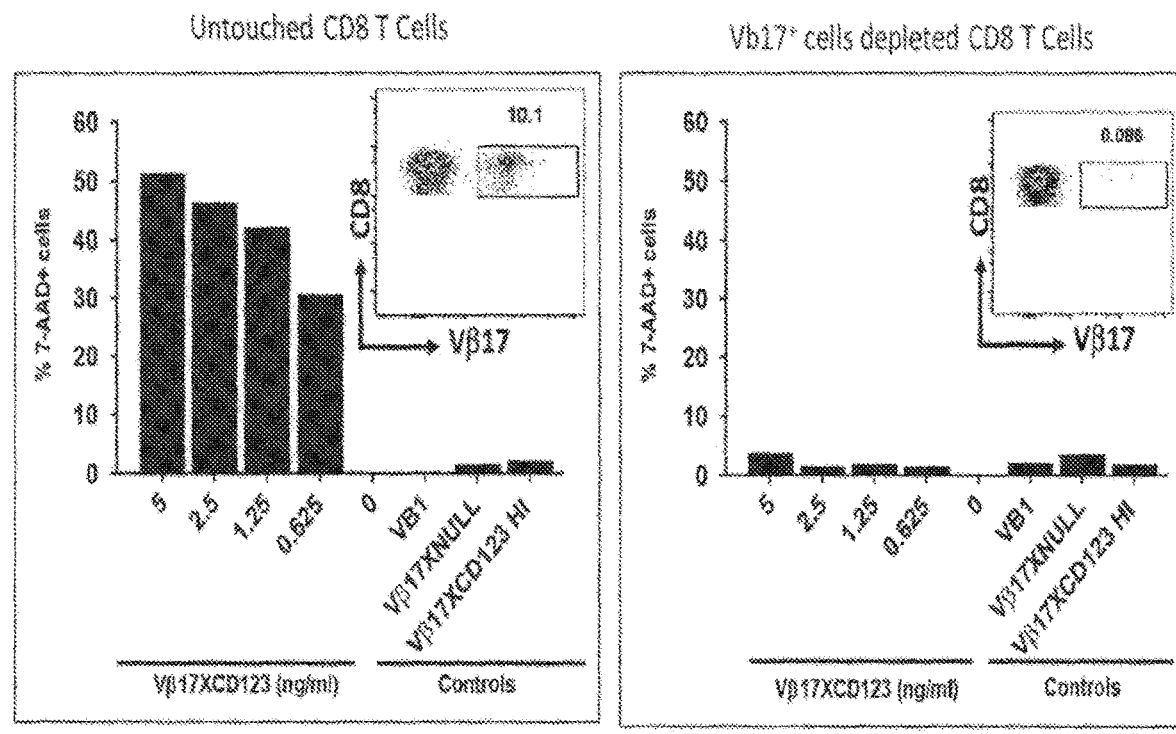
FIG. 8 shows specific recruitment of Vβ17 T cells by a Vβ17-bispecific antibody for killing of Kasumi3 cancer cells. Left figure shows killing of Kasumi3 AML cell line when effectors cells were isolated from PBMCs containing CD8+ T cells expressing Vβ17 (Vβ17+) on the cell surface (untouched CD8 T cells). Insert shows presence of 10.1% Vβ17+CD8 T cells in the effector cell population. Right figure shows killing of Kasumi3 AML cell line when effector CD8+ T cells were isolated from PBMCs, but Vβ17+ T cells were depleted by negative selection. Insert shows presence of a minor population (0.086%) Vβ17+CD8+ T cells in the effector cell population.
Figure 9A:
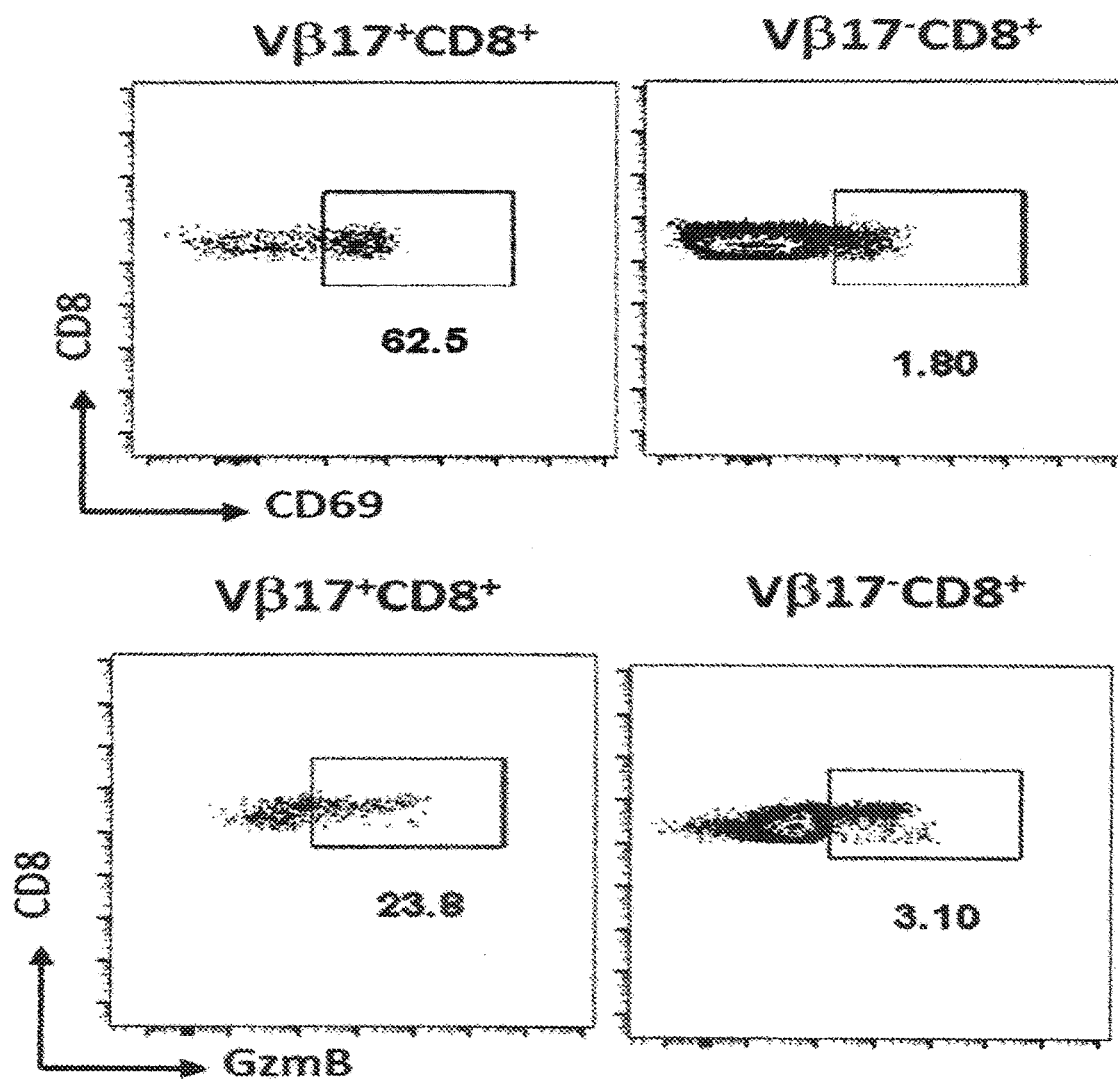
FIGS. 9A-9B show that there is no pan activation of T cells when using Vβ17 bispecific antibodies.
Figure 9B:
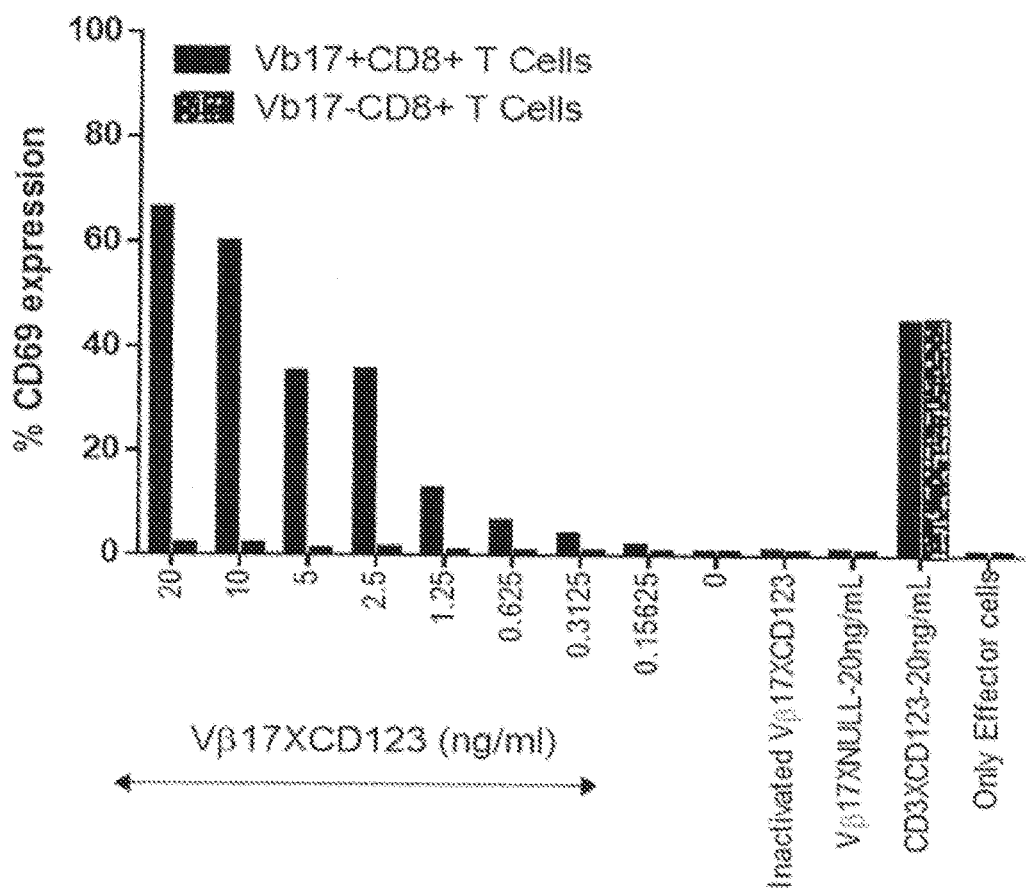
Figure 10:
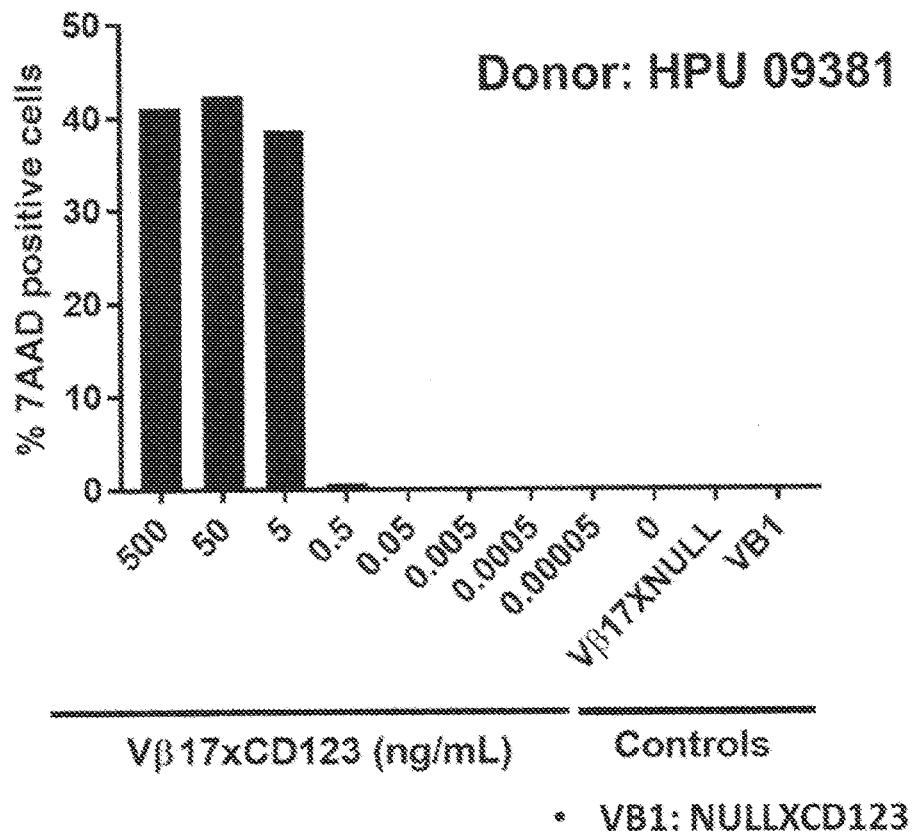
FIG. 10 shows that Vβ17+ T cells from HLA A2 negative donor are also effector killer cells and no pre-stimulation of Vβ17+ cell required. Efficient cytotoxicity mediated by Vβ17 bispecific antibody of Kasumi3 cancer cells is shown from PBMCs containing Vβ17+ T cells from HLA A2 negative donor (HPU 09381).

Example 3. Evaluation of Binding and Cytotoxic Properties of Anti-Vβ17/Anti-CD123 Bispecific Antibody Using Kasumi-3 Cells and Human CD8+ T Cells Stimulation and Expansion of Vβ17+ CD8+ T Cells from Total PBMCs To expand Vβ17+ CD8+ T cells, whole PBMCs from BILA-A2 donor (HPU-08694) were stimulated with 1 µg/mL FLU MP 58 peptide (in DMSO). Frequency of Vβ17+ cells among total CD8+ T cells was determined on day 8 and 14 of the culture period. To enumerate the frequency of Vβ17+ cells among total CD8+ T cells, total live PBMCs were initially gated, doublets were excluded, total CD8+ T cells were gated and then Vβ17+ cells were gated (FIG. 3A). Compared to the frequency of Vβ17+ cells among total CD8+ T cells on day 0, a substantial expansion of these cells were observed at day 8 of the culture period (FIG. 3B). A larger fraction of CD8+ T cells on day 8 were Vβ17+ cells (FIG. 3B) in this donor.

Anti-Vβ17/Anti-CD123 Bispecific Antibody Binding Assay On Kasumi-3 Cells

To understand the binding kinetics of the anti-Vβ17/anti-CD123 bispecific antibody, Kasumi-3 cells were incubated with the anti-Vβ17/anti-CD123 bispecific antibody and Vβ17×NULL arm control at various concentrations (concentration range from 5 µg/mL to 0 g/mL). Cell bound bispecific antibody was detected with mouse anti-human IgG4 Fc-PE secondary antibody. Table 9 shows the frequency of Kasumi-3 cells positive for PE (secondary antibody) when treated with different concentration of bispecific antibodies. The EC$_{50}$ for anti-Vβ17/anti-CD123 and NULLXCD123 was determined as 6 and 42.7 nM respectively (Table 9).

TABLE 9

Binding affinity of Kasumi-3 cells for bispecific antibodies.

| Conc.(ug/mL) | anti-Vβ17/ anti-CD123 | Vβ17XNULL | NULLXCD123 |
|---|---|---|---|
| 5 | 87.37 | −0.02 | 47.47 |
| 1.667 | 74.37 | 0.09 | 16.37 |
| 0.556 | 24.07 | 0.15 | 1.2 |
| 0.185 | 1.65 | 0.35 | 0.31 |

TABLE 9-continued

Binding affinity of Kasumi-3 cells for bispecific antibodies.

| Conc.(ug/mL) | anti-Vβ17/ anti-CD123 | Vβ17XNULL | NULLXCD123 |
|---|---|---|---|
| 0.062 | 0.32 | 0.12 | 0.04 |
| 0.021 | 0.16 | 0.14 | 0.05 |
| 0.007 | 0.23 | 0.19 | −0.06 |
| 0.002 | 0.04 | −0.09 | −0.04 |
| 0.001 | 0.09 | 0 | −0.18 |
| EC$_{50}$ (µg/mL) | 0.9 | ND | 6.4 |
| EC$_{50}$ (nM) | 6 | ND | 42.7 |

Bispecific antibody binding affinities to Kasumi-3 cells were determined by flow cytometry. Half maximal effective concentration (EC$_{50}$) values were calculated as the bispecific concentration that generates 50% of maximal Binding (PE positive cells). ND: Not determined.

On Enriched CD8+ T Cells

Enriched FLU MP 58 peptide stimulated CD8+ T (from day 14 culture) cells were incubated with various concentrations of anti-Vβ17/anti-CD123 bispecific and Vβ17× NULL arm control antibodies. Mouse anti-human IgG4 Fc-PE secondary antibody was used to detect the bispecific antibody. Table 10 shows the frequency of CD8+ T cells positive for PE (secondary antibody) when treated with different concentration of bispecific antibodies. The EC$_{50}$ for anti-Vβ17/anti-CD123, Vβ17×NULL, was determined as 9.0 nm, 18.7 nm respectively (Table 10).

TABLE 10

Binding activity of CD8+ T cell for bispecific antibodies.

| Conc.(µg/mL) | anti-Vβ17/ anti-CD123 | Vβ17XNULL | NULLXCD123 |
|---|---|---|---|
| 20 | 74.7 | 76.2 | 0.1 |
| 10 | 72.4 | 75.4 | 0.4 |
| 5 | 70.8 | 64.6 | 0.3 |
| 2.5 | 64.8 | 42.5 | 0.5 |
| 1.25 | 38.0 | 32.4 | 0.4 |
| 0.625 | 41.4 | 21.7 | −0.1 |
| 0.3125 | 26.5 | 11.8 | 0.8 |

TABLE 10-continued

Binding activity of CD8+ T cell for bispecific antibodies.

| Conc.(μg/mL) | anti-Vβ17/anti-CD123 | Vβ17XNULL | NULLXCD123 |
|---|---|---|---|
| 0.15625 | 19.9 | 3.4 | 0.6 |
| 0.078125 | 10.8 | 1.8 | 0.7 |
| EC$_{50}$ (μg/mL) | 1.35 | 2.80 | ND |
| EC$_{50}$ (nM) | 9 | 18.7 | ND |

Bispecific antibody binding affinities to CD8+ T cell were determined by flow cytometry. Half maximal effective concentration (EC$_{50}$) values were calculated as the antibody concentration that generates 50% of the maximal binding (PE positive cells). ND: Not Determined Bispecific Mediated Cytotoxicity Assay In order to analyze the potency of the anti-Vβ17/anti-CD123 bispecific antibody mediated cytotoxicity, CFSE labelled target (Kasumi-3) cells were co-cultured with stimulated CD8+ T cells (effectors) from day 14 of culture at an effector to target (ET) ratio 0.5:1, 1:1, 5:1 for 14 and 24 hours with various concentrations of anti-Vβ17/anti-CD123 bispecific and Vβ17xNULL arm control antibody. CD123 expression on target Kasumi-3 cells were checked by using a commercially available anti-CD123 antibody. Target cells (Kasumi-3) were labelled with CFSE to identify them as CFSE+ during flow cytometry analysis. Post co-culture period, 7-AAD was added to analyze the percentage of 7-AAD+ CFSE+ cells as a measure of cytotoxicity. Basal cytotoxicity observed in the absence of bispecific antibody was subtracted to obtain specific cytotoxicity in response to bispecific antibody. The assay was performed once with a single donor (HPU-08694). The EC$_{50}$ for the anti-Vβ17/anti-CD123 bispecific antibody at 0.5:1, 1:1 and 5:1 ET ratios for 14-hour time point were 3.7, 0.1 and 0.133 pM respectively (Table 11).

TABLE 11

Summary of EC$_{50}$ values for various bispecific antibodies upon co-culturing FLU MP 58 peptide stimulated CD8+ T cell with Kasumi-3 cells at ET ratios 0.5:1, 1:1 and 5:1 for 14 hours.

| | EC$_{50}$ (ng/mL) | | |
|---|---|---|---|
| Bispecific Ab | E:T Ratio (0.5:1) | E:T Ratio (1:1) | E:T Ratio (5:1) |
| NULLXCD123 | UD | UD | UD |
| Vβ17XNULL | UD | UD | UD |
| Anti-Vβ17/anti-CD123 | 0.55 | 0.015 | 0.02 |

| | EC$_{50}$ (pM) | | |
|---|---|---|---|
| Bispecific Ab | E:T Ratio (0.5:1) | E:T Ratio (1:1) | E:T Ratio (5:1) |
| NULLXCD123 | UD | UD | UD |
| Vβ17XNULL | UD | UD | UD |
| anti-Vβ17/anti-CD123 | 3.7 | 0.1 | 0.133 |

UD: Undetectable, as the activity was too low for proper curve fitting.

The EC$_{50}$ for the anti-Vβ17/anti-CD123 bispecific at 0.5:1, 1:1 and 5:1 ET ratio for 24-hour time point were 0.4, 0.2 and 1.0 pM respectively (Table 12).

TABLE 12

Summary of EC$_{50}$ values for various bispecific antibodies upon co-culturing FLU MP 58 peptide stimulated CD8+ T cells with Kasumi-3 cells at ET ratios 0.5:1, 1:1 and 5:1 for 24 hours.

| | EC$_{50}$ (ng/mL) | | |
|---|---|---|---|
| Bispecific Ab | E:T Ratio (0.5:1) | E:T Ratio (1:1) | E:T Ratio (5:1) |
| NULLXCD123 | UD | UD | UD |
| Vβ17XNULL | UD | UD | UD |
| anti-Vβ17/anti-CD123 | 0.06 | 0.03 | 0.15 |

| | EC$_{50}$ (pM) | | |
|---|---|---|---|
| Bispecific Ab | E:T Ratio (0.5:1) | E:T Ratio (1:1) | E:T Ratio (5:1) |
| NULLXCD123 | UD | UD | UD |
| Vβ17XNULL | UD | UD | UD |
| anti-Vβ17/anti-CD123 | 0.4 | 0.2 | 1.0 |

UD: Undetectable

Similarly, anti-Vβ17/anti-CD123 bispecific mediated unstimulated CD8 T cell cytotoxicity was tested at ET ratio 0.5:1, 1:1, 5:1 for 14 (Table 13) and 24 (Table 14) hours. At 5 ng/ml anti-Vβ17/anti-CD123 bispecific concentration and 14-hour time point, unstimulated CD8+ T cells at 0.5:1 and 1:1 ET ratio showed 2.8% and 9.8% target cell cytotoxicity respectively (Table 13), compared to 77% and 73% cytotoxicity by stimulated CD8 T cells. At 5:1 ET ratio, unstimulated CD8+ T cells exhibited 31.65% target cytotoxicity, compared to 70.9% by stimulated CD8+ T cells. Similar results were obtained from 24-hour time point (Table 12, 15, 16, and 17). At highest concentration (5 ng/ml) of anti-Vβ17/anti-CD123 bispecific tested, unstimulated CD8+ T cells exhibited higher cytotoxicity towards target cells at a higher ET ratio.

TABLE 13

Cytotoxicity assay with unstimulated CD8+ T cells at various ET ratios for 14 hours. Frequency of CFSE and 7-AAD positive cells when treated with different concentrations of bispecific antibodies.

| Bispecific Ab | Conc (ng/mL) | E:T Ratio (0.5:1) | E:T Ratio (1:1) | E:T Ratio (5:1) |
|---|---|---|---|---|
| NULLXCD123 | 5 | 1.3 | −0.6 | −0.45 |
| | 0.005 | 1.3 | −0.5 | 0.45 |
| Vβ17XNULL | 5 | −0.6 | −0.8 | 3.25 |
| | 0.005 | −0.3 | 1 | −1.35 |
| anti-Vβ17/anti-CD123 | 5 | 2.8 | 9.8 | 31.65 |
| | 0.005 | 0.1 | 3.2 | 12.25 |

TABLE 14

Cytotoxicity assay with unstimulated CD8+ T cells at various ET ratios for 24 hours. Frequency of CFSE and 7-AAD positive cells when treated with different concentrations of bispecific antibodies.
Unstimulated CD8+ T cells

| Bispecific Ab | Conc (ng/mL) | E:T Ratio (0.5:1) | E:T Ratio (1:1) | E:T Ratio (5:1) |
|---|---|---|---|---|
| NULLXCD123 | 5 | −1.3 | −0.55 | −4.85 |
| | 0.005 | −2 | −0.85 | −2.95 |
| Vβ17XNULL | 5 | −0.8 | −1.35 | 10.85 |
| | 0.005 | −1 | −1.05 | −1.95 |
| anti-Vβ17/anti-CD123 | 5 | 4.8 | 11.55 | 30.65 |
| | 0.005 | 1.5 | 1.75 | 10.95 |

TABLE 15

Cytotoxicity assay at 0.5:1 ET ratio (stimulated CD8+ T cell: Kasumi-3 cells) upon incubation for 14 hrs. Frequency of CFSE and 7-AAD positive cells when treated with different concentrations of bispecific antibodies at 0.5:1 ET ratio for 14 hrs.

| Conc.(ng/mL) | NULLXCD123 | Vβ17XNULL | anti-Vβ17/anti-CD123 |
|---|---|---|---|
| 50 | 3.47 | 2.57 | 77.07 |
| 5 | 2.67 | 2.17 | 77.47 |
| 0.5 | −0.73 | 1.87 | 46.77 |
| 0.05 | 0.77 | 1.67 | 3.77 |
| 0.005 | −0.03 | 1.47 | 1.97 |
| 0.0005 | 0.67 | 1.07 | 2.17 |
| 0.00005 | 1.67 | 0.17 | 0.17 |
| 0.000005 | −0.43 | 3.27 | 0.87 |
| $EC_{50}$ (ng/mL) | ND | ND | 0.55 |
| $EC_{50}$ (pM) | ND | ND | 3.7 |

Half maximal effective concentration ($EC_{50}$) values were calculated as the antibody concentration that generates 5000 of maximal cytotoxicity (CFSE+ 7AAD+) cells. ND: Not Determined.

TABLE 16

Cytotoxicity assay at 1:1 ET ratio (stimulated CD8+ T cell: Kasumi-3 cells) upon incubation for 14 hrs. Frequency of CFSE and 7-AAD positive cells when treated with different concentrations of bispecific antibodies at 11 ET ratio for 14 hrs.

| Conc.(ng/mL) | NULLXCD123 | Vβ17XNULL | anti-Vβ17/anti-CD123 |
|---|---|---|---|
| 50 | 0.6 | −0.5 | 76.0 |
| 5 | 0.1 | 0.9 | 73.0 |
| 0.5 | 1.0 | 0.9 | 77.9 |
| 0.05 | 0.4 | 1.8 | 59.4 |
| 0.005 | 1.8 | 0.9 | 36.8 |
| 0.0005 | 0.9 | 1.1 | 18.0 |
| 0.00005 | 0.7 | 0.9 | 6.1 |
| 0.000005 | 1.6 | 0.8 | 1.9 |
| $EC_{50}$ (ng/mL) | ND | ND | 0.015 |
| $EC_{50}$ (pM) | ND | ND | 0.1 |

Half maximal effective concentration ($EC_{50}$) values were calculated as the antibody concentration that generates 50% of maximal cytotoxicity (CFSE+ 7AAD+) cells. ND: Not Determined

TABLE 17

Cytotoxicity assay at 5:1 E:T ratio (stimulated CD8+ T cell: Kasumi-3 cells) upon incubation for 14 hrs. Frequency of CFSE and 7-AAD positive cells when treated with different concentrations of bispecific antibodies at 5:1 ET ratio for 14 hrs.

| Conc.(ng/mL) | NULLXCD123 | Vβ17XNULL | anti-Vβ17/anti-CD123 |
|---|---|---|---|
| 50 | 2.3 | 0.0 | 70.2 |
| 5 | 3.1 | 2.7 | 70.9 |
| 0.5 | 1.8 | 4.4 | 74.5 |
| 0.05 | 3.0 | 1.5 | 73.2 |
| 0.005 | 2.1 | 1.6 | 2.5 |
| 0.0005 | 2.9 | 3.5 | 1.4 |
| 0.00005 | 3.2 | 5.5 | 2.5 |
| 0.000005 | 4.1 | 4.4 | 4.8 |
| $EC_{50}$ (ng/mL) | UD | UD | 0.02 |
| $EC_{50}$ (pM) | UD | UD | 0.13 |

Half maximal effective concentration ($EC_{50}$) values were calculated as the antibody concentration that generates 50% of maximal cytotoxicity (CFSE+ 7AAD+) cells. UD: Undetectable.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

| SEQ ID NO: | Type | Species | Description | Sequence |
|---|---|---|---|---|
| 1 | PRT | mouse | B17B01-HCDR1 | GYSITSGYFWN |
| 2 | PRT | mouse | B12B01-HCDR2 | YISYDGSNN |
| 3 | PRT | mouse | B12B01-HCDR3 | PSPGTGYAVDY |
| 4 | PRT | mouse | B17B01-LCDR1 | RSSQSLVHSNGNTYLH |
| 5 | PRT | mouse | B12B01-LCDR2 | KVSNRFS |
| 6 | PRT | mouse | B12B01-LCDR2 | SQSTHVPFT |
| 7 | PRT | mouse | B17B01-HC | NVQLQESGPGLVKPSQSLSLTCSVAGYSITSGYFWNWIRQFPGNKLEWMGY ISYDGSNNYNPSLKNRISITRDTSKNQFFLKLNSVTTEDTATYYCASPSPG TGYAVDYWGQGTSVTVSSAKTTPPSVYPLAPGSAAQTNSMVTLGCLVKGYF PEPVTVTWNSGSLSSGVHTFPAVLQSDLYTLSSSVTVPSSTWPSQTVTCNV AHPASSTKVDKKIVPRDCGCKPCICTVPEVSSVFIFPPKPKDVLTITLTPK VTCVVVDISKDDPEVQFSWFVDDVEVHTAQTKPREEQINSTFRSVSELPIM HQDWLNGKEFKCRVNSAAFPAPIEKTISKTYGRPKAPQVYTIPPPKEQMAK DKVSLTCMITNFFPEDITVEWQWNGQPAENYKNTQPIMDTDGSYFVYSKLN VQKSNWEAGNTFTCSVLHEGLHNHHTEKSLSHSPGK |

| SEQ ID NO: | Type | Species | Description | Sequence |
|---|---|---|---|---|
| 8 | PRT | mouse | B17B01-LC | NVVMTQTPLSLPVSLGDQASISCRSSQSLVHSNGNTYLHWYLQKPGQSPKF LIYKVSNRFSGVPDRFSGGGSGTEFTLKISRVEAEDLGVYFCSQSTHVPFT FGSGTKLEIKRADAAPTVSIFPPSSEQLTSGGASVVCFLNNFYPKDINVKW KIDGSERQNGVLNSWTDQDSKDSTYSMSSTLTLTKDEYERHNSYTCEATHK TSTSPIVKSFNRNEC |
| 9 | PRT | mouse | B17B1-HC | NVQLQESGPGLVKPSQSLSLTCSVAGYSITSGYFWNWIRQFPGNKLEWMGY ISYDGSNNYNPSLKNRISITRDTSKNQFFLKLNSVTTEDTATYYCASPSPG TGYAVDYWGQGTSVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEAAGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFLLYS KLTVDKSRWQEGNVFSCSVMHEALHNHYTQKSLSLSLGK |
| 10 | PRT | mouse | B17B1-LC | NVVMTQTPLSLPVSLGDQASISCRSSQSLVHSNGNTYLHWYLQKPGQSPKF LIYKVSNRFSGVPDRFSGGGSGTEFTLKISRVEAEDLGVYFCSQSTHVPFT FGSGTKLEIKRADAAPTVSIFPPSSEQLTSGGASVVCFLNNFYPKDINVKW KIDGSERQNGVLNSWTDQDSKDSTYSMSSTLTLTKDEYERHNSYTCEATHK TSTSPIVKSFNRNEC |
| 11 | PRT | mouse | B17B2-HC | DVQLKESGPGLVKPSQSLSVTCSVTGYSITSGYYWNWYRQFPGNKLEWMGY ISYDGSNNYNPSLKNRISITRDTSKNQILLKLTYVTTEDTATYYCTRPSPG TGYAVDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEAAGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFLLYS KLTVDKSRWQEGNVFSCSVMHEALHNHYTQKSLSLSLGK |
| 12 | PRT | mouse | B17B2-LC | DIVMTQSPDSLAVSLGERATINCRSSQSLVHSNGNTYLHWYQQKPGQPPKL LIYKVSNRFSGVPDRFSGSGSGTDFTLTISSLQAEDVAVYYCSQSTHVPFT FGQGTKVEIKRADAAPTVSIFPPSSEQLTSGGASVVCFLNNFYPKDINVKW KIDGSERQNGVLNSWTDQDSKDSTYSMSSTLTLTKDEYERHNSYTCEATHK TSTSPIVKSFNRNEC |
| 13 | PRT | artificial | B17B21-HC | QVQLQESGPGLVKPSETLSLTCTVSGYSITSGYFWNWIRQPPGKGLEWIGY ISYDGSNNYNPSLKSRVTISRDTSKNQFSLKLSSVTAADTAVYYCASPSPG TGYAVDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEAAGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLSCAVKGFYPSDIAVEWESNGQPENNYKTTPPVLDSDGSFFLVS RLTVDKSRWQEGNVFSCSVMHEALHNRFTQKSLSLSLGK |
| 14 | PRT | artificial | B17B21-LC | DIQMTQSPSSLSASVGDRVTITCRSSQSLVHSNGNTYLHWYQQKPGKAPKF LIYKVSNRFSGVPSRFSGSGSGTDFTLTISSLQPEDFATYYCSQSTHVPFT FGQGTKLEIKRTVAAPSVFIFPPSDEQLKSGTASVVCLLNNFYPREAKVQW KVDNALQSGNSQESVTEQDSKDSTYSLSSTLTLSKADYEKHKVYACEVTHQ GLSSPVTKSFNRGEC |
| 15 | PRT | human | I3RB217-HC | EVQLVQSGAEVKKPGESLKISCKGSGYSFTSYWISWVRQMPGKGLEWMGII DPSDSDTRYSPSFQGQVTISADKSISTAYLQWSSLKASDTAMYYCARGDGS TDLDYWGQGTLVTVSSASTKGPSVFPLAPCSRSTSESTAALGCLVKDYFPE PVTVSWNSGALTSGVHTFPAVLQSSGLYSLSSVVTVPSSSLGTKTYTCNVD HKPSNTKVDKRVESKYGPPCPPCPAPEAAGGPSVFLFPPKPKDTLMISRTP EVTCVVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQEEMT KNQVSLWCLVKGFYPSDIAVEWESNGQPENNYKTTPPVLDSDGSFFLYSRL TVDKSRWQEGNVFSCSVMHEALHNHYTQKSLSLSLGK |
| 16 | PRT | human | I3RB217-LC | EIVLTQSPGTLSLSPGERATLSCRASQSVSSSYLAWYQQKPGQAPRLLIYG ASSRATGIPDRFSGSGSGTDFTLTISRLEPEDFAVYYCQQDYGFPWTFGQG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 17 | PRT | human | Null-HC | QITLKESGPTLVKPTQTLTLTCTFSGFSLSTSGMGVSWIRQPPGKALEWLA HIYWDDDKRYNPSLKSRLTITKDTSKNQVVLTMTNMDPVDTATYYCARLYG FTYGFAYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEAAGGPSVFLFPPKPKDTLMISR |

| SEQ ID NO: | Type | Species | Description | Sequence |
|---|---|---|---|---|
| | | | | TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLWCLVKGFYPSDIAVEWESNGQPENNYKTTPPVLDSDGSFFLYS RLTVDKSRWQEGNVFSCSVMHEALHNHYTQKSLSLSLGK |
| 18 | PRT | human | Null-LC | DIVMTQSPDSLAVSLGERATINCRASQSVDYNGISYMHWYQQKPGQPPKLL IYAASNPESGVPDRFSGSGSGTDFTLTISSLQAEDVAVYYCQQIIEDPWTF GQGTKVEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 19 | PRT | artificial | B17H3 | EVQLLESGGGLVQPGGSLRLSCAASGYSITSGYFWNWVRQAPGKGLEWVS YISYDGSNNYADSVKGRFTISRDNSKNTLYLQMNSLRAEDTAVYYCAKPS PGTGYAVDYWGQGTLVTVS |
| 20 | PRT | artificial | B17H4 | EVQLLESGGGLVQPGGSLRLSCAASGYSITSGYFWNWVRQAPGKGLEWVSY ISYDGSNNYADSVKGRFTISRDNSKNTLYLQMNSLRAEDTAVYYCASPSPG TGYAVDYWGQGTLVTVSS |
| 21 | PRT | artificial | B17H5 | QVQLQESGPGLVKPSETLSLTCTVSGYSITSGYFWNWIRQPPGKGLEWIGY ISYDGSNNYNPSLKSRVTISRDTSKNQFSLKLSSVTAADTAVYYCASPSPG TGYAVDYWGQGTLVTVSS |
| 22 | PRT | artificial | B17L3 | DIQMTQSPSSLSASVGDRVTITCRSSQSLVHSNGNTYLHWYQQKPGKAPKL LIYKVSNRFSGVPSRFSGSGSGTDFTLTISSLQPEDFATYYCSQSTHVPFT FGQGTKLEIK |
| 23 | PRT | artificial | B17L4 | DIQMTQSPSSLSASVGDRVTITCRSSQSLVHSNGNTYLHWYQQKPGKAPKF LIYKVSNRFSGVPSRFSGSGSGTDFTLTISSLQPEDFATYYCSQSTHVPFT FGQGTKLEIK |
| 24 | PRT | artificial | B17L5 | DVVMTQSPLSLPVTLGQPASISCRSSQSLVHSNGNTYLHWFQQRPGQSPRF LIYKVSNRFSGVPDRFSGSGSGTDFTLKISRVEAEDVGVYYCSQSTHVPFT FGQGTKLEIK |
| 25 | PRT | artificial | B17H1 | NVQLQESGPGLVKPSQSLSLTCSVAGYSITSGYFWNWIRQFPGNKLEWMGY ISYDGSNNYNPSLKNRISITRDTSKNQFFLKLNSVTTEDTATYYCASPSPG TGYAVDYWGQGTSVTVSS |
| 26 | PRT | artificial | B17L1 | NVVMTQTPLSLPVSLGDQASISCRSSQSLVHSNGNTYLHWYLQKPGQSPKF LIYKVSNRFSGVPDRFSGGGSGTEFTLKISRVEAEDLGVYFCSQSTHVPFT FGSGTKLEIK |
| 27 | PRT | human | TCR-Vβ17 | MAWVWTLLFLMAAAQSIQAVDGGITQSPKYLFRKEGQNVTLSCEQNLNHDA MYWYRQDPGQGLRLIYYSQIVNDFQKGDIAEGYSVSREKKESFPLTVTSAQ KNPTAFYLCASSSRSSYEQYFGPGTRLTVTEDLKNVFPPEVAVFEPSEAEI SHTQKATLVCLATGFYPDHVELSWWVNGKEVHSGVSTDPQPLKEQPALNDS RYSLSSRLRVSATFWQNPRNHFRCQVQFYGLSENDEWTQDRAKPVTQIVSA EAAWGRADepkscdkthtcppcpapeLLggpsvflfppkpkdtlmisrtpev tcvvvDvshedpevkfnwyvdgvevhnaktkpreeqynstyrvvsyltvlh qdwhigkeykckvsnkalpapiektiskakgqprepqvyLppsreemtlm qvslLclvkgfypsdiavewesngqpennyLtWppvldsdgsfflyskltv dksnvqqgnvfscsvmhealhnhytqkslslspg |
| 28 | PRT | artificial | B17B21 half antibody | MAWVWTLLFLMAAAQSIQADIQMTQSPSSLSASVGDRVTITCRSSQSLVHS NGNTYLHWYQQKPGKAPKFLIYKVSNRFSGVPSRFSGSGSGTDFTLTISSL QPEDFATYYCSQSTHVPFTFGQGTKLEIKRTVAAPSVFIFPPSDEQLKSGT ASVVCLLNNFYPREAKVQWKVDNALQSGNSQESVTEQDSKDSTYSLSSTLT LSKADYEKHKVYACEVTHQGLSSPVTKSFNRGECGGSEGKSSGSGSESKST EGKSSGSGSESKSTGGSQVQLQESGPGLVKPSETLSLTCTVSGYSITSGYF WNWIRQPPGKGLEWIGYISYDGSNNYNPSLKSRVTISRDTSKNQFSLKLSS VTAADTAVYYCASPSPGTGYAVDYWGQGTLVTVSSASTKGPSVFPLAPCSR STSESTAALGCLVKDYFPEPVTVSWNSGALTSGVHTFPAVLQSSGLYSLSS VVTVPSSSLGTKTYTCNVDHKPSNTKVDKRVESKYGPPCPPCPAPEAAGGP SVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAK GQPREPQVYTLPPSQEEMTKNQVSLSCAVKGFYPSDIAVEWESNGQPENNY KTTPPVLDSDGSFFLVSRLTVDKSRWQEGNVFSCSVMHEALHNRFTQKSLS LSLGK |
| 29 | DNA | artificial | B17B21 half antibody | ATGGCCTGGGTGTGGACCCTGCTGTTCCTGATGGCCGCCGCCCAGAGCATC CAGGCCGACATCCAGATGACCCAGAGCCCAAGCAGCCTGAGCGCCAGCGTG GGCGACCGCGTGACCATCACCTGCCGCAGCAGCCAGAGCCTGGTGCACAGC AACGGCAACACCTACCTGCACTGGTACCAGCAGAAGCCAGGCAAGGCCCCA AAGTTCCTGATCTACAAGGTGAGCAACCGCTTCAGCGGCGTGCCAAGCCGC TTCAGCGGCAGCGGCAGCGGCACCGACTTCACCCTGACCATCAGCAGCCTG |

| SEQ ID NO: | Type | Species | Description | Sequence |
|---|---|---|---|---|
| | | | | CAGCCAGAGGACTTCGCCACCTACTACTGCAGCCAGAGCACCCACGTGCCA |
| | | | | TTCACCTTCGGCCAGGGCACCAAGCTGGAGATCAAGCGCACCGTGGCCGCC |
| | | | | CCAAGCGTGTTCATCTTCCCACCAAGCGACGAGCAGCTGAAGAGCGGCACC |
| | | | | GCCAGCGTGGTGTGCCTGCTGAACAACTTCTACCCACGCGAGGCCAAGGTG |
| | | | | CAGTGGAAGGTGGACAACGCCCTGCAGAGCGGCAACAGCCAGGAGAGCGTG |
| | | | | ACCGAGCAGGACAGCAAGGACAGCACCTACAGCCTGAGCAGCACCCTGACC |
| | | | | CTGAGCAAGGCCGACTACGAGAAGCACAAGGTGTACGCCTGCGAGGTGACC |
| | | | | CACCAGGGCCTGAGCAGCCCAGTGACCAAGAGCTTCAACCGCGGCGAGTGC |
| | | | | GGCGGCAGCGAGGGCAAGAGCAGCGGCAGCGGCAGCGAGAGCAAGAGCACC |
| | | | | GAGGGCAAGAGCAGCGGCAGCGGCAGCGAGAGCAAGAGCACCGGCGGCAGC |
| | | | | CAGGTGCAGCTGCAGGAGAGCGGCCCAGGCCTGGTGAAGCCAAGCGAGACC |
| | | | | CTGAGCCTGACCTGCACCGTGAGCGGCTACAGCATCACCAGCGGCTACTTC |
| | | | | TGGAACTGGATCCGCCAGCCACCAGGCAAGGGCCTGGAGTGGATCGGCTAC |
| | | | | ATCAGCTACGACGGCAGCAACAACTACAACCCAAGCCTGAAGAGCCGCGTG |
| | | | | ACCATCAGCCGCGACACCAGCAAGAACCAGTTCAGCCTGAAGCTGAGCAGC |
| | | | | GTGACCGCCGCCGACACCGCCGTGTACTACTGCGCGCAGCCCAAGCCCAGGC |
| | | | | ACCGGCTACGCCGTGGACTACTGGGGCCAGGGCACCCTGGTGACCGTGAGC |
| | | | | AGCGCCAGCACCAAGGGCCCAAGCGTGTTCCCACTGGCCCCATGCAGCCGC |
| | | | | AGCACCAGCGAGAGCACCGCCGCCCTGGGCTGCCTGGTGAAGGACTACTTC |
| | | | | CCAGAGCCAGTGACCGTGAGCTGGAACAGCGGCGCCCTGACCAGCGGCGTG |
| | | | | CACACCTTCCCAGCCGTGCTGCAGAGCAGCGGCCTGTACAGCCTGAGCAGC |
| | | | | GTGGTGACCGTGCCAAGCAGCAGCCTGGGCACCAAGACCTACACCTGCAAC |
| | | | | GTGGACCACAAGCCAAGCAACACCAAGGTGGACAAGCGCGTGGAGAGCAAG |
| | | | | TACGGCCCACCATGCCCACCATGCCCAGCCCCAGAGGCCGCCGGCGGCCCA |
| | | | | AGCGTGTTCCTGTTCCCACCAAAGCCAAAGGACACCCTGATGATCAGCCGC |
| | | | | ACCCCAGAGGTGACCTGCGTGGTGGTGGACGTGAGCCAGGAGGACCCAGAG |
| | | | | GTGCAGTTCAACTGGTACGTGGACGGCGTGGAGGTGCACAACGCCAAGACC |
| | | | | AAGCCACGCGAGGAGCAGTTCAACAGCACCTACCGCGTGGTGAGCGTGCTG |
| | | | | ACCGTGCTGCACCAGGACTGGCTGAACGGCAAGGAGTACAAGTGCAAGGTG |
| | | | | AGCAACAAGGGCCTGCCAAGCAGCATCGAGAAGACCATCAGCAAGGCCAAG |
| | | | | GGCCAGCCACGCGAGCCACAGGTGTACACCCTGCCACCAAGCCAGGAGGAG |
| | | | | ATGACCAAGAACCAGGTGAGCCTGAGCTGCGCCGTGAAGGGCTTCTACCCA |
| | | | | AGCGACATCGCCGTGGAGTGGGAGAGCAACGGCCAGCCAGAGAACAACTAC |
| | | | | AAGACCACCCCACCAGTGCTGGACAGCGACGGCAGCTTCTTCCTGGTGAGC |
| | | | | CGCCTGACCGTGGACAAGAGCCGCTGGCAGGAGGGCAACGTGTTCAGCTGC |
| | | | | AGCGTGATGCACGAGGCCCTGCACAACCGCTTCACCCAGAAGAGCCTGAGC |
| | | | | CTGAGCCTGGGCAAGATGGCCTGGGTGTGGACCCTGCTGTTCCTGATGGCC |
| | | | | GCCGCCCAGAGCATCCAGGCCGACATCCAGATGACCCAGAGCCCAAGCAGC |
| | | | | CTGAGCGCCAGCGTGGGCGACCGCGTGACCATCACCTGCCGCGCAGCAGCCAG |
| | | | | AGCCTGGTGCACAGCAACGGCAACACCTACCTGCACTGGTACCAGCAGAAG |
| | | | | CCAGGCAAGGCCCCAAAGTTCCTGATCTACAAGGTGAGCAACCGCTTCAGC |
| | | | | GGCGTGCCAAGCCGCTTCAGCGGCAGCGGCAGCGGCACCGACTTCACCCTG |
| | | | | ACCATCAGCAGCCTGCAGCCAGAGGACTTCGCCACCTACTACTGCAGCCAG |
| | | | | AGCACCCACGTGCCATTCACCTTCGGCCAGGGCACCAAGCTGGAGATCAAG |
| | | | | CGCACCGTGGCCGCCCCAAGCGTGTTCATCTTCCCACCAAGCGACGAGCAG |
| | | | | CTGAAGAGCGGCACCGCCAGCGTGGTGTGCCTGCTGAACAACTTCTACCCA |
| | | | | CGCGAGGCCAAGGTGCAGTGGAAGGTGGACAACGCCCTGCAGAGCGGCAAC |
| | | | | AGCCAGGAGAGCGTGACCGAGCAGGACAGCAAGGACAGCACCTACAGCCTG |
| | | | | AGCAGCACCCTGACCCTGAGCAAGGCCGACTACGAGAAGCACAAGGTGTAC |
| | | | | GCCTGCGAGGTGACCCACCAGGGCCTGAGCAGCCCAGTGACCAAGAGCTTC |
| | | | | AACCGCGGCGAGTGCGGCGGCAGCGAGGGCAAGAGCAGCGGCAGCGGCAGC |
| | | | | GAGAGCAAGAGCACCGAGGGCAAGAGCAGCGGCAGCGGCAGCGAGAGCAAG |
| | | | | AGCACCGGCGGCAGCCAGGTGCAGCTGCAGGAGAGCGGCCCAGGCCTGGTG |
| | | | | AAGCCAAGCGAGACCCTGAGCCTGACCTGCACCGTGAGCGGCTACAGCATC |
| | | | | ACCAGCGGCTACTTCTGGAACTGGATCCGCCAGCCACCAGGCAAGGGCCTG |
| | | | | GAGTGGATCGGCTACATCAGCTACGACGGCAGCAACAACTACAACCCAAGC |
| | | | | CTGAAGAGCCGCGTGACCATCAGCCGCGACACCAGCAAGAACCAGTTCAGC |
| | | | | CTGAAGCTGAGCAGCGTGACCGCCGCCGACACCGCCGTGTACTACTGCGCC |
| | | | | AGCCCAAGCCCAGGCACCGGCTACGCCGTGGACTACTGGGGCCAGGGCACC |
| | | | | CTGGTGACCGTGAGCAGCGCCAGCACCAAGGGCCCAAGCGTGTTCCCACTG |
| | | | | GCCCCATGCAGCCGCAGCACCAGCGAGAGCACCGCCGCCCTGGGCTGCCTG |
| | | | | GTGAAGGACTACTTCCCAGAGCCAGTGACCGTGAGCTGGAACAGCGGCGCC |
| | | | | CTGACCAGCGGCGTGCACACCTTCCCAGCCGTGCTGCAGAGCAGCGGCCTG |
| | | | | TACAGCCTGAGCAGCGTGGTGACCGTGCCAAGCAGCAGCCTGGGCACCAAG |
| | | | | ACCTACACCTGCAACGTGGACCACAAGCCAAGCAACACCAAGGTGGACAAG |
| | | | | CGCGTGGAGAGCAAGTACGGCCCACCATGCCCACCATGCCCAGCCCCAGAG |
| | | | | GCCGCCGGCGGCCCAAGCGTGTTCCTGTTCCCACCAAAGCCAAAGGACACC |
| | | | | CTGATGATCAGCCGCACCCCAGAGGTGACCTGCGTGGTGGTGGACGTGAGC |
| | | | | CAGGAGGACCCAGAGGTGCAGTTCAACTGGTACGTGGACGGCGTGGAGGTG |
| | | | | CACAACGCCAAGACCAAGCCACGCGAGGAGCAGTTCAACAGCACCTACCGC |
| | | | | GTGGTGAGCGTGCTGACCGTGCTGCACCAGGACTGGCTGAACGGCAAGGAG |
| | | | | TACAAGTGCAAGGTGAGCAACAAGGGCCTGCCAAGCAGCATCGAGAAGACC |
| | | | | ATCAGCAAGGCCAAGGGCCAGCCACGCGAGCCACAGGTGTACACCCTGCCA |
| | | | | CCAAGCCAGGAGGAGATGACCAAGAACCAGGTGAGCCTGAGCTGCGCCGTG |
| | | | | AAGGGCTTCTACCCAAGCGACATCGCCGTGGAGTGGGAGAGCAACGGCCAG |
| | | | | CCAGAGAACAACTACAAGACCACCCCACCAGTGCTGGACAGCGACGGCAGC |

| SEQ ID NO: | Type | Species | Description | Sequence |
|---|---|---|---|---|
| | | | | TTCTTCCTGGTGAGCCGCCTGACCGTGGACAAGAGCCGCTGGCAGGAGGGC AACGTGTTCAGCTGCAGCGTGATGCACGAGGCCCTGCACAACCGCTTCACC CAGAAGAGCCTGAGCCTGAGCCTGGGCAAGTGATAG |
| 30 | PRT | artificial | I3RB217 half antibody | MAWVWTLLFLMAAAQSIQAEIVLTQSPGTLSLSPGERATLSCRASQSVSSS YLAWYQQKPGQAPRLLIYGASSRATGIPDRFSGSGSGTDFTLTISRLEPED FAVYYCQQDYGFPWTFGQGTKVEIKRTVAAPSVFIFPPSDEQLKSGTASVV CLLNNFYPREAKVQWKVDNALQSGNSQESVTEQDSKDSTYSLSSTLTLSKA DYEKHKVYACEVTHQGLSSPVTKSFNRGECGGSEGKSSGSGSESKSTEGKS SGSGSESKSTGGSEVQLVQSGAEVKKPGESLKISCKGSGYSFTSYWISWVR QMPGKGLEWMGIIDPSDSDTRYSPSFQGQVTISADKSISTAYLQWSSLKAS DTAMYYCARGDGSTDLDYWGQGTLVTVSSASTKGPSVFPLAPCSRSTSEST AALGCLVKDYFPEPVTVSWNSGALTSGVHTFPAVLQSSGLYSLSSVVTVPS SSLGTKTYTCNVDHKPSNTKVDKRVESKYGPPCPPCPAPEAAGGPSVFLFP PKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREP QVYTLPPSQEEMTKNQVSLWCLVKGFYPSDIAVEWESNGQPENNYKTTPPV LDSDGSFFLYSRLTVDKSRWQEGNVFSCSVMHEALHNHYTQKSLSLSLGK |
| 31 | DNA | artificial | I3RB217 half antibody | ATGGCCTGGGTGTGGACCCTGCTGTTCCTGATGGCCGCCGCCCAGAGCATC CAGGCCGAGATCGTGCTGACCCAGAGCCCAGGCACCCTGAGCCTGAGCCCA GGCGAGCGCGCCACCCTGAGCTGCCGCGCCAGCCAGAGCGTGAGCAGCAGC TACCTGGCCTGGTACCAGCAGAAGCCAGGCCAGGCCCCACGCCTGCTGATC TACGGCGCCAGCAGCCGCGCCACCGGCATCCCAGACCGCTTCAGCGGCAGC GGCAGCGGCACCGACTTCACCCTGACCATCAGCCGCCTGGAGCCAGAGGAC TTCGCCGTGTACTACTGCCAGCAGGACTACGGCTTCCCATGGACCTTCGGC CAGGGCACCAAGGTGGAGATCAAGCGCACCGTGGCCGCCCCAAGCGTGTTC ATCTTCCCACCAAGCGACGAGCAGCTGAAGAGCGGCACCGCCAGCGTGGTG TGCCTGCTGAACAACTTCTACCCACGCGAGGCCAAGGTGCAGTGGAAGGTG GACAACGCCCTGCAGAGCGGCAACAGCCAGGAGAGCGTGACCGAGCAGGAC AGCAAGGACAGCACCTACAGCCTGAGCAGCACCCTGACCCTGAGCAAGGCC GACTACGAGAAGCACAAGGTGTACGCCTGCGAGGTGACCCACCAGGGCCTG AGCAGCCCAGTGACCAAGAGCTTCAACCGCGGCGAGTGCggcggcagcgag ggcaagagcagcggcagcggcagcgagagcaagagcaccgagggcaagagc agcggcagcggcagcgagagcaagagcaccggcggcagcGAGGTGCAGCTG GTGCAGAGCGGCGCCGAGGTGAAGAAGCCAGGCGAGAGCCTGAAGATCAGC TGCAAGGGCAGCGGCTACAGCTTCACCAGCTACTGGATCAGCTGGGTGCGC CAGATGCCAGGCAAGGGCCTGGAGTGGATGGGCATCATCGACCCAAGCGAC AGCGACACCCGCTACAGCCCAAGCTTCCAGGGCCAGGTGACCATCAGCGCC GACAAGAGCATCAGCACCGCCTACCTGCAGTGGAGCAGCCTGAAGGCCAGC GACACCGCCATGTACTACTGCGCCCGCGGCGACGGCAGCACCGACCTGGAC TACTGGGGCCAGGGCACCCTGGTGACCGTGAGCAGCGCCAGCACCAAGGGC CCAAGCGTGTTCCCACTGGCCCCATGCAGCCGCAGCACCAGCGAGAGCACC GCCGCCCTGGGCTGCCTGGTGAAGGACTACTTCCCAGAGCCAGTGACCGTG AGCTGGAACAGCGGCGCCCTGACCAGCGGCGTGCACACCTTCCCAGCCGTG CTGCAGAGCAGCGGCCTGTACAGCCTGAGCAGCGTGGTGACCGTGCCAAGC AGCAGCCTGGGCACCAAGACCTACACCTGCAACGTGGACCACAAGCCAAGC AACACCAAGGTGGACAAGCGCGTGGAGAGCAAGTACGGCCCACCATGCCCA CCATGCCCAGCCCCAGAGGCCGCCGGCGGCCCAAGCGTGTTCCTGTTCCCA CCAAAGCCAAAGGACACCCTGATGATCAGCCGCACCCCAGAGGTGACCTGC GTGGTGGTGGACGTGAGCCAGGAGGACCCAGAGGTGCAGTTCAACTGGTAC GTGGACGGCGTGGAGGTGCACAACGCCAAGACCAAGCCACGCGAGGAGCAG TTCAACAGCACCTACCGCGTGGTGAGCGTGCTGACCGTGCTGCACCAGGAC TGGCTGAACGGCAAGGAGTACAAGTGCAAGGTGAGCAACAAGGGCCTGCCA AGCAGCATCGAGAAGACCATCAGCAAGGCCAAGGGCCAGCCACGCGAGCCA CAGGTGTACACCCTGCCACCAAGCCAGGAGGAGATGACCAAGAACCAGGTG AGCCTGTGGTGCCTGGTGAAGGGCTTCTACCCAAGCGACATCGCCGTGGAG TGGGAGAGCAACGGCCAGCCAGAGAACAACTACAAGACCACCCCACCAGTG CTGGACAGCGACGGCAGCTTCTTCCTGTACAGCCGCCTGACCGTGGACAAG AGCCGCTGGCAGGAGGGCAACGTGTTCAGCTGCAGCGTGATGCACGAGGCC CTGCACAACCACTACACCCAGAAGAGCCTGAGCCTGAGCCTGGGCAAG |
| 32 | PRT | artificial | B23B49 half antibody | MAWVWTLLFLMAAAQSIQAEIVLTQSPGTLSLSPGERATLSCRASQSVSSS YLAWYQQKPGQAPRLLIYGASSRATGIPDRFSGSGSGTDFTLTISRLEPED FAVYYCQQDYGFPWTFGQGTKVEIKRTVAAPSVFIFPPSDEQLKSGTASVV CLLNNFYPREAKVQWKVDNALQSGNSQESVTEQDSKDSTYSLSSTLTLSKA DYEKHKVYACEVTHQGLSSPVTKSFNRGECGGSEGKSSGSGSESKSTEGKS SGSGSESKSTGGSEVQLVQSGAEVKKPGESLKISCKGSGYSFTSYWISWVR QMPGKGLEWMGIIDPSDSDTRYSPSFQGQVTISADKSISTAYLQWSSLKAS DTAMYYCARGDGSTDLDYWGQGTLVTVSSASTKGPSVFPLAPCSRSTSEST AALGCLVKDYFPEPVTVSWNSGALTSGVHTFPAVLQSSGLYSLSSVVTVPS SSLGTKTYTCNVDHKPSNTKVDKRVESKYGPPCPPCPAPEAAGGPSVFLFP PKPKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPREP QVYTLPPSQEEMTKNQVSLWCLVKGFYPSDIAVEWESNGQPENNYKTTPPV LDSDGSFFLYSRLTVDKSRWQEGNVFSCSVMHEALHNHYTQKSLSLSLGK |

| SEQ ID NO: | Type | Species | Description | Sequence |
|---|---|---|---|---|
| 33 | DNA | artificial | B23B49 half antibody | ATGGCCTGGGTGTGGACCCTGCTGTTCCTGATGGCCGCCGCCCAGAGCATC<br>CAGGCCGACATCGTGATGACCCAGAGCCCAGACAGCCTGGCCGTGAGCCTG<br>GGCGAGCGCGCCACCATCAACTGCCGCGCCAGCCAGAGCGTGGACTACAAC<br>GGCATCAGCTACATGCACTGGTACCAGCAGAAGCCAGGCCAGCCACCAAAG<br>CTGCTGATCTACGCCGCCAGCAACCTAGAGAGCGGCGTGCCAGACCGCTTC<br>AGCGGCAGCGGCAGCGGCACCGACTTCACCCTGACCATCAGCAGCCTGCAG<br>GCCGAGGACGTGGCCGTGTACTACTGCCAGCAGATCATCGAGGACCCATGG<br>ACCTTCGGCCAGGGCACCAAGGTGGAGATCAAGCGCACCGTGGCCGCCCCA<br>AGCGTGTTCATCTTCCCACCAAGCGACGAGCAGCTGAAGAGCGGCACCGCC<br>AGCGTGGTGTGCCTGCTGAACAACTTCTACCCACGCGAGGCCAAGGTGCAG<br>TGGAAGGTGGACAACGCCCTGCAGAGCGGCAACAGCCAGGAGAGCGTGACC<br>GAGCAGGACAGCAAGGACAGCACCTACAGCCTGAGCAGCACCCTGACCCTG<br>AGCAAGGCCGACTACGAGAAGCACAAGGTGTACGCCTGCGAGGTGACCCAC<br>CAGGGCCTGAGCAGCCCAGTGACCAAGAGCTTCAACCGCGGCGAGTGCGGC<br>GGCAGCGAGGGCAAGAGCAGCGGCAGCGGCAGCGAGAGCAAGAGCACCGAG<br>GGCAAGAGCAGCGGCAGCGGCAGCGAGAGCAAGAGCACCGGCGGCAGCCAG<br>ATCACCCTGAAGGAGAGCGGCCCAACCCTGGTGAAGCCAACCCAGACCCTG<br>ACCCTGACCTGCACCTTCAGCGGCTTCAGCCTGAGCACCAGCGGCATGGGC<br>GTGAGCTGGATCCGCCAGCCACCAGGCAAGGCCCTGGAGTGGCTGGCCCAC<br>ATCTACTGGGACGACGACAAGCGCTACAACCCAAGCCTGAAGAGCCGCCTG<br>ACCATCACCAAGGACACCAGCAAGAACCAGGTGGTGCTGACCATGACCAAC<br>ATGGACCCAGTGGACACCGCCACCTACTACTGCGCCCGCCTGTACGGCTTC<br>ACCTACGGCTTCGCCTACTGGGGCCAGGGCACCCTGGTGACCGTGAGCAGC<br>GCCAGCACCAAGGGCCCAAGCGTGTTCCCACTGGCCCCATGCAGCCGCAGC<br>ACCAGCGAGAGCACCGCCGCCCTGGGCTGCCTGGTGAAGGACTACTTCCCA<br>GAGCCAGTGACCGTGAGCTGGAACAGCGGCGCCCTGACCAGCGGCGTGCAC<br>ACCTTCCCAGCCGTGCTGCAGAGCAGCGGCCTGTACAGCCTGAGCAGCGTG<br>GTGACCGTGCCAAGCAGCAGCCTGGGCACCAAGACCTACACCTGCAACGTG<br>GACCACAAGCCAAGCAACACCAAGGTGGACAAGCGCGTGGAGAGCAAGTAC<br>GGCCCACCATGCCCACCATGCCCAGCCCCAGAGGCCGCCGGCGGCCCAAGC<br>GTGTTCCTGTTCCCACCAAAGCCAAAGGACACCCTGATGATCAGCCGCACC<br>CCAGAGGTGACCTGCGTGGTGGTGGACGTGAGCCAGGAGGACCCAGAGGTG<br>CAGTTCAACTGGTACGTGGACGGCGTGGAGGTGCACAACGCCAAGACCAAG<br>CCACGCGAGGAGCAGTTCAACAGCACCTACCGCGTGGTGAGCGTGCTGACC<br>GTGCTGCACCAGGACTGGCTGAACGGCAAGGAGTACAAGTGCAAGGTGAGC<br>AACAAGGGCCTGCCAAGCAGCATCGAGAAGACCATCAGCAAGGCCAAGGGC<br>CAGCCACGCGAGCCACAGGTGTACACCCTGCCACCAAGCCAGGAGGAGATG<br>ACCAAGAACCAGGTGAGCCTGTGGTGCCTGGTGAAGGGCTTCTACCCAAGC<br>GACATCGCCGTGGAGTGGGAGAGCAACGGCCAGCCAGAGAACAACTACAAG<br>ACCACCCCACCAGTGCTGGACAGCGACGGCAGCTTCTTCCTGTACAGCCGC<br>CTGACCGTGGACAAGAGCCGCTGGCAGGAGGGCAACGTGTTCAGCTGCAGC<br>GTGATGCACGAGGCCCTGCACAACCACTACACCCAGAAGAGCCTGAGCCTG<br>AGCCTGGGCAAG |
| 34 | PRT | Artificial | HCDR1 | SYWIS |
| 35 | PRT | Artificial | HCDR2 | IIDPSDSDTRYSPSFQG |
| 36 | PRT | Artificial | HCDR3 | GDGSTDLDY |
| 37 | PRT | Artificial | LCDR1 | RASQSVSSSYL |
| 38 | PRT | Artificial | LCDR2 | GASSRAT |
| 39 | PRT | Artificial | LCDR3 | QQDYGFPWT |
| 40 | PRT | Artificial | HC | EVQLVQSGAEVKKPGESLKISCKGSGYSFTSYWISWVRQMPGKGLEWMGII<br>DPSDSDTRYSPSFQGQVTISADKSISTAYLQWSSLKASDTAMYYCARGDGS<br>TDLDYWGQGTLVTVSS |
| 41 | PRT | Artificial | LC | EIVLTQSPGTLSLSPGERATLSCRASQSVSSSYLAWYQQKPGQAPRLLIYG<br>ASSRATGIPDRFSGSGSGTDFTLTISRLEPEDFAVYYCQQDYGFPWTFGQG<br>TKVEIK |
| 42 | PRT | Artificial | IGHJ1*01 HC | WGQGTLVTVSS |
| 43 | PRT | Artificial | IGKJ2*01 LC | FGQGTKLEIK |
| 44 | PRT | Artificial | Val0.2_Fc | MAWVWTLLFLMAAAQSIQAQLLEQSPQFLSIQEGENLTVYCNSSSVFSSLQ<br>WYRQEPGEGPVLLVTVVTGGEVKKLKRLTFQFGDARKDSSLHITAAQPGDT<br>GLYLCAGAGSQGNLIFGKGTKLSVKPNIQNPDPAVYQLRDSKSSDKSVCLF<br>TDFDSQTNVSQSKDSDVYITDKTVLDMRSMDFKSNSAVAWSNKSDFACANA<br>FNNSIIPEDTFFPSepkscdkthtcppcpapeLLggpsvflfppkpkdtlm |

| SEQ ID NO: | Type | Species | Description | Sequence |
|---|---|---|---|---|
| | | | | isrtpevtcvvvDvshedpevkfnwyvdgvevhnaktkpreeqynstyrvv syltvlhqdwingkeykckvsnkalpapiektiskakgqprepqvyVYpps reemtknqvsltclvkgfypsdiavewesngqpennykttppvldsdgsfA lVskltvdksnvqqgnvfscsvmhealhnhytqkslslspg |

The invention claimed is:

1. An isolated Vβ17 bispecific antibody or antigen-binding fragment thereof, the isolated Vβ17 bispecific antibody or antigen-binding fragment thereof comprising:
   a. a first heavy chain (HC1);
   b. a second heavy chain (HC2);
   c. a first light chain (LC1); and
   d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for the second antigen.

2. The Vβ17 bispecific antibody or antigen-binding fragment thereof of claim 1, wherein
   (A) the binding site for the first antigen binds to Vβ17 on a CD8+ or CD4+ T cell;
   (B) the binding site for the second antigen binds to a tumor antigen present on the surface of a cancer cell; and/or
   (C) the bispecific antibody or antigen-binding fragment thereof is a IgG isotype.

3. The Vβ17 bispecific antibody or antigen-binding fragment of claim 1, wherein HC1 and LC1 are humanized.

4. The Vβ17 bispecific antibody or antigen-binding fragment thereof of claim 1, wherein HC2 and LC2 bind to CD123.

5. An isolated nucleic acid encoding (A) the HC1 and the LC1 of the Vβ17 bispecific antibody or antigen-binding fragment thereof of claim 1; and (B) the HC2 and the LC2 of the Vβ17 bispecific antibody or antigen-binding fragment thereof of claim 1.

6. A vector comprising the isolated nucleic acid of claim 5.

7. A host cell comprising the vector of claim 6.

8. An isolated anti-Vβ17/anti-CD123 bispecific antibody or antigen-binding fragment thereof comprising:
 a. a first heavy chain (HC1);
 b. a second heavy chain (HC2)
 c. a first light chain (LC1); and
 d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of SEQ ID NO:1, SEQ ID NO:2, and SEQ ID NO:3, respectively, and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen that specifically binds Vβ17, and wherein HC2 comprises a heavy chain complementarity determining region 1 (HCDR1), HCDR2, and HCDR3 comprising the amino acid sequences of SEQ ID NO:34, SEQ ID NO:35, and SEQ ID NO:36, respectively, and LC2 comprises a light chain complementarity determining region 1 (LCDR1), LCDR2, and LCDR3 comprising the amino acid sequences of SEQ ID NO:37, SEQ ID NO:38, and SEQ ID NO:39, respectively, to form a binding site for a second antigen that specifically binds CD123.

9. The isolated anti-Vβ17/anti-CD123 bispecific antibody or antigen-binding fragment thereof of claim 8, wherein HC1 comprises the amino acid sequence of SEQ ID NO:13 and LC1 comprises the amino acid sequence of SEQ ID NO:14, and wherein HC2 comprises the amino acid sequence of SEQ ID NO:15 and LC2 comprises the amino acid sequence of SEQ ID NO:16.

10. The isolated anti-Vβ17/anti-CD123 bispecific antibody or antigen-binding fragment thereof of claim 8, wherein
 (A) the Vβ17 is on the surface of a CD8+ or CD4+ T cell;
 (B) the CD123 is on the surface of a cancer cell or a CD34+ stem cell; and/or
 (C) the bispecific antibody or antigen-binding fragment thereof induces CD8+ or CD4+ T-cell dependent cytotoxicity of a cancer cell in vitro with an $EC_{50}$ of less than about 0.2 pM.

11. An isolated nucleic acid encoding (A) the HC1 and LC1 of the anti-Vβ17/anti-CD123 bispecific antibody or antigen-binding fragment thereof of claim 8, and (B) the HC2 and LC2 of the anti-Vβ17/anti-CD123 bispecific antibody or antigen-binding fragment thereof of claim 8.

12. A vector comprising the isolated nucleic acid of claim 11.

13. A host cell comprising the vector of claim 12.

14. A buffered composition comprising the isolated anti-Vβ17/anti-CD123 bispecific antibody or antigen-binding fragment thereof of claim 8.

15. A method
 (A) of directing a Vβ17-expressing CD8+ or CD4+ T cell to a cancer cell, the method comprising contacting a Vβ17-expressing CD8+ or CD4+ T cell with the anti-Vβ17/anti-CD123 bispecific antibody or antigen-binding fragment thereof of claim 8, wherein contacting the Vβ17-expressing CD8+ or CD4+ T cell with the anti-Vβ17/anti-CD123 bispecific antibody or antigen-binding fragment thereof directs the Vβ17-expressing CD8+ or CD4+ T cell to a cancer cell; or
 (B) for inhibiting growth or proliferation of cancer cells, the method comprising contacting the cancer cells with the anti-Vβ17/anti-CD123 bispecific antibody or antigen-binding fragment thereof of claim 13, wherein contacting the cancer cells with the anti-Vβ17/anti-CD123 bispecific antibody or antigen-binding fragment thereof inhibits the growth or proliferation of the cancer cells.

16. The method of claim 15, wherein the cancer cell is a CD123-expressing cancer cell.

17. A kit comprising a Vβ17 bispecific antibody or antigen-binding fragment thereof of claim 1 and packaging for the same.

18. A kit comprising an anti-Vβ17/anti-CD123 bispecific antibody or antigen-binding fragment thereof of claim 8 and packaging for the same.

19. A method of producing a Vβ17 bispecific antibody or antigen-binding fragment thereof comprising culturing the host cell of claim 7 to produce the Vβ17 bispecific antibody or antigen-binding fragment thereof, and recovering the Vβ17 bispecific antibody or antigen-binding fragment thereof from the cell or culture.

20. A method of producing an anti-Vβ17/anti-CD123 bispecific antibody or antigen-binding fragment thereof comprising culturing the host cell of claim 13 to produce the anti-Vβ17/anti-CD123 bispecific antibody or antigen-binding fragment thereof, and recovering the anti-Vβ17/anti-CD123 bispecific antibody or antigen-binding fragment thereof from the cell or culture.

21. An isolated humanized Vβ17 monoclonal antibody or antigen-binding fragment thereof, the humanized Vβ17 monoclonal antibody or antigen-binding fragment thereof comprising the amino acid sequence of SEQ ID NO:28.

22. An isolated nucleic acid encoding the isolated humanized Vβ17 monoclonal antibody or antigen-binding fragment thereof of claim 21.

23. A vector comprising the isolated nucleic acid of claim 22.

24. A host cell comprising the vector of claim 23.

25. The Vβ17 bispecific antibody or antigen-binding fragment thereof of claim 2, wherein the bispecific antibody or antigen-binding fragment thereof is a IgG4 isotype.

* * * * *

SEQUENCE LISTING

<160> NUMBER OF SEQ ID NOS: 44

<210> SEQ ID NO 1
<211> LENGTH: 11
<212> TYPE: PRT
<213> ORGANISM: Artificial Sequence
<220> FEATURE:
<223> OTHER INFORMATION: B17B01 HCDR1

<400> SEQUENCE: 1

Gly Tyr Ser Ile Thr Ser Gly Tyr Phe Trp Asn
1               5                   10

<210> SEQ ID NO 2
<211> LENGTH: 9
<212> TYPE: PRT
<213> ORGANISM: Artificial Sequence
<220> FEATURE:
<223> OTHER INFORMATION: B17B01 HCDR2

<400> SEQUENCE: 2

Tyr Ile Ser Tyr Asp Gly Ser Asn Asn
1               5

<210> SEQ ID NO 3
<211> LENGTH: 11
<212> TYPE: PRT
<213> ORGANISM: Artificial Sequence
<220> FEATURE:
<223> OTHER INFORMATION: B17B01 HCDR3

<400> SEQUENCE: 3

Pro Ser Pro Gly Thr Gly Tyr Ala Val Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: B17B01 LCDR1

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: B17B01 LCDR2

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: B17B01 LCDR3

<400> SEQUENCE: 6

Ser Gln Ser Thr His Val Pro Phe Thr
1               5

<210> SEQ ID NO 7
<211> LENGTH: 444
<212> TYPE: PRT
<213> ORGANISM: Artificial Sequence
<220> FEATURE:
<223> OTHER INFORMATION: B17B01 Heavy Chain

<400> SEQUENCE: 7

Asn Val Gln Leu Gln Glu Ser Gly Pro Gly Leu Val Lys Pro Ser Gln
1               5                   10                  15

Ser Leu Ser Leu Thr Cys Ser Val Ala Gly Tyr Ser Ile Thr Ser Gly
                20                  25                  30

Tyr Phe Trp Asn Trp Ile Arg Gln Phe Pro Gly Asn Lys Leu Glu Trp
            35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ser Pro Ser Pro Gly Thr Gly Tyr Ala Val Asp Tyr Trp Gly Gln
            100                 105                 110

Gly Thr Ser Val Thr Val Ser Ser Ala Lys Thr Thr Pro Pro Ser Val
    115                 120                 125

Tyr Pro Leu Ala Pro Gly Ser Ala Ala Gln Thr Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro

```
                290                 295                 300
Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Tyr Gly Arg Pro Lys Ala Pro Gln Val Tyr Thr Ile Pro Pro Pro Lys
                340                 345                 350

Glu Gln Met Ala Lys Asp Lys Val Ser Leu Thr Cys Met Ile Thr Asn
                355                 360                 365

Phe Phe Pro Glu Asp Ile Thr Val Glu Trp Gln Trp Asn Gly Gln Pro
                370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440

<210> SEQ ID NO 8
<211> LENGTH: 219
<212> TYPE: PRT
<213> ORGANISM: Artificial Sequence
<220> FEATURE:
<223> OTHER INFORMATION: B17B01 Light Chain

<400> SEQUENCE: 8

Asn Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
                35                  40                  45

Pro Lys Phe Leu Ile Tyr Lys Val Ser Asn Arg Phe Ser Gly Val Pro
                50                  55                  60

Asp Arg Phe Ser Gly Gly Gly Ser Gly Thr Glu Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
                100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
                130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
```

-continued

<210> SEQ ID NO 9
<211> LENGTH: 447
<212> TYPE: PRT
<213> ORGANISM: Artificial Sequence
<220> FEATURE:
<223> OTHER INFORMATION: B17B1 Heavy Chain

<400> SEQUENCE: 9

```
Asn Val Gln Leu Gln Glu Ser Gly Pro Gly Leu Val Lys Pro Ser Gln
1               5                   10                  15

Ser Leu Ser Leu Thr Cys Ser Val Ala Gly Tyr Ser Ile Thr Ser Gly
            20                  25                  30

Tyr Phe Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ser Pro Ser Pro Gly Thr Gly Tyr Ala Val Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
```

```
                355                 360                 365
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
                435                 440                 445

<210> SEQ ID NO 10
<211> LENGTH: 219
<212> TYPE: PRT
<213> ORGANISM: Artificial Sequence
<220> FEATURE:
<223> OTHER INFORMATION: B17B1 Light Chain

<400> SEQUENCE: 10

Asn Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Gly Ser Gly Thr Glu Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 11
<211> LENGTH: 447
<212> TYPE: PRT
<213> ORGANISM: Artificial Sequence
<220> FEATURE:
<223> OTHER INFORMATION: B17B2 Heavy Chain

<400> SEQUENCE: 11
```

-continued

```
Asp Val Gln Leu Lys Glu Ser Gly Pro Gly Leu Val Lys Pro Ser Gln
 1               5                  10                  15
Ser Leu Ser Val Thr Cys Ser Val Thr Gly Tyr Ser Ile Thr Ser Gly
            20                  25                  30
Tyr Tyr Trp Asn Trp Tyr Arg Gln Phe Pro Gly Asn Lys Leu Glu Trp
        35                  40                  45
Met Gly Tyr Ile Ser Tyr Asp Gly Ser Asn Asn Tyr Asn Pro Ser Leu
    50                  55                  60
Lys Asn Arg Ile Ser Ile Thr Arg Asp Thr Ser Lys Asn Gln Ile Leu
 65                  70                  75                  80
Leu Lys Leu Thr Tyr Val Thr Thr Glu Asp Thr Ala Thr Tyr Tyr Cys
                85                  90                  95
Thr Arg Pro Ser Pro Gly Thr Gly Tyr Ala Val Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Leu Leu Tyr Ser Lys Leu Thr Val Asp Lys Ser Arg
                405                 410                 415
Trp Gln Glu Gly Asn Val Phe Ser Cys Ser Val Met His Glu Ala Leu
```

His Asn His Tyr Thr Gln Lys Ser Leu Ser Leu Ser Leu Gly Lys
            420                 425                 430

435                 440                 445

<210> SEQ ID NO 12
<211> LENGTH: 219
<212> TYPE: PRT
<213> ORGANISM: Artificial Sequence
<220> FEATURE:
<223> OTHER INFORMATION: B17B2 Light Chain

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Gly Asn Thr Tyr Leu His Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr His Val Pro Phe Thr Phe Gly Gln Gly Thr Lys Val Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 13
<211> LENGTH: 447
<212> TYPE: PRT
<213> ORGANISM: Artificial Sequence
<220> FEATURE:
<223> OTHER INFORMATION: B17B21 Heavy Chain

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Ile Ser Tyr Asp Gly Ser Asn Asn Tyr Asn Pro Ser Leu
    50                  55                  60

```
Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Ser Pro Ser Pro Gly Thr Gly Tyr Ala Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Phe Thr Gln Lys Ser Leu Ser Leu Ser Leu Gly Lys
        435                 440                 445
```

<210> SEQ ID NO 14
<211> LENGTH: 219
<212> TYPE: PRT
<213> ORGANISM: Artificial Sequence
<220> FEATURE:
<223> OTHER INFORMATION: B17B21 Light Chain

<400> SEQUENCE: 14

| | | | | | | | | | | | | | | |
|---|---|---|---|---|---|---|---|---|---|---|---|---|---|---|
|Asp|Ile|Gln|Met|Thr|Gln|Ser|Pro|Ser|Ser|Leu|Ser|Ala|Ser|Val|Gly
1| | | |5| | | | |10| | | | |15|

Asp Arg Val Thr Ile Thr Cys Arg Ser Ser Gln Ser Leu Val His Ser
          20                 25                 30

Asn Gly Asn Thr Tyr Leu His Trp Tyr Gln Gln Lys Pro Gly Lys Ala
          35                 40                 45

Pro Lys Phe Leu Ile Tyr Lys Val Ser Asn Arg Phe Ser Gly Val Pro
 50                 55                 60

Ser Arg Phe Ser Gly Ser Gly Ser Gly Thr Asp Phe Thr Leu Thr Ile
65                 70                 75                 80

Ser Ser Leu Gln Pro Glu Asp Phe Ala Thr Tyr Tyr Cys Ser Gln Ser
               85                 90                 95

Thr His Val Pro Phe Thr Phe Gly Gln Gly Thr Lys Leu Glu Ile Lys
          100                 105               110

Arg Thr Val Ala Ala Pro Ser Val Phe Ile Phe Pro Pro Ser Asp Glu
          115                 120               125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
          165                 170               175

Thr Tyr Ser Leu Ser Ser Thr Leu Thr Leu Ser Lys Ala Asp Tyr Glu
          180                 185               190

Lys His Lys Val Tyr Ala Cys Glu Val Thr His Gln Gly Leu Ser Ser
          195                 200               205

Pro Val Thr Lys Ser Phe Asn Arg Gly Glu Cys
          210                 215

<210> SEQ ID NO 15
<211> LENGTH: 445
<212> TYPE: PRT
<213> ORGANISM: Artificial Sequence
<220> FEATURE:
<223> OTHER INFORMATION: I3RB217 Heavy Chain

<400> SEQUENCE: 15

Glu Val Gln Leu Val Gln Ser Gly Ala Glu Val Lys Lys Pro Gly Glu
1                 5                 10                 15

Ser Leu Lys Ile Ser Cys Lys Gly Ser Gly Tyr Ser Phe Thr Ser Tyr
          20                 25                 30

Trp Ile Ser Trp Val Arg Gln Met Pro Gly Lys Gly Leu Glu Trp Met
          35                 40                 45

Gly Ile Ile Asp Pro Ser Asp Ser Asp Thr Arg Tyr Ser Pro Ser Phe
 50                 55                 60

Gln Gly Gln Val Thr Ile Ser Ala Asp Lys Ser Ile Ser Thr Ala Tyr
65                 70                 75                 80

Leu Gln Trp Ser Ser Leu Lys Ala Ser Asp Thr Ala Met Tyr Tyr Cys
               85                 90                 95

Ala Arg Gly Asp Gly Ser Thr Asp Leu Asp Tyr Trp Gly Gln Gly Thr
          100                 105               110

Leu Val Thr Val Ser Ser Ala Ser Thr Lys Gly Pro Ser Val Phe Pro
          115                 120               125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 16
<211> LENGTH: 215
<212> TYPE: PRT
<213> ORGANISM: Artificial Sequence
<220> FEATURE:
<223> OTHER INFORMATION: I3RB217 Light Chain

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Tyr Gly Phe Pro
                 85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
210                 215

<210> SEQ ID NO 17
<211> LENGTH: 447
<212> TYPE: PRT
<213> ORGANISM: Artificial Sequence
<220> FEATURE:
<223> OTHER INFORMATION: Null Heavy Chain

<400> SEQUENCE: 17

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Met Gly Val Ser Trp Ile Arg Gln Pro Pro Gly Lys Ala Leu Glu
                 35                  40                  45

Trp Leu Ala His Ile Tyr Trp Asp Asp Asp Lys Arg Tyr Asn Pro Ser
     50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Leu Tyr Gly Phe Thr Tyr Gly Phe Ala Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190
```

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 18
<211> LENGTH: 218
<212> TYPE: PRT
<213> ORGANISM: Artificial Sequence
<220> FEATURE:
<223> OTHER INFORMATION: Null Light Chain

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys Arg
            100                 105                 110

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 19
<211> LENGTH: 119
<212> TYPE: PRT
<213> ORGANISM: Artificial Sequence
<220> FEATURE:
<223> OTHER INFORMATION: B17H3

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Phe Trp Asn Trp Val Arg Gln Ala Pro Gly Lys Gly Leu Glu Trp
        35                  40                  45

Val Ser Tyr Ile Ser Tyr Asp Gly Ser Asn Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Pro Gly Thr Gly Tyr Ala Val Asp Tyr Trp Gly Gln
            100                 105                 110

Gly Thr Leu Val Thr Val Ser
        115

<210> SEQ ID NO 20
<211> LENGTH: 120
<212> TYPE: PRT
<213> ORGANISM: Artificial Sequence
<220> FEATURE:
<223> OTHER INFORMATION: B17H4

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Phe Trp Asn Trp Val Arg Gln Ala Pro Gly Lys Gly Leu Glu Trp
        35                  40                  45

Val Ser Tyr Ile Ser Tyr Asp Gly Ser Asn Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Ser Pro Ser Pro Gly Thr Gly Tyr Ala Val Asp Tyr Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: B17H5

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Ile Ser Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Pro Ser Pro Gly Thr Gly Tyr Ala Val Asp Tyr Trp Gly Gln
            100                 105                 110

Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: B17L3

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Phe Thr Phe Gly Gln Gly Thr Lys Leu Glu Ile Lys
            100                 105                 110

<210> SEQ ID NO 23
<211> LENGTH: 112
<212> TYPE: PRT

```
<213> ORGANISM: Artificial Sequence
<220> FEATURE:
<223> OTHER INFORMATION: B17L4

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Phe Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Tyr Cys Ser Gln Ser
                85                  90                  95

Thr His Val Pro Phe Thr Phe Gly Gln Gly Thr Lys Leu Glu Ile Lys
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: B17L5

<400> SEQUENCE: 24

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95

Thr His Val Pro Phe Thr Phe Gly Gln Gly Thr Lys Leu Glu Ile Lys
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: B17H1

<400> SEQUENCE: 25

Asn Val Gln Leu Gln Glu Ser Gly Pro Gly Leu Val Lys Pro Ser Gln
1               5                   10                  15

Ser Leu Ser Leu Thr Cys Ser Val Ala Gly Tyr Ser Ile Thr Ser Gly
            20                  25                  30

Tyr Phe Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60
```

```
Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Ser Pro Ser Pro Gly Thr Gly Tyr Ala Val Asp Tyr Trp Gly Gln
            100                 105                 110

Gly Thr Ser Val Thr Val Ser Ser
            115                 120

<210> SEQ ID NO 26
<211> LENGTH: 112
<212> TYPE: PRT
<213> ORGANISM: Artificial Sequence
<220> FEATURE:
<223> OTHER INFORMATION: B17L1

<400> SEQUENCE: 26

Asn Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Phe Leu Ile Tyr Lys Val Ser Asn Arg Phe Ser Gly Val Pro
 50                  55                  60

Asp Arg Phe Ser Gly Gly Gly Ser Gly Thr Glu Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

<210> SEQ ID NO 27
<211> LENGTH: 493
<212> TYPE: PRT
<213> ORGANISM: Artificial Sequence
<220> FEATURE:
<223> OTHER INFORMATION: TCR-Vbeta17_Fc fusion

<400> SEQUENCE: 27

Met Ala Trp Val Trp Thr Leu Leu Phe Leu Met Ala Ala Ala Gln Ser
 1               5                  10                  15

Ile Gln Ala Val Asp Gly Gly Ile Thr Gln Ser Pro Lys Tyr Leu Phe
             20                  25                  30

Arg Lys Glu Gly Gln Asn Val Thr Leu Ser Cys Glu Gln Asn Leu Asn
         35                  40                  45

His Asp Ala Met Tyr Trp Tyr Arg Gln Asp Pro Gly Gln Gly Leu Arg
 50                  55                  60

Leu Ile Tyr Tyr Ser Gln Ile Val Asn Asp Phe Gln Lys Gly Asp Ile
 65                  70                  75                  80

Ala Glu Gly Tyr Ser Val Ser Arg Glu Lys Lys Glu Ser Phe Pro Leu
                 85                  90                  95

Thr Val Thr Ser Ala Gln Lys Asn Pro Thr Ala Phe Tyr Leu Cys Ala
            100                 105                 110

Ser Ser Ser Arg Ser Ser Tyr Glu Gln Tyr Phe Gly Pro Gly Thr Arg
            115                 120                 125

Leu Thr Val Thr Glu Asp Leu Lys Asn Val Phe Pro Pro Glu Val Ala
```

```
            130                 135                 140
Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Ser Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Glu Pro Lys Ser Cys Asp Lys Thr His Thr
                260                 265                 270

Cys Pro Pro Cys Pro Ala Pro Glu Leu Leu Gly Gly Pro Ser Val Phe
            275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
                355                 360                 365

Lys Val Ser Asn Lys Ala Leu Pro Ala Pro Ile Glu Lys Thr Ile Ser
370                 375                 380

Lys Ala Lys Gly Gln Pro Arg Glu Pro Gln Val Tyr Val Leu Pro Pro
385                 390                 395                 400

Ser Arg Glu Glu Met Thr Lys Asn Gln Val Ser Leu Leu Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Leu Thr Trp Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly
                485                 490

<210> SEQ ID NO 28
<211> LENGTH: 719
<212> TYPE: PRT
<213> ORGANISM: Artificial Sequence
<220> FEATURE:
<223> OTHER INFORMATION: B17B21 half antibody

<400> SEQUENCE: 28

Met Ala Trp Val Trp Thr Leu Leu Phe Leu Met Ala Ala Ala Gln Ser
```

-continued

```
1               5               10              15
Ile Gln Ala Asp Ile Gln Met Thr Gln Ser Pro Ser Ser Leu Ser Ala
                20              25              30

Ser Val Gly Asp Arg Val Thr Ile Thr Cys Arg Ser Ser Gln Ser Leu
                35              40              45

Val His Ser Asn Gly Asn Thr Tyr Leu His Trp Tyr Gln Gln Lys Pro
50              55              60

Gly Lys Ala Pro Lys Phe Leu Ile Tyr Lys Val Ser Asn Arg Phe Ser
65              70              75              80

Gly Val Pro Ser Arg Phe Ser Gly Ser Gly Ser Gly Thr Asp Phe Thr
                85              90              95

Leu Thr Ile Ser Ser Leu Gln Pro Glu Asp Phe Ala Thr Tyr Tyr Cys
                100             105             110

Ser Gln Ser Thr His Val Pro Phe Thr Phe Gly Gln Gly Thr Lys Leu
                115             120             125

Glu Ile Lys Arg Thr Val Ala Ala Pro Ser Val Phe Ile Phe Pro Pro
                130             135             140

Ser Asp Glu Gln Leu Lys Ser Gly Thr Ala Ser Val Val Cys Leu Leu
145             150             155             160

Asn Asn Phe Tyr Pro Arg Glu Ala Lys Val Gln Trp Lys Val Asp Asn
                165             170             175

Ala Leu Gln Ser Gly Asn Ser Gln Glu Ser Val Thr Glu Gln Asp Ser
                180             185             190

Lys Asp Ser Thr Tyr Ser Leu Ser Ser Thr Leu Thr Leu Ser Lys Ala
                195             200             205

Asp Tyr Glu Lys His Lys Val Tyr Ala Cys Glu Val Thr His Gln Gly
                210             215             220

Leu Ser Ser Pro Val Thr Lys Ser Phe Asn Arg Gly Glu Cys Gly Gly
225             230             235             240

Ser Glu Gly Lys Ser Ser Gly Ser Gly Ser Glu Ser Lys Ser Thr Glu
                245             250             255

Gly Lys Ser Ser Gly Ser Gly Ser Glu Ser Lys Ser Thr Gly Gly Ser
                260             265             270

Gln Val Gln Leu Gln Glu Ser Gly Pro Gly Leu Val Lys Pro Ser Glu
                275             280             285

Thr Leu Ser Leu Thr Cys Thr Val Ser Gly Tyr Ser Ile Thr Ser Gly
                290             295             300

Tyr Phe Trp Asn Trp Ile Arg Gln Pro Pro Gly Lys Gly Leu Glu Trp
305             310             315             320

Ile Gly Tyr Ile Ser Tyr Asp Gly Ser Asn Asn Tyr Asn Pro Ser Leu
                325             330             335

Lys Ser Arg Val Thr Ile Ser Arg Asp Thr Ser Lys Asn Gln Phe Ser
                340             345             350

Leu Lys Leu Ser Ser Val Thr Ala Ala Asp Thr Ala Val Tyr Tyr Cys
                355             360             365

Ala Ser Pro Ser Pro Gly Thr Gly Tyr Ala Val Asp Tyr Trp Gly Gln
                370             375             380

Gly Thr Leu Val Thr Val Ser Ser Ala Ser Thr Lys Gly Pro Ser Val
385             390             395             400

Phe Pro Leu Ala Pro Cys Ser Arg Ser Thr Ser Glu Ser Thr Ala Ala
                405             410             415

Leu Gly Cys Leu Val Lys Asp Tyr Phe Pro Glu Pro Val Thr Val Ser
                420             425             430
```

```
Trp Asn Ser Gly Ala Leu Thr Ser Gly Val His Thr Phe Pro Ala Val
        435                 440                 445
Leu Gln Ser Ser Gly Leu Tyr Ser Leu Ser Ser Val Val Thr Val Pro
    450                 455                 460
Ser Ser Ser Leu Gly Thr Lys Thr Tyr Thr Cys Asn Val Asp His Lys
465                 470                 475                 480
Pro Ser Asn Thr Lys Val Asp Lys Arg Val Glu Ser Lys Tyr Gly Pro
                485                 490                 495
Pro Cys Pro Pro Cys Pro Ala Pro Glu Ala Ala Gly Gly Pro Ser Val
            500                 505                 510
Phe Leu Phe Pro Pro Lys Pro Lys Asp Thr Leu Met Ile Ser Arg Thr
        515                 520                 525
Pro Glu Val Thr Cys Val Val Val Asp Val Ser Gln Glu Asp Pro Glu
    530                 535                 540
Val Gln Phe Asn Trp Tyr Val Asp Gly Val Glu Val His Asn Ala Lys
545                 550                 555                 560
Thr Lys Pro Arg Glu Glu Gln Phe Asn Ser Thr Tyr Arg Val Val Ser
                565                 570                 575
Val Leu Thr Val Leu His Gln Asp Trp Leu Asn Gly Lys Glu Tyr Lys
            580                 585                 590
Cys Lys Val Ser Asn Lys Gly Leu Pro Ser Ser Ile Glu Lys Thr Ile
        595                 600                 605
Ser Lys Ala Lys Gly Gln Pro Arg Glu Pro Gln Val Tyr Thr Leu Pro
    610                 615                 620
Pro Ser Gln Glu Glu Met Thr Lys Asn Gln Val Ser Leu Ser Cys Ala
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
            660                 665                 670
Asp Gly Ser Phe Phe Leu Val Ser Arg Leu Thr Val Asp Lys Ser Arg
        675                 680                 685
Trp Gln Glu Gly Asn Val Phe Ser Cys Ser Val Met His Glu Ala Leu
    690                 695                 700
His Asn Arg Phe Thr Gln Lys Ser Leu Ser Leu Ser Leu Gly Lys
705                 710                 715

<210> SEQ ID NO 29
<211> LENGTH: 4320
<212> TYPE: DNA
<213> ORGANISM: Artificial Sequence
<220> FEATURE:
<223> OTHER INFORMATION: B17B21 half antibody

<400> SEQUENCE: 29
atggcctggg tgtggaccct gctgttcctg atggccgccg cccagagcat ccaggccgac      60
atccagatga cccagagccc aagcagcctg agcgccagcg tgggcgaccg cgtgaccatc     120
acctgccgca gcagccagag cctggtgcac agcaacggca cacctacct gcactggtac      180 cagcagaagc caggcaaggc cccaaagttc ctgatctaca aggtgagcaa ccgcttcagc     240
ggcgtgccaa gccgcttcag cggcagcggc agcggcaccg acttcaccct gaccatcagc     300
agcctgcagc cagaggactt cgccacctac tactgcagcc agagcaccca cgtgccattc     360
accttcggcc agggcaccaa gctggagatc aagcgcaccg tggccgcccc aagcgtgttc     420
```

-continued

```
atcttcccac caagcgacga gcagctgaag agcggcaccg ccagcgtggt gtgcctgctg    480
aacaacttct acccacgcga ggccaaggtg cagtggaagg tggacaacgc cctgcagagc    540
ggcaacagcc aggagagcgt gaccgagcag gacagcaagg acagcaccta cagcctgagc    600
agcaccctga ccctgagcaa ggccgactac gagaagcaca aggtgtacgc ctgcgaggtg    660
acccaccagg gcctgagcag cccagtgacc aagagcttca accgcggcga gtgcggcggc    720
agcgagggca agagcagcgg cagcggcagc gagagcaaga gcaccgaggg caagagcagc    780
ggcagcggca gcgagagcaa gagcaccggc ggcagccagg tgcagctgca ggagagcggc    840
ccaggcctgg tgaagccaag cgagaccctg agcctgacct gcaccgtgag cggctacagc    900
atcaccagcg gctacttctg gaactggatc cgccagccac aggcaagggg cctggagtgg    960
atcggctaca tcagctacga cggcagcaac aactacaacc caagcctgaa gagccgcgtg   1020
accatcagcc gcgacaccag caagaaccag ttcagcctga agctgagcag cgtgaccgcc   1080
gccgacaccg ccgtgtacta ctgcgccagc ccaagcccag gcaccggcta cgccgtggac   1140
tactggggcc agggcaccct ggtgaccgtg agcagcgcca gcaccaaggg cccaagcgtg   1200
ttcccactgg ccccatgcag ccgcagcacc agcgagagca ccgccgccct gggctgcctg   1260
gtgaaggact acttcccaga gccagtgacc gtgagctgga acagcggcgc cctgaccagc   1320
ggcgtgcaca ccttcccagc cgtgctgcag agcagcggcc tgtacagcct gagcagcgtg   1380
gtgaccgtgc caagcagcag cctgggcacc aagacctaca cctgcaacgt ggaccacaag   1440
ccaagcaaca ccaaggtgga caagcgcgtg gagagcaagt acggcccacc atgcccacca   1500
tgcccagccc cagaggccgc cggcggccca agcgtgttcc tgttcccacc aaagccaaag   1560
gacaccctga tgatcagccg caccccagag gtgacctgcg tggtggtgga cgtgagccag   1620
gaggacccag aggtgcagtt caactggtac gtggacggcg tggaggtgca caacgccaag   1680
accaagccac gcgaggagca gttcaacagc acctaccgcg tggtgagcgt gctgaccgtg   1740
ctgcaccagg actggctgaa cggcaaggag tacaagtgca aggtgagcaa caagggcctg   1800
ccaagcagca tcgagaagac catcagcaag gccaagggcc agccacgcga gccacaggtg   1860
tacaccctgc caccaagcca ggaggagatg accaagaacc aggtgagcct gagctgcgcc   1920
gtgaagggct tctacccaag cgacatcgcc gtggagtggg agagcaacgg ccagccagag   1980
aacaactaca agaccacccc accagtgctg gacagcgacg gcagcttctt cctggtgagc   2040
cgcctgaccg tggacaagag ccgctggcag gagggcaacg tgttcagctg cagcgtgatg   2100
cacgaggccc tgcacaaccg cttcacccag aagagcctga gcctgagcct gggcaagatg   2160
gcctgggtgt ggaccctgct gttcctgatg gccgccgccc agagcatcca ggccgacatc   2220
cagatgaccc agagcccaag cagcctgagc gccagcgtgg gcgaccgcgt gaccatcacc   2280
tgccgcagca gccagagcct ggtgcacagc aacggcaaca cctacctgca ctggtaccag   2340
cagaagccag gcaaggcccc aaagttcctg atctacaagg tgagcaaccg cttcagcggc   2400
gtgccaagcc gcttcagcgg cagcggcagc ggcaccgact caccctgac catcagcagc   2460 ctgcagccag aggacttcgc cacctactac tgcagccaga gcacccacgt gccattcacc   2520
ttcggccagg gcaccaagct ggagatcaag cgcaccgtgg ccgccccaag cgtgttcatc   2580
ttcccaccaa gcgacgagca gctgaagagc ggcaccgcca gcgtggtgtg cctgctgaac   2640
aacttctacc cacgcgaggc caaggtgcag tggaaggtgg acaacgccct gcagagcggc   2700
aacagccagg agagcgtgac cgagcaggac agcaaggaca gcacctacag cctgagcagc   2760
accctgaccc tgagcaaggc cgactacgag aagcacaagg tgtacgcctg cgaggtgacc   2820
```

```
caccagggcc tgagcagccc agtgaccaag agcttcaacc gcggcgagtg cggcggcagc   2880
gagggcaaga gcagcggcag cggcagcgag agcaagagca ccgagggcaa gagcagcggc   2940
agcggcagcg agagcaagag caccggcggc agccaggtgc agctgcagga gagcggccca   3000
ggcctggtga agccaagcga gaccctgagc ctgacctgca ccgtgagcgg ctacagcatc   3060
accagcggct acttctggaa ctggatccgc cagccaccag gcaagggcct ggagtggatc   3120
ggctacatca gctacgacgg cagcaacaac tacaacccaa gcctgaagag ccgcgtgacc   3180
atcagccgcg acaccagcaa gaaccagttc agcctgaagc tgagcagcgt gaccgccgcc   3240
gacaccgccg tgtactactg cgccagccca agcccaggca ccggctacgc cgtggactac   3300
tggggccagg gcaccctggt gaccgtgagc agcgccagca ccaagggccc aagcgtgttc   3360
ccactggccc catgcagccg cagcaccagc gagagcaccg ccgccctggg ctgcctggtg   3420
aaggactact cccagagcca gtgaccgtg agctggaaca gcggcgccct gaccagcggc   3480
gtgcacacct tccagccgt gctgcagagc agcggcctgt acagcctgag cagcgtggtg   3540
accgtgccaa gcagcagcct gggcaccaag acctacacct gcaacgtgga ccacaagcca   3600
agcaacacca aggtggacaa gcgcgtggag agcaagtacg gcccaccatg cccaccatgc   3660
ccagccccag aggccgccgg cggcccaagc gtgttcctgt tcccaccaaa gccaaaggac   3720
accctgatga tcagccgcac cccagaggtg acctgcgtgg tggtggacgt gagccaggag   3780
gacccagagg tgcagttcaa ctggtacgtg gacggcgtgg aggtgcacaa cgccaagacc   3840
aagccacgcg aggagcagtt caacagcacc taccgcgtgg tgagcgtgct gaccgtgctg   3900
caccaggact ggctgaacgg caaggagtac aagtgcaagg tgagcaacaa gggcctgcca   3960
agcagcatcg agaagaccat cagcaaggcc aagggccagc cacgcgagcc acaggtgtac   4020
accctgccac caagccagga ggagatgacc aagaaccagg tgagcctgag ctgcgccgtg   4080
aagggcttct acccaagcga catcgccgtg gagtgggaga gcaacggcca gccagagaac   4140
aactacaaga ccaccccacc agtgctggac agcgacggca gcttcttcct ggtgagccgc   4200
ctgaccgtgg acaagagccg ctggcaggag ggcaacgtgt tcagctgcag cgtgatgcac   4260
gaggccctgc acaaccgctt cacccagaag agcctgagcc tgagcctggg caagtgatag   4320
```

<210> SEQ ID NO 30
<211> LENGTH: 713
<212> TYPE: PRT
<213> ORGANISM: Artificial Sequence
<220> FEATURE:
<223> OTHER INFORMATION: I3RB217 half antibody

<400> SEQUENCE: 30

```
Met Ala Trp Val Trp Thr Leu Leu Phe Leu Met Ala Ala Ala Gln Ser
1               5                   10                  15

Ile Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95
```

-continued

Arg Leu Glu Pro Glu Asp Phe Ala Val Tyr Tyr Cys Gln Gln Asp Tyr
                100                 105                 110

Gly Phe Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Ser Glu Gly Lys
225                 230                 235                 240

Ser Ser Gly Ser Gly Ser Glu Ser Lys Ser Thr Glu Gly Lys Ser Ser
                245                 250                 255

Gly Ser Gly Ser Glu Ser Lys Ser Thr Gly Gly Ser Glu Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Ser Trp
290                 295                 300

Val Arg Gln Met Pro Gly Lys Gly Leu Glu Trp Met Gly Ile Ile Asp
305                 310                 315                 320

Pro Ser Asp Ser Asp Thr Arg Tyr Ser Pro Ser Phe Gln Gly Gln Val
                325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Asp
        355                 360                 365

Gly Ser Thr Asp Leu Asp Tyr Trp Gly Gln Gly Thr Leu Val Thr Val
    370                 375                 380

Ser Ser Ala Ser Thr Lys Gly Pro Ser Val Phe Pro Leu Ala Pro Cys
385                 390                 395                 400

Ser Arg Ser Thr Ser Glu Ser Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr
    450                 455                 460

Lys Thr Tyr Thr Cys Asn Val Asp His Lys Pro Ser Asn Thr Lys Val
465                 470                 475                 480

Asp Lys Arg Val Glu Ser Lys Tyr Gly Pro Pro Cys Pro Pro Cys Pro
                485                 490                 495

Ala Pro Glu Ala Ala Gly Gly Pro Ser Val Phe Leu Phe Pro Pro Lys
            500                 505                 510

Pro Lys Asp Thr Leu Met Ile Ser Arg Thr Pro Glu Val Thr Cys Val

```
                515                 520                 525
Val Val Asp Val Ser Gln Glu Asp Pro Glu Val Gln Phe Asn Trp Tyr
    530                 535                 540

Val Asp Gly Val Glu Val His Asn Ala Lys Thr Lys Pro Arg Glu Glu
545                 550                 555                 560

Gln Phe Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Gln Glu Glu Met
    610                 615                 620

Thr Lys Asn Gln Val Ser Leu Trp Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Arg Leu Thr Val Asp Lys Ser Arg Trp Gln Glu Gly Asn Val
        675                 680                 685

Phe Ser Cys Ser Val Met His Glu Ala Leu His Asn His Tyr Thr Gln
    690                 695                 700

Lys Ser Leu Ser Leu Ser Leu Gly Lys
705                 710

<210> SEQ ID NO 31
<211> LENGTH: 2139
<212> TYPE: DNA
<213> ORGANISM: Artificial Sequence
<220> FEATURE:
<223> OTHER INFORMATION: I3RB217 half antibody

<400> SEQUENCE: 31
atggcctggg tgtggaccct gctgttcctg atggccgccg cccagagcat ccaggccgag    60
atcgtgctga cccagagccc aggcaccctg agcctgagcc caggcgagcg cgccacccTG   120
agctgccgcg ccagccagag cgtgagcagc agctacctgg cctggtacca gcagaagcca   180
ggccaggccc cacgcctgct gatctacggc gccagcagcc gcgccaccgg catcccagac   240
cgcttcagcg gcagcggcag cggcaccgac ttcaccctga ccatcagccg cctggagcca   300
gaggacttcg ccgtgtacta ctgccagcag gactacggct cccatggac cttcggccag   360 ggcaccaagg tggagatcaa agcgaccgtg gccgccccaa gcgtgttcat cttcccacca   420
agcgacgagc agctgaagag cggcaccgcc agcgtggtgt gcctgctgaa caacttctac   480
ccacgcgagg ccaaggtgca gtggaaggtg gacaacgccc tgcagagcgg caacagccag   540
gagagcgtga ccgagcagga cagcaaggac agcacctaca gcctgagcag caccctgacc   600
ctgagcaagg ccgactacga gaagcacaag gtgtacgcct gcgaggtgac ccaccagggc   660
ctgagcagcc cagtgaccaa gagcttcaac cgcggcgagt gcggcggcag cgagggcaag   720
agcagcggca gcggcagcga gagcaagagc accgagggca gagcagcgg cagcggcagc   780 gagagcaaga gcaccggcgg cagcgaggtg cagctggtgc agagcggcgc cgaggtgaag   840
aagccaggcg agagcctgaa gatcagctgc aagggcagcg gctacagctt caccagctac   900
tggatcagct gggtgcgcca gatgccaggc aagggcctgg agtggatggg catcatcgac   960
```

```
ccaagcgaca gcgacacccg ctacagccca agcttccagg gccaggtgac catcagcgcc      1020
gacaagagca tcagcaccgc ctacctgcag tggagcagcc tgaaggccag cgacaccgcc      1080
atgtactact gcgcccgcgg cgacggcagc accgacctgg actactgggg ccagggcacc      1140
ctggtgaccg tgagcagcgc cagcaccaag ggcccaagcg tgttcccact ggcccccatgc     1200 agccgcagca ccagcgagag caccgccgcc ctgggctgcc tggtgaagga ctacttccca      1260
gagccagtga ccgtgagctg gaacagcggc gccctgacca cggcgtgca caccttccca      1320 gccgtgctgc agagcagcgg cctgtacagc ctgagcagcg tggtgaccgt gccaagcagc      1380
agcctgggca ccaagaccta cacctgcaac gtggaccaca gccaagcaa caccaaggtg      1440 gacaagcgcg tggagagcaa gtacggccca ccatgcccac catgcccagc cccagaggcc      1500
gccggcggcc aagcgtgtt cctgttccca ccaaagccaa aggacaccct gatgatcagc      1560 cgcacccag aggtgacctg cgtggtggtg gacgtgagcc aggaggaccc agaggtgcag     1620
ttcaactggt acgtggacgg cgtggaggtg cacaacgcca agaccaagcc acgcgaggag      1680
cagttcaaca gcacctaccg cgtggtgagc gtgctgaccg tgctgcacca ggactggctg      1740
aacggcaagg agtacaagtg caaggtgagc aacaagggcc tgccaagcag catcgagaag      1800
accatcagca aggccaaggg ccagccacgc gagccacagg tgtacaccct gccaccaagc      1860
caggaggaga tgaccaagaa ccaggtgagc ctgtggtgcc tggtgaaggg cttctaccca      1920
agcgacatcg ccgtggagtg ggagagcaac ggccagccag agaacaacta caagaccacc      1980
ccaccagtgc tggacagcga cggcagcttc ttcctgtaca gccgcctgac cgtggacaag      2040
agccgctggc aggagggcaa cgtgttcagc tgcagcgtga tgcacgaggc cctgcacaac      2100
cactacaccc agaagagcct gagcctgagc ctgggcaag                             2139
```

<210> SEQ ID NO 32
<211> LENGTH: 713
<212> TYPE: PRT
<213> ORGANISM: Artificial Sequence
<220> FEATURE:
<223> OTHER INFORMATION: B23B49 half antibody

<400> SEQUENCE: 32

```
Met Ala Trp Val Trp Thr Leu Leu Phe Leu Met Ala Ala Ala Gln Ser
1               5                   10                  15

Ile Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Asp Tyr
            100                 105                 110

Gly Phe Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
            145                 150                 155                 160
Pro Arg Glu Ala Lys Val Gln Trp Lys Val Asp Asn Ala Leu Gln Ser
                    165                 170                 175
Gly Asn Ser Gln Glu Ser Val Thr Glu Gln Asp Ser Lys Asp Ser Thr
                    180                 185                 190
Tyr Ser Leu Ser Ser Thr Leu Thr Leu Ser Lys Ala Asp Tyr Glu Lys
                    195                 200                 205
His Lys Val Tyr Ala Cys Glu Val Thr His Gln Gly Leu Ser Ser Pro
        210                 215                 220
Val Thr Lys Ser Phe Asn Arg Gly Glu Cys Gly Gly Ser Glu Gly Lys
225                 230                 235                 240
Ser Ser Gly Ser Gly Ser Glu Ser Lys Ser Thr Glu Gly Lys Ser Ser
                    245                 250                 255
Gly Ser Gly Ser Glu Ser Lys Ser Thr Gly Gly Ser Glu Val Gln Leu
                260                 265                 270
Val Gln Ser Gly Ala Glu Val Lys Lys Pro Gly Glu Ser Leu Lys Ile
            275                 280                 285
Ser Cys Lys Gly Ser Gly Tyr Ser Phe Thr Ser Tyr Trp Ile Ser Trp
    290                 295                 300
Val Arg Gln Met Pro Gly Lys Gly Leu Glu Trp Met Gly Ile Ile Asp
305                 310                 315                 320
Pro Ser Asp Ser Asp Thr Arg Tyr Ser Pro Ser Phe Gln Gly Gln Val
                325                 330                 335
Thr Ile Ser Ala Asp Lys Ser Ile Ser Thr Ala Tyr Leu Gln Trp Ser
                340                 345                 350
Ser Leu Lys Ala Ser Asp Thr Ala Met Tyr Tyr Cys Ala Arg Gly Asp
            355                 360                 365
Gly Ser Thr Asp Leu Asp Tyr Trp Gly Gln Gly Thr Leu Val Thr Val
        370                 375                 380
Ser Ser Ala Ser Thr Lys Gly Pro Ser Val Phe Pro Leu Ala Pro Cys
385                 390                 395                 400
Ser Arg Ser Thr Ser Glu Ser Thr Ala Ala Leu Gly Cys Leu Val Lys
                405                 410                 415
Asp Tyr Phe Pro Glu Pro Val Thr Val Ser Trp Asn Ser Gly Ala Leu
                420                 425                 430
Thr Ser Gly Val His Thr Phe Pro Ala Val Leu Gln Ser Ser Gly Leu
            435                 440                 445
Tyr Ser Leu Ser Ser Val Val Thr Val Pro Ser Ser Ser Leu Gly Thr
        450                 455                 460
Lys Thr Tyr Thr Cys Asn Val Asp His Lys Pro Ser Asn Thr Lys Val
465                 470                 475                 480
Asp Lys Arg Val Glu Ser Lys Tyr Gly Pro Pro Cys Pro Pro Cys Pro
                485                 490                 495
Ala Pro Glu Ala Ala Gly Gly Pro Ser Val Phe Leu Phe Pro Pro Lys
                500                 505                 510
Pro Lys Asp Thr Leu Met Ile Ser Arg Thr Pro Glu Val Thr Cys Val
            515                 520                 525
Val Val Asp Val Ser Gln Glu Asp Pro Glu Val Gln Phe Asn Trp Tyr
    530                 535                 540
Val Asp Gly Val Glu Val His Asn Ala Lys Thr Lys Pro Arg Glu Glu
545                 550                 555                 560
Gln Phe Asn Ser Thr Tyr Arg Val Val Ser Val Leu Thr Val Leu His
                565                 570                 575
```

```
Gln Asp Trp Leu Asn Gly Lys Glu Tyr Lys Cys Lys Val Ser Asn Lys
            580                 585                 590
Gly Leu Pro Ser Ser Ile Glu Lys Thr Ile Ser Lys Ala Lys Gly Gln
        595                 600                 605
Pro Arg Glu Pro Gln Val Tyr Thr Leu Pro Pro Ser Gln Glu Glu Met
    610                 615                 620
Thr Lys Asn Gln Val Ser Leu Trp Cys Leu Val Lys Gly Phe Tyr Pro
625                 630                 635                 640
Ser Asp Ile Ala Val Glu Trp Glu Ser Asn Gly Gln Pro Glu Asn Asn
                645                 650                 655
Tyr Lys Thr Thr Pro Pro Val Leu Asp Ser Asp Gly Ser Phe Phe Leu
            660                 665                 670
Tyr Ser Arg Leu Thr Val Asp Lys Ser Arg Trp Gln Glu Gly Asn Val
        675                 680                 685
Phe Ser Cys Ser Val Met His Glu Ala Leu His Asn His Tyr Thr Gln
    690                 695                 700
Lys Ser Leu Ser Leu Ser Leu Gly Lys
705                 710
```

<210> SEQ ID NO 33
<211> LENGTH: 2154
<212> TYPE: DNA
<213> ORGANISM: Artificial Sequence
<220> FEATURE:
<223> OTHER INFORMATION: B23B49 half antibody

<400> SEQUENCE: 33

```
atggcctggg tgtggaccct gctgttcctg atggccgccg cccagagcat ccaggccgac      60
atcgtgatga cccagagccc agacagcctg gccgtgagcc tgggcgagcg cgccaccatc     120
aactgccgcg ccagccagag cgtggactac aacggcatca gctacatgca ctggtaccag     180
cagaagccag gccagccacc aaagctgctg atctacgccg ccagcaaccc agagagcggc     240
gtgccagacc gcttcagcgg cagcggcagc ggcaccgact tcaccctgac catcagcagc     300
ctgcaggcca aggacgtggc cgtgtactac tgccagcaga tcatcgagga ccccatggacc    360
ttcggccagg gcaccaaggt ggagatcaag cgcaccgtgg ccgccccaag cgtgttcatc     420
ttcccaccaa gcgacgagca gctgaagagc ggcaccgcca gcgtggtgtg cctgctgaac     480
aacttctacc cacgcgaggc caaggtgcag tggaaggtgg acaacgccct gcagagcggc     540
aacagccagg agagcgtgac cgagcaggac agcaaggaca gcacctacag cctgagcagc     600
accctgaccc tgagcaaggc cgactacgag aagcacaagg tgtacgcctg cgaggtgacc     660
caccagggcc tgagcagccc agtgaccaag agcttcaacc gcggcgagtg cggcggcagc     720
gagggcaaga gcagcggcag cggcagcgag agcaagagca ccgagggcaa gagcagcggc     780
agcggcagcg agagcaagag caccggcggc agccagatca ccctgaagga gagcggccca     840
accctggtga agccaaccca gaccctgacc ctgacctgca ccttcagcgg cttcagcctg     900
agcaccagcg gcatgggcgt gagctggatc cgccagccac aggcaaggc cctggagtgg     960
ctggcccaca tctactggga cgacgacaag cgctacaacc caagcctgaa gagccgcctg    1020
accatcacca aggacaccag caagaaccag gtggtgctga ccatgaccaa catggaccca    1080
gtggacaccg ccacctacta ctgcgcccgc ctgtacggct tcacctacgg cttcgcctac    1140
tggggccagg gcaccctggt gaccgtgagc agcgccagca caagggccc aagcgtgttc    1200
ccactggccc catgcagccg cagcaccagc gagagcaccg ccgccctggg ctgcctggtg    1260
```

-continued

```
aaggactact tcccagagcc agtgaccgtg agctggaaca gcggcgccct gaccagcggc    1320
gtgcacacct tccagccgt gctgcagagc agcggcctgt acagcctgag cagcgtggtg     1380
accgtgccaa gcagcagcct gggcaccaag acctacacct gcaacgtgga ccacaagcca    1440
agcaacacca aggtggacaa gcgcgtggag agcaagtacg gcccaccatg cccaccatgc    1500
ccagccccag aggccgccgg cggcccaagc gtgttcctgt tcccaccaaa gccaaaggac    1560
accctgatga tcagccgcac cccagaggtg acctgcgtgg tggtggacgt gagccaggag    1620
gacccagagg tgcagttcaa ctggtacgtg gacggcgtgg aggtgcacaa cgccaagacc    1680
aagccacgcg aggagcagtt caacagcacc taccgcgtgg tgagcgtgct gaccgtgctg    1740
caccaggact ggctgaacgg caaggagtac aagtgcaagg tgagcaacaa gggcctgcca    1800
agcagcatcg agaagaccat cagcaaggcc aaggccagc cacgcgagcc acaggtgtac     1860
accctgccac caagccagga ggagatgacc aagaaccagg tgagcctgtg gtgcctggtg    1920
aagggcttct acccaagcga catcgccgtg gagtgggaga gcaacggcca gccagagaac    1980
aactacaaga ccacccccacc agtgctggac agcgacggca gcttcttcct gtacagccgc   2040
ctgaccgtgg acaagagccg ctggcaggag gcaacgtgt tcagctgcag cgtgatgcac     2100
gaggccctgc acaaccacta cacccagaag agcctgagcc tgagcctggg caag          2154
```

<210> SEQ ID NO 34
<211> LENGTH: 5
<212> TYPE: PRT
<213> ORGANISM: Artificial Sequence
<220> FEATURE:
<223> OTHER INFORMATION: I3RB217 HCDR1

<400> SEQUENCE: 34

Ser Tyr Trp Ile Ser
1               5

<210> SEQ ID NO 35
<211> LENGTH: 17
<212> TYPE: PRT
<213> ORGANISM: Artificial Sequence
<220> FEATURE:
<223> OTHER INFORMATION: I3RB217 HCDR2

<400> SEQUENCE: 35

Ile Ile Asp Pro Ser Asp Ser Asp Thr Arg Tyr Ser Pro Ser Phe Gln
1               5                   10                  15
Gly

<210> SEQ ID NO 36
<211> LENGTH: 9
<212> TYPE: PRT
<213> ORGANISM: Artificial Sequence
<220> FEATURE:
<223> OTHER INFORMATION: I3RB217 HCDR3

<400> SEQUENCE: 36

Gly Asp Gly Ser Thr Asp Leu Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: I3RB217 LCDR1

```
<400> SEQUENCE: 37

Arg Ala Ser Gln Ser Val Ser Ser Ser Tyr Leu
1               5                   10

<210> SEQ ID NO 38
<211> LENGTH: 7
<212> TYPE: PRT
<213> ORGANISM: Artificial Sequence
<220> FEATURE:
<223> OTHER INFORMATION: I3RB217 LCDR2

<400> SEQUENCE: 38

Gly Ala Ser Ser Arg Ala Thr
1               5

<210> SEQ ID NO 39
<211> LENGTH: 9
<212> TYPE: PRT
<213> ORGANISM: Artificial Sequence
<220> FEATURE:
<223> OTHER INFORMATION: I3RB217 LCDR3

<400> SEQUENCE: 39

Gln Gln Asp Tyr Gly Phe Pro Trp Thr
1               5

<210> SEQ ID NO 40
<211> LENGTH: 118
<212> TYPE: PRT
<213> ORGANISM: Artificial Sequence
<220> FEATURE:
<223> OTHER INFORMATION: I3RB217 HC

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser
        115

<210> SEQ ID NO 41
<211> LENGTH: 108
<212> TYPE: PRT
<213> ORGANISM: Artificial Sequence
<220> FEATURE:
<223> OTHER INFORMATION: I3RB217 LC

<400> SEQUENCE: 41

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys
            100                 105
```

<210> SEQ ID NO 42
<211> LENGTH: 11
<212> TYPE: PRT
<213> ORGANISM: Artificial Sequence
<220> FEATURE:
<223> OTHER INFORMATION: IGHJ1*01 HC

<400> SEQUENCE: 42

```
Trp Gly Gln Gly Thr Leu Val Thr Val Ser Ser
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: IGKJ2*01 LC

<400> SEQUENCE: 43

```
Phe Gly Gln Gly Thr Lys Leu Glu Ile Lys
1               5                   10
```

<210> SEQ ID NO 44
<211> LENGTH: 449
<212> TYPE: PRT
<213> ORGANISM: Artificial Sequence
<220> FEATURE:
<223> OTHER INFORMATION: Va10.2_Fc fusion

<400> SEQUENCE: 44

```
Met Ala Trp Val Trp Thr Leu Leu Phe Leu Met Ala Ala Ala Gln Ser
1               5                   10                  15

Ile Gln Ala Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Ala Gly Ser
            100                 105                 110

Gln Gly Asn Leu Ile Phe Gly Lys Gly Thr Lys Leu Ser Val Lys Pro
        115                 120                 125

Asn Ile Gln Asn Pro Asp Pro Ala Val Tyr Gln Leu Arg Asp Ser Lys
```

```
                130               135               140
Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
                195                 200                 205

Ile Ile Pro Glu Asp Thr Phe Phe Pro Ser Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Val Tyr Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly
```